US009117321B2

(12) United States Patent
Davis et al.

(10) Patent No.: US 9,117,321 B2
(45) Date of Patent: Aug. 25, 2015

(54) METHOD AND APPARATUS TO USE REMOTE AND LOCAL CONTROL MODES TO ACQUIRE AND VISUALLY PRESENT DATA

(75) Inventors: Robert E. Davis, Palatine, IL (US); Michel B. Alberry, San Jose, CA (US); Timothy G. Ruther, Carpentersville, IL (US); Anthony J. Cichy, Cary, IL (US)

(73) Assignee: Snap-on Incorporated, Kenosha, WI (US)

( * ) Notice: Subject to any disclaimer, the term of this patent is extended or adjusted under 35 U.S.C. 154(b) by 754 days.

(21) Appl. No.: 12/913,249

(22) Filed: Oct. 27, 2010

(65) Prior Publication Data

US 2012/0044052 A1 Feb. 23, 2012

Related U.S. Application Data

(60) Provisional application No. 61/374,723, filed on Aug. 18, 2010.

(51) Int. Cl.

*G06F 3/00* (2006.01)
*G01M 17/00* (2006.01)

(Continued)

(52) U.S. Cl.

CPC .............. *G07C 5/0825* (2013.01); *G07C 5/008* (2013.01); *G07C 2205/02* (2013.01)

(58) Field of Classification Search

CPC .......... G06F 3/00; G01M 17/00; G01M 15/00
USPC .................... 340/439, 6.1; 710/16; 701/29, 8; 128/630, 696, 903

See application file for complete search history.

(56) References Cited

U.S. PATENT DOCUMENTS 2,587,079 A 2/1952 Woods et al.
2,680,210 A 6/1954 Miller et al.

(Continued)

FOREIGN PATENT DOCUMENTS

CA 2373157 A1 3/2000
DE 19543784 A1 5/1997

(Continued)

OTHER PUBLICATIONS

Metzelaar, R.H.M., Automotive Oscilloscope Applications, Peugeot 205 Holding Back, downloaded from the World Wide Web at http://www.tiepie.com/uk/automotive/GMT/peugeot_205_holding_back.html on Jul. 12, 2010, pp. 1-4.

(Continued)

*Primary Examiner* — Nam V Nguyen
(74) *Attorney, Agent, or Firm* — McDonnell Boehnen Hulbert & Berghoff LLP

(57) ABSTRACT

A system comprising multiple devices that are operable when servicing a device-under service is described. A data acquisition (DAQ) device and a vehicle scanner device of the system are operable to acquire data from the device-under-service and to transmit the acquired data to a display device of the system. The DAQ device can operate in a local-control mode in which selection of DAQ mode for the DAQ device is carried out at the DAQ device. The DAQ device can operate in a remote-control mode in which selection of a DAQ mode for the DAQ device is carried out at the display device. The multiple devices may communicate with each other via one or more wireless network via one or more air interface protocols. Each device of the system may operate as a stand-alone device or in combination with multiple devices of the system.

25 Claims, 25 Drawing Sheets

(51) Int. Cl.
*A61B 5/00* (2006.01)
*G07C 5/08* (2006.01)
*G07C 5/00* (2006.01)

(56) References Cited

U.S. PATENT DOCUMENTS 4,058,826 A 11/1977 Schneider
4,072,851 A 2/1978 Rose
4,104,725 A 8/1978 Rose et al.
4,113,980 A 9/1978 Bell
4,257,104 A 3/1981 Martin et al.
4,270,174 A 5/1981 Karlin et al.
4,404,639 A 9/1983 McGuire et al.
4,441,359 A 4/1984 Ezoe
4,602,127 A 7/1986 Neely et al.
4,774,438 A 9/1988 Rogers et al.
4,814,896 A 3/1989 Heitzman et al.
4,853,850 A 8/1989 Krass, Jr. et al.
4,962,456 A 10/1990 Abe et al.
5,157,610 A 10/1992 Asano et al.
5,160,892 A 11/1992 Makhija et al.
5,317,304 A 5/1994 Choi
5,365,436 A 11/1994 Schaller et al.
5,373,458 A 12/1994 Bishay et al.
5,396,168 A 3/1995 Heep et al.
5,417,222 A * 5/1995 Dempsey et al. ............. 600/509
5,432,904 A 7/1995 Wong
5,442,553 A 8/1995 Parrillo
5,465,207 A 11/1995 Boatwright et al.
5,506,772 A 4/1996 Kubozono et al.
5,507,288 A * 4/1996 Bocker et al. ................. 600/322
5,521,443 A 5/1996 Imura et al.
5,532,927 A 7/1996 Pink et al.
5,541,840 A 7/1996 Gurne et al.
5,583,912 A 12/1996 Schillaci et al.
5,592,383 A 1/1997 Rogers et al.
5,687,717 A * 11/1997 Halpern et al. ............... 600/300
5,758,300 A 5/1998 Abe
5,766,020 A 6/1998 Hughes
5,836,666 A * 11/1998 Aoyama et al. ............... 353/122
5,850,209 A 12/1998 Lemke et al.
5,884,202 A 3/1999 Arjomand
5,899,947 A 5/1999 Hall et al.
5,923,161 A 7/1999 Frankovitch, Jr. et al.
6,021,366 A 2/2000 Fieramosca et al.
6,055,468 A 4/2000 Kaman et al.
6,067,486 A 5/2000 Aragones et al.
6,094,609 A 7/2000 Arjomand
6,134,489 A 10/2000 Smedley
6,140,811 A 10/2000 Little
6,169,943 B1 1/2001 Simon et al.
6,178,527 B1 1/2001 Vidales
6,179,214 B1 1/2001 Key et al.
6,181,563 B1 1/2001 Shimbo et al.
6,188,384 B1 2/2001 Sullivan et al.
6,192,303 B1 2/2001 Takakura et al.
6,195,617 B1 2/2001 Miller
6,222,374 B1 4/2001 Shoemaker
6,294,982 B1 9/2001 Hooks et al.
6,311,138 B2 10/2001 Miller
6,314,422 B1 11/2001 Barker et al.
6,321,151 B1 11/2001 Shultz
6,356,823 B1 3/2002 Iannotti et al.
6,360,551 B1 3/2002 Renders
6,374,315 B1 4/2002 Okada et al.
6,385,300 B1 5/2002 Mohammadian et al.
6,401,049 B1 6/2002 Ehmer
6,416,471 B1 7/2002 Kumar et al.
6,477,478 B1 11/2002 Jones et al.
6,487,478 B1 11/2002 Azzaro et al.
6,609,050 B2 8/2003 Li
6,622,070 B1 9/2003 Wacker et al.
6,640,166 B2 10/2003 Liebl et al.
6,662,123 B2 12/2003 Maeckel et al.
6,693,367 B1 2/2004 Schmeisser et al.
6,711,524 B2 3/2004 Wolf et al.
6,745,151 B2 6/2004 Marko et al.
6,748,335 B2 6/2004 Pickerd
6,757,521 B1 6/2004 Ying
6,778,931 B1 8/2004 Letts et al.
6,789,007 B2 9/2004 Ellis et al.
6,802,032 B1 10/2004 Budinger et al.
6,807,469 B2 10/2004 Funkhouser et al.
6,807,496 B2 10/2004 Pickerd
6,822,639 B1 11/2004 Silverbrook et al.
6,823,243 B2 11/2004 Chinnadurai et al.
6,844,823 B2 1/2005 Hooks et al.
6,847,916 B1 1/2005 Ying
6,873,940 B1 3/2005 Kamatani
6,947,043 B1 9/2005 Klingman et al.
6,957,128 B1 10/2005 Ito et al.
6,959,235 B1 10/2005 Abdel-Malek et al.
6,972,669 B2 12/2005 Saito et al.
6,982,653 B2 1/2006 Voeller et al.
6,988,053 B2 1/2006 Namaky
7,020,546 B2 3/2006 Nagai et al.
7,023,332 B2 4/2006 Saito et al.
7,073,714 B2 7/2006 Namaky et al.
7,124,058 B2 10/2006 Namaky et al.
7,155,321 B2 12/2006 Bromley et al.
7,200,483 B1 4/2007 Kavadeles
7,224,262 B2 5/2007 Simon et al.
7,251,552 B2 7/2007 Schmeisser et al.
7,254,550 B2 8/2007 Reichwein et al.
7,269,482 B1 9/2007 Shultz et al.
7,272,476 B2 9/2007 Ortiz et al.
7,281,663 B2 10/2007 Schmidt et al.
7,294,906 B2 11/2007 Ukaji
7,327,228 B2 2/2008 Min et al.
7,336,082 B1 2/2008 Mofield
7,346,922 B2 3/2008 Miliefsky
7,350,159 B2 * 3/2008 Cancilla et al. ............... 715/854
7,363,129 B1 4/2008 Barnicle et al.
7,383,318 B2 6/2008 Craik
7,444,216 B2 10/2008 Rogers et al.
7,504,926 B2 3/2009 Bessho et al.
7,530,949 B2 * 5/2009 Al Ali et al. .................. 600/300
7,535,466 B2 5/2009 Sampsell et al.
7,580,781 B2 8/2009 Mindeman
7,613,554 B2 11/2009 Rollinger et al.
7,634,337 B2 12/2009 Brozovich et al.
7,648,062 B2 1/2010 Corniot
7,702,437 B2 4/2010 Gilbert
7,711,462 B2 5/2010 Daniels et al.
7,737,860 B2 * 6/2010 Banta et al. ................ 340/691.6
7,751,955 B2 7/2010 Chinnadurai et al.
7,907,295 B2 3/2011 Ono
8,412,401 B2 * 4/2013 Bertosa et al. ............... 701/29.1
8,463,953 B2 * 6/2013 Davis et al. ..................... 710/16
8,670,437 B2 3/2014 Walker et al.
2001/0001850 A1 5/2001 Miller
2002/0040261 A1 4/2002 Nakamoto et al.
2002/0077780 A1 6/2002 Leibl et al.
2003/0020759 A1 1/2003 Cancilla et al.
2003/0034767 A1 2/2003 Lipscomb et al.
2003/0036832 A1 2/2003 Kokes et al.
2003/0058243 A1 3/2003 Faust et al.
2003/0088346 A1 5/2003 Calkins et al.
2003/0122671 A1 7/2003 Jesperson
2003/0208328 A1 11/2003 Pickerd
2003/0208330 A1 11/2003 Pickerd
2003/0222873 A1 12/2003 Ritter
2004/0054503 A1 3/2004 Namaky
2004/0088087 A1 5/2004 Fukushima et al.
2004/0172177 A1 9/2004 Nagai et al.
2004/0193918 A1 9/2004 Green et al.
2005/0083965 A1 4/2005 Sodergren
2005/0089055 A1 4/2005 Klose et al.
2005/0094588 A1 5/2005 Wentink
2005/0152294 A1 7/2005 Yu et al.
2005/0157732 A1 7/2005 Joy et al.
2005/0182537 A1 8/2005 Tefft et al.
2005/0267655 A1 12/2005 Gessner
2006/0025897 A1 2/2006 Shostak et al.

(56) References Cited

U.S. PATENT DOCUMENTS

| | | | |
|---|---|---|---|
| 2006/0036355 | A1 | 2/2006 | Schaar et al. |
| 2006/0062190 | A1 | 3/2006 | Suga |
| 2006/0066504 | A1 | 3/2006 | Sampsell et al. |
| 2006/0078175 | A1 | 4/2006 | Brozovich |
| 2006/0101311 | A1 | 5/2006 | Lipscomb et al. |
| 2006/0106508 | A1 | 5/2006 | Liebl et al. |
| 2006/0149434 | A1 | 7/2006 | Bertosa et al. |
| 2006/0180371 | A1 | 8/2006 | Breed et al. |
| 2006/0199537 | A1 | 9/2006 | Eisenbach |
| 2006/0212239 | A1 | 9/2006 | Letts et al. |
| 2006/0212540 | A1 | 9/2006 | Chon et al. |
| 2006/0226298 | A1 | 10/2006 | Pierson |
| 2006/0287776 | A1 | 12/2006 | Giles et al. |
| 2007/0010922 | A1 | 1/2007 | Buckley |
| 2007/0043488 | A1 | 2/2007 | Avery et al. |
| 2007/0072154 | A1 | 3/2007 | Akatsuka et al. |
| 2007/0073459 | A1 | 3/2007 | Webster et al. |
| 2007/0073460 | A1 | 3/2007 | Bertosa et al. |
| 2007/0083307 | A1 | 4/2007 | Pasztor et al. |
| 2007/0100520 | A1 | 5/2007 | Shah et al. |
| 2007/0146133 | A1 | 6/2007 | Wehrenberg |
| 2007/0156311 | A1 | 7/2007 | Elcock et al. |
| 2007/0156313 | A1 | 7/2007 | Fudali et al. |
| 2007/0200550 | A1 | 8/2007 | Corredoura |
| 2007/0233340 | A1 | 10/2007 | Raichle et al. |
| 2007/0244611 | A1 | 10/2007 | Brozovich |
| 2007/0244614 | A1 | 10/2007 | Nathanson |
| 2007/0288134 | A1 | 12/2007 | Rollinger et al. |
| 2007/0290847 | A1 | 12/2007 | Harrington et al. |
| 2007/0294556 | A1 | 12/2007 | Wutka |
| 2008/0003997 | A1 | 1/2008 | Parkkinen et al. |
| 2008/0015748 | A1 | 1/2008 | Nagy |
| 2008/0033609 | A1 | 2/2008 | Razavi |
| 2008/0070501 | A1 | 3/2008 | Wyld |
| 2008/0076389 | A1 | 3/2008 | Lee et al. |
| 2008/0082221 | A1 | 4/2008 | Nagy |
| 2008/0082278 | A1 | 4/2008 | Tan et al. |
| 2008/0103658 | A1 | 5/2008 | Boac et al. |
| 2008/0122288 | A1 | 5/2008 | Plante et al. |
| 2008/0125067 | A1 | 5/2008 | Bells et al. |
| 2008/0140281 | A1 | 6/2008 | Morris et al. |
| 2008/0228344 | A1 | 9/2008 | Sampson et al. |
| 2008/0248748 | A1 | 10/2008 | Sangster et al. |
| 2008/0285659 | A1 | 11/2008 | Raines et al. |
| 2008/0298313 | A1 | 12/2008 | Salminen |
| 2008/0319665 | A1 | 12/2008 | Berkobin et al. |
| 2009/0043444 | A1 | 2/2009 | Gettner et al. |
| 2009/0112397 | A1 | 4/2009 | Roberts et al. |
| 2009/0125351 | A1 | 5/2009 | Davis, Jr. |
| 2009/0150970 | A1 | 6/2009 | Hinds et al. |
| 2009/0203247 | A1 | 8/2009 | Fifelski et al. |
| 2009/0256690 | A1 | 10/2009 | Golenski |
| 2009/0259349 | A1 | 10/2009 | Golenski |
| 2009/0265057 | A1 | 10/2009 | Chinnadurai et al. |
| 2009/0276115 | A1 | 11/2009 | Chen |
| 2009/0288009 | A1 | 11/2009 | Dulaney |
| 2009/0299539 | A1 | 12/2009 | Chinnadurai et al. |
| 2009/0307188 | A1 | 12/2009 | Oldham et al. |
| 2010/0042288 | A1 | 2/2010 | Lipscomb et al. |
| 2010/0076644 | A1 | 3/2010 | Cahill et al. |
| 2010/0100646 | A1 | 4/2010 | Park |
| 2010/0128632 | A1 | 5/2010 | Mantysalo |
| 2010/0179717 | A1 | 7/2010 | Gilbert |
| 2010/0205450 | A1 | 8/2010 | Sarnacke et al. |
| 2010/0289672 | A1 | 11/2010 | Nagatomo |
| 2011/0123039 | A1 | 5/2011 | Hirschfeld et al. |
| 2011/0141953 | A1 | 6/2011 | Wright et al. |
| 2011/0153798 | A1 | 6/2011 | Groenendaal et al. |
| 2011/0255411 | A1 | 10/2011 | Isaac et al. |
| 2011/0313593 | A1 | 12/2011 | Cohen et al. |
| 2012/0044086 | A1 | 2/2012 | Ruther et al. |
| 2012/0044527 | A1 | 2/2012 | Panko |
| 2012/0044607 | A1 | 2/2012 | Loewe |
| 2012/0045927 | A1 | 2/2012 | Panko et al. |
| 2012/0046807 | A1 | 2/2012 | Ruther et al. |
| 2012/0046824 | A1 | 2/2012 | Ruther et al. |
| 2012/0046825 | A1 | 2/2012 | Ruther et al. |
| 2012/0046826 | A1 | 2/2012 | Panko |
| 2012/0046897 | A1 | 2/2012 | Panko |
| 2012/0047289 | A1 | 2/2012 | Krzystofczyk et al. |
| 2012/0047291 | A1 | 2/2012 | Davis et al. |
| 2012/0047458 | A1 | 2/2012 | Alberry et al. |
| 2012/0047499 | A1 | 2/2012 | Krzystofczyk et al. |
| 2012/0084830 | A1 | 4/2012 | Dekok |
| 2012/0139952 | A1 | 6/2012 | Imai et al. |
| 2012/0242510 | A1 | 9/2012 | Choi et al. |

FOREIGN PATENT DOCUMENTS

| | | | |
|---|---|---|---|
| DE | 195 43 784 | A1 | 5/2007 |
| DE | 202009009035 | U1 | 9/2009 |
| DE | 20 2009 009 035 | U1 | 10/2009 |
| GB | 2277807 | A | 11/1994 |
| GB | 2385934 | A | 9/2003 |
| GB | 2405486 | A | 3/2005 |
| JP | 2008233970 | A | 10/2008 |
| WO | 9956201 | A1 | 11/1999 |
| WO | 00/34838 | A1 | 6/2000 |
| WO | 01/59601 | A1 | 8/2001 |
| WO | 0155690 | A1 | 8/2001 |
| WO | 0167420 | A1 | 9/2001 |
| WO | 0186576 | A1 | 11/2001 |
| WO | 2005121814 | A1 | 12/2005 |
| WO | 2006008527 | A2 | 1/2006 |
| WO | 2006/050454 | A2 | 5/2006 |
| WO | 2006055289 | A2 | 5/2006 |
| WO | 2006110786 | A2 | 10/2006 |
| WO | 2007022426 | A2 | 2/2007 |
| WO | 2007038983 | A1 | 4/2007 |
| WO | 2007058607 | A1 | 5/2007 |
| WO | 2008/043043 | A2 | 4/2008 |
| WO | 2008063818 | A2 | 5/2008 |
| WO | 2009/137584 | A1 | 11/2009 |
| WO | 2009149007 | A1 | 12/2009 |
| WO | 2010019771 | A1 | 2/2010 |

OTHER PUBLICATIONS

Zussman, Gil et al, Bluetooth Time Division Duplex Analysis as a Polling System, Aug. 19, 2004.

Fluke Corporation, Digital Multimeters, downloaded from the World Wide Web at http://us.fluke.com/usen/products/categorydmm on Jan. 28, 2010.

Fluke Corportation, 233 True=rms Remote Display Digital Multimeter Users Manual, Sep. 2009.

Bluetooth SIG, Inc., Bluetooth Architecture—Data Transport, downloaded from the World Wide Web at http://www.bluetooth.com/KnowledgeCenter/TechnologyOverview/Pages/DataTransport.aspx on May 6, 2010.

Shigeru et al, DL7100 Signal Explorer, A High-Speed Digital Oscilloscope with Long Record Length, Yokogawa Electric Corporation, Yogogawa Technical Report English Edition, No. 30, (2000).

bluetomorrow.com, Bluetooth Pairing downloaded from the World Wide Web at www.bluetomorrow.com on Apr. 30, 2010.

Snap-On Diagnostics, Snap-on Introduces VERDICT Diagnostic and Information System, Aug. 24, 2010.

Testpath, Inc., Fluke Meter Holsters, downloaded from the World Wide Web at http://www.testpath.com/Categories/Fluke-Meter-Holsters-2220.htm on May 6, 2010.

BMW Canada, Bluetooth Pairing Instructions, Sep. 2009.

Accessory Geeks, Bluetooth Pairing Guides, downloaded from the World Wide Web at http://www.accessorygeeks.com/bluetooth-pairing-guide1.html on Apr. 30, 2010.

Quatech, Inc., Bluetooth Communication Overview, downloaded from the World Wide Web at http://www.quatech.com/support/comm-over-bluetooth.php on May 3, 2010.

Omitec Limited, T4 Diagnostic System, downloaded from the World Wide Web at http://web.archive.org/web/20091119041838/http://www.omitec.com/us/products/diagnostic-testers/t4-diagnostic-system/ as archived on Nov. 19, 2009.

(56) References Cited

OTHER PUBLICATIONS

Omitec Limited, Workstations, downloaded from the World Wide Web at http://web.archive.org/web/20100322213801/http://www.omitec.com/us/products/workstation/ as archived on Mar. 22, 2010.
anotherurl.com, Bluetooth, What is Bluetooth? downloaded from the World Wide Web at http://www.anotherurl.com/library/bluetooth_research.htm on May 17, 2020.verdict.
Snap-On Incorporated, EEDM604C, Multimeter, Digital, Automotive, True RMS, Auto Ranging, Hybrid Vehicles, downloaded from the World Wide Web at http://buy1.snapon.com/catalog/item.asp?store=snapon-store&item_ID=88136&group_ID=1367 on May 4, 2010.
Snap-On Incorporated, EEDM596DK, Multimeter, Digital, Advanced, Manual Ranging, downloaded from the World Wide Web at http://buy1.snapon.com/catalog/item.asp?store=snapon-store&item_ID=84657&group_ID=1367 on May 4, 2010.
Snap-On Incorporated, EEDM503D, Multimeter, Digital, Automotive, True RMS, downloaded from the World Wide Web at http://buy1.snapon.com/catalog/item.asp?store=snapon-store&item_ID=84656&group_ID=1367 on May 4, 2010.
Fluke, 163/164 MultiFunction Counter Users Manual, Feb. 1, 1997.
Fluke, Fluke 164 2.7 GHz Multifunction Counter Technical Data, May 10, 2007.
Report Lab, OBD-II PIDS, Jul. 6, 2010.
Flores, J., Wireless Diagnostics and Consultancy Services, Vital Engineering, Jan. 4, 2007.
Fluke, Fluke 199B / 003 Scopemeter 200 MHz, Dual Portable Multimeter and Oscilloscope, downloaded from the World Wide Web at http://web.archive.org/web/20100413065253/http://www.fluke199.com/ as archived on Apr. 12, 2010.
Fluke Corporation, ScopeMeter 120 and 190 Series incl. 225C and 215C, Technical Data, Jan. 2010.
Fluke Corporation, Fluke 19xC-2x5C Scopemeter, Software version 8.00 onwards, Users Manual, Jul. 2008.
Metzelaar, R.H.M., Peugeot 205 Holding Back.
Jones, Mike, Senior FAE, Micrel Inc., Ethernet Driving Down Automotive Cost of Ownership; Oct. 31, 2008.
Nucology Engineering, Inc., Nology, PDA-Dyno and OBD II Scan Tool Operating Manual, 2009.
obd-2.com, OBDII Automotive Scan Tool and Virtual Dashboard, downloaded from the World Wide Web at http://www.obd-2.com/ on Jul. 11, 2010.
U.S. Appl. No. 12/859,077, filed Aug. 18, 2010.
U.S. Appl. No. 12/858,699, filed Aug. 18, 2010.
U.S. Appl. No. 12/859,082, filed Aug. 18, 2010.
U.S. Appl. No. 13/189,940, filed Jul. 25, 2011.
U.S. Appl. No. 13/205,318, filed Aug. 8, 2011.
U.S. Appl. No. 13/198,974, filed Aug. 5, 2011.
U.S. Appl. No. 13/198,530, filed Aug. 4, 2011.
U.S. Appl. No. 12/913,184, filed Oct. 27, 2010.
U.S. Appl. No. 12/859,011, filed Aug. 18, 2010.
U.S. Appl. No. 12/859,040, filed Aug. 18, 2010.
U.S. Appl. No. 12/858,725, filed Aug. 18, 2010.
U.S. Appl. No. 13/198,426, filed Aug. 4, 2011.
Paneda, Fernandez, J., European Patent Office, Written Opinion of the International Searching Authority for international application No. PCT/US2011/047332, Oct. 31, 2011.
Paneda, Fernandez, J., European Patent Office, International Search Report for international application No. PCT/US2011/047332, Oct. 31, 2011.
U.S. Appl. No. 12/859,051, filed Aug. 18, 2010.
Bluetooth SIG Inc., Bluetooth Specification Version 4.0, vol. 2, "Core System Package [BR/EDR Controller volume]," Part C "Link Manager Protocol Specification," Section 4.2 "Security", pp. 247-275, Jun. 30, 2010.
Engineer Live, "Ethernet makes it way into the car," Article date: Jun. 9, 2009, downloaded from the World Wide Web at http://www.engineerlive.com/Design-Engineer/Automotive_Design/Ethernet_makes_its_way_into_the_car/21822/ on Jul. 25, 2011, 4 pages.
OBD-II PIDs, downloaded from the World Wide Web at http://web.archive.org/web/20100329141311/http://en.wikipedia.org/wiki/OBD-II_PIDs, as available on Mar. 29, 2010, 13 pages.
Sorion Electronic Limited, J1962—OBD Diagnostics Connectors, downloaded from World Wide Web at http://www.sorion-group.com/SEL0051_connector.htm on May 24, 2010, pp. 1-3.
Memopad, The OBD2 Cable for Allpro adapter, downloaded from the World Wide Web at http://datawave.oommm.com/entry/USB-OBD2-AllPro-adapter, pp. 1-16, Oct. 8, 2008.
Tyco Electronics, Fundamentals of PolySwitch Overcurrent and Overtemperature Devices, pp. 1-13, Sep. 2, 2009.
International Organization for Standardization, ISO TC 22/SC 3, ISO 15031-1:2001(E), Road vehicles—Communication between vehicle and external test equipment for emissions-related diagnostics—Part 1: General information, 36 pages, Aug. 5, 2001.
International Organization for Standardization, ISO TC 22/SC 3 N, ISO/CD 22900-2, Road vehicles, Modular VCI (Vehicle Communication Interface)—Part 2: D-PDU API (Diagnostic Protocol Data Unit Application Programmer Interface), 144 pages, Mar. 31, 2005.
International Organization for Standardization, ISO TC 22/SC 3 N, ISO/CD 22900-1, Road vehicles—Modular Vehicle Communication Interface (MVCI)—Part 1: Hardware design requirements, 29 pages, Mar. 31, 2005.
International Organization for Standardization, ISO TC 22/SC 3 N, ISO/CD 22900-1, Road vehicles—Modular Vehicle Communication Interface (MVCI)—Part 3: D-Server API (Diagnostic Server Application Programmer Interface), 159 pages, Mar. 31, 2005.
International Organization for Standardization, ISO 15031-3:2400(E), Road vehicles—Communication between vehicle and external equipment for emissions-related diagnostics—Part 3: Diagnostic connector and related electrical circuits, specification and use—Annex B pp. 17-18, Jul. 2004.
Vital Engineering, Support and Frequently Asked Question regarding the Car-Pal OBD Interface Unit, Jan. 4, 2007, downloaded from the World Wide Web at http://www.vitalengineering.co.uk/support.htm, 8 pages.
Tech Shop Magazine; Snap-on Introduces VERDICT Diagnostic and Information System; Aug. 26, 2010; downloaded from the World Wide Web at http://www.techshopmag.com/Controls/PrinterFriendly/PrinterFriendly.aspx, 3 pages.
Snap-On Incorporated, Modis, Scanner Plug-in User Manual, ZEEMS303L, Rev. A, Aug. 2009, 61 pages.
Snap-On Incorporated, Modis, Display User Manual, ZEEMS300N, Rev. A, Aug. 2009, 72 pages.
Snap-On Incorporated, Modis, Component Tests User Manual, ZEEMS308G, Rev. C, Feb. 2009, 52 pages.
Snap-On Incorporated, Modis, Flexible Gas Analyzer User Manual, ZEEMS306B, Rev. A, Aug. 2009, 47 pages.
Snap-On Incorporated, Modis, Lab Scope Plug-in User Manual, ZEEMS305K, Rev. C, Feb. 2009, 73 pages.

* cited by examiner

METHOD AND APPARATUS TO USE REMOTE AND LOCAL CONTROL MODES TO ACQUIRE AND VISUALLY PRESENT DATA

PRIORITY CLAIM

Pursuant to 35 U.S.C. §119(e), this application claims the benefit of U.S. Provisional Application 61/374,723, filed Aug. 18, 2010.

BACKGROUND

Vehicles, such as automobiles, light-duty trucks, and heavy-duty trucks, play an important role in the lives of many people. To keep vehicles operational, some of those people rely on vehicle technicians to diagnose and repair their vehicle.

Vehicle technicians use a variety of tools in order to diagnose and/or repair vehicles. Those tools may include common hand tools, such as wrenches, hammers, pliers, screwdrivers and socket sets, or more vehicle-specific tools, such as cylinder hones, piston ring compressors, and vehicle brake tools. The tools used by vehicle technicians may also include electronic tools such as a digital voltage-ohm meter (DVOM) or a vehicle scan tool that communicates with an electronic control unit (ECU) within a vehicle.

Vehicle technicians may work at various locations of a vehicle in order to diagnose and/or repair the vehicle. For example, while working on an automobile having a passenger compartment and an under-hood area containing an internal combustion engine, a vehicle technician may desire to work at the under-hood area and at the passenger compartment. For example, the vehicle technician may desire to use a DVOM to make a voltage measurement at the under-hood area while the technician operates user controls within the passenger compartment so as to re-create a vehicle performance complaint (e.g., a cylinder misfire). However, the vehicle technician may be unable to view the DVOM at the under-hood area while operating the user controls within the passenger compartment. In such a situation, the vehicle technician may be unable to carry out the desired voltage measurement or the vehicle technician may need the assistance of another person to either operate the user controls or to read the DVOM.

OVERVIEW

Various example embodiments are described in this description. In one respect, an example embodiment may take the form of a method that comprises: (i) receiving, via a selector device located at a data acquisition (DAQ) device, a selection for the DAQ device to operate in a local-control mode, (ii) while the DAQ device is operating in the local-control mode, generating first input data from input signals received at an input element located at the DAQ device, displaying the first input data at a display located at the DAQ device, and then receiving, via the selector device, a selection for the DAQ device to operate in the remote-control mode, and (iii) while the DAQ device is operating in the remote-control mode, generating second input data from input signals received at the input element of the DAQ device and transmitting, via a wireless transceiver located at the DAQ device, the second input data to an air interface for transmission to a display device that is remote from the DAQ device.

In another respect, an example embodiment may take the form of an apparatus comprising (i) an input element operable to generate input data from input signals received at the input element, (ii) a wireless transceiver, (iii) a display, and (iv) a selector device that is operable to select whether the DAQ device operates in a local-control mode or a remote-control mode. When the DAQ device operates in the local-control mode, the display visually presents the input data. When the DAQ device operates in the remote-control mode, the wireless transceiver transmits the input data to an air interface for transmission to a display device remote from the DAQ device.

These as well as other aspects and advantages will become apparent to those of ordinary skill in the art by reading the following detailed description, with reference where appropriate to the accompanying drawings. Further, it should be understood that the embodiments described in this overview and elsewhere are intended to be examples only and do not necessarily limit the scope of the invention.

BRIEF DESCRIPTION OF THE DRAWINGS

Example embodiments are described herein with reference to the drawings, in which.

DETAILED DESCRIPTION

I. Introduction

This description describes a system including multiple devices for use in servicing (e.g., diagnosing and/or repairing) a device-under-service. The multiple devices may include a display device, a data acquisition (DAQ) device, and a vehicle scanner. The multiple devices may operate independently (e.g., as a stand-alone device) as well as in combination with each other. Each of the multiple devices may alternatively be referred to as an apparatus.

Each of the multiple devices is operable to carry out functions for servicing a device-under-service. The device-under-service may comprise a vehicle, a refrigeration unit, a personal computer, or some other serviceable device. Additionally or alternatively, the device-under-service may comprise a system such as a heating, ventilation, and air conditioning (HVAC) system, a security system, a computer system (e.g., a network), or some other serviceable system. The functions for servicing the device-under-service may include but are not limited to diagnostic functions, measurement functions, and scanning functions.

To work in combination with each other, the multiple devices are operable to communicate with each other via a communications network. The communications network may comprise a wireless network, a wired network, or both a wireless network and a wired network. Data obtained by a device from a device-under-service or data otherwise contained in that device may be transmitted to another device via the communications network.

A tool salesman may sell one or more of the devices of the described system to a technician that works on devices-under-service. By selling devices that are operable as stand-alone devices as well as within a system of multiple devices, the tool salesman can sell the devices to a technician one at a time until the technician acquires each of the multiple devices. This allows the technician to use the purchased device(s) on a device-under-service and to spread the cost of purchasing multiple devices over time without having to purchase the multiple devices all at once. Furthermore, the tool salesman may sell software applications (e.g., computer-readable program instructions) for execution on a device (e.g., a personal digital assistant) that the tool salesman does not sell, but that is operable to communicate with devices of the described system so as to service a device-under-service.

II. Example Architecture

Figure 1:
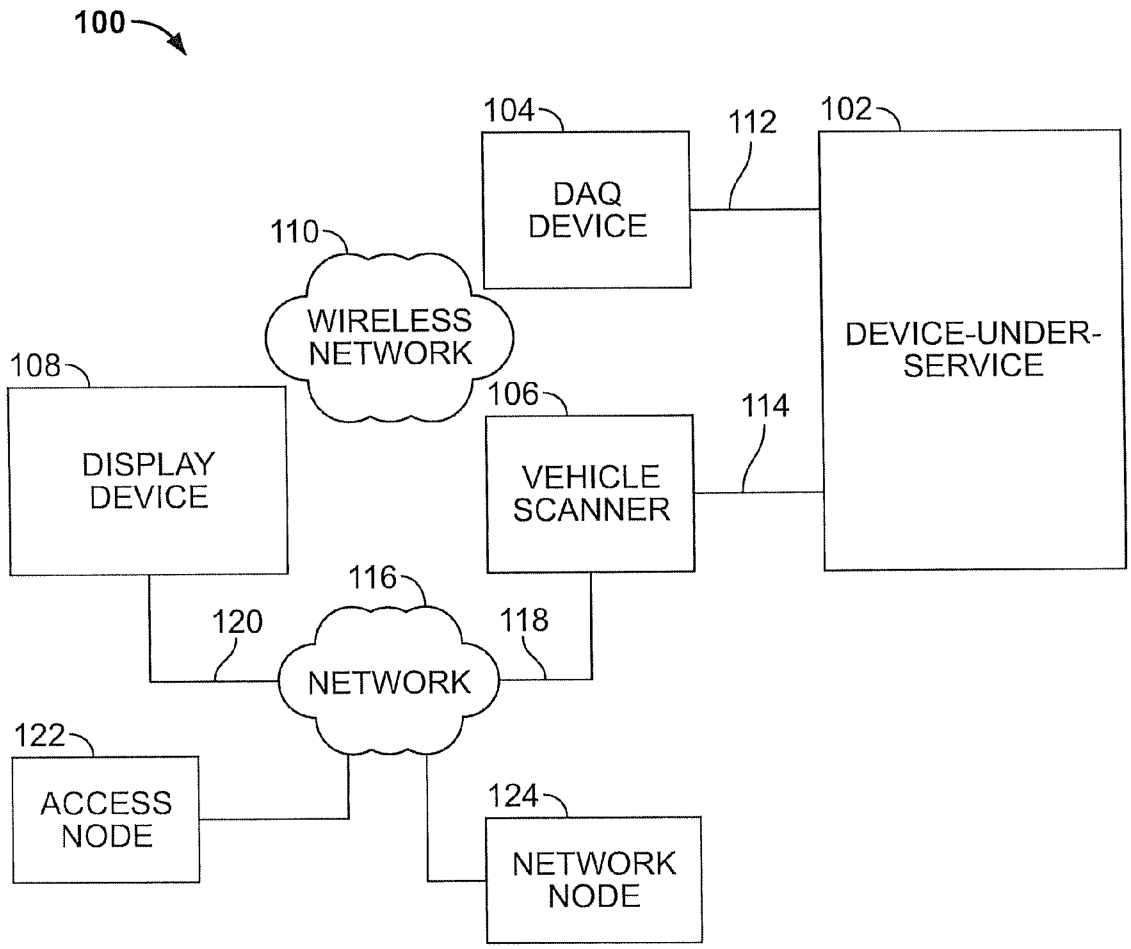
FIG. 1 is a block diagram of a system in accordance with an example embodiment.

FIG. 1 is a block diagram of a system 100 in accordance with an example embodiment. System 100 comprises a device-under-service 102, a data acquisition device (DAQ) device 104, a vehicle scanner 106, and a display device 108. Display device 108 may be referred to as a controller device since display device 108 may operate as a master of DAQ device 104 and/or vehicle scanner 106 when those devices are operating as a slave device or slave scanner, respectively.

The block diagram of FIG. 1 and other block diagrams and flow charts accompanying this description are provided merely as examples and are not intended to be limiting. Many of the elements illustrated in the figures and/or described herein are functional elements that may be implemented as discrete or distributed components or in conjunction with other components, and in any suitable combination and location. Those skilled in the art will appreciate that other arrangements and elements (for example, machines, interfaces, functions, orders, and groupings of functions, etc.) can be used instead. Furthermore, various functions described as being performed by one or more elements can be carried out by a processor executing computer-readable program instructions and/or by any combination of hardware, firmware, and software.

A wireless network 110 may be established between any two or more of DAQ device 104, vehicle scanner 106, and display device 108. DAQ device 104, vehicle scanner 106, and display device 108 are operable to carry out communications with each other via wireless network 110. Other devices, such as a personal digital assistant (PDA), may be operable to join wireless network 110 so as to communicate with devices communicating via wireless network 110.

Wireless network 110 may comprise one or more wireless networks. Each of the one or more wireless networks may be arranged to carry out communications according to a respective air interface protocol. Each air interface protocol may be arranged according to an industry standard, such as an Institute of Electrical and Electronics Engineers (IEEE) 802 standard. The IEEE 802 standard may comprise an IEEE 802.11 standard for Wireless Local Area Networks (e.g., IEEE 802.11a, b, g, or n), an IEEE 802.15 standard for Wireless Personal Area Networks, an IEEE 802.15.1 standard for Wireless Personal Area Networks—Task Group 1, an IEEE 802.16 standard for Broadband Wireless Metropolitan Area Networks, or some other IEEE 802 standard. For purposes of this description, a wireless network arranged to carry out communications according to the IEEE 802.11 standard is referred to as a Wi-Fi network, and a wireless network arranged to carry out communications according to the IEEE 802.15.1 is referred to as a Bluetooth network.

Figure 9:
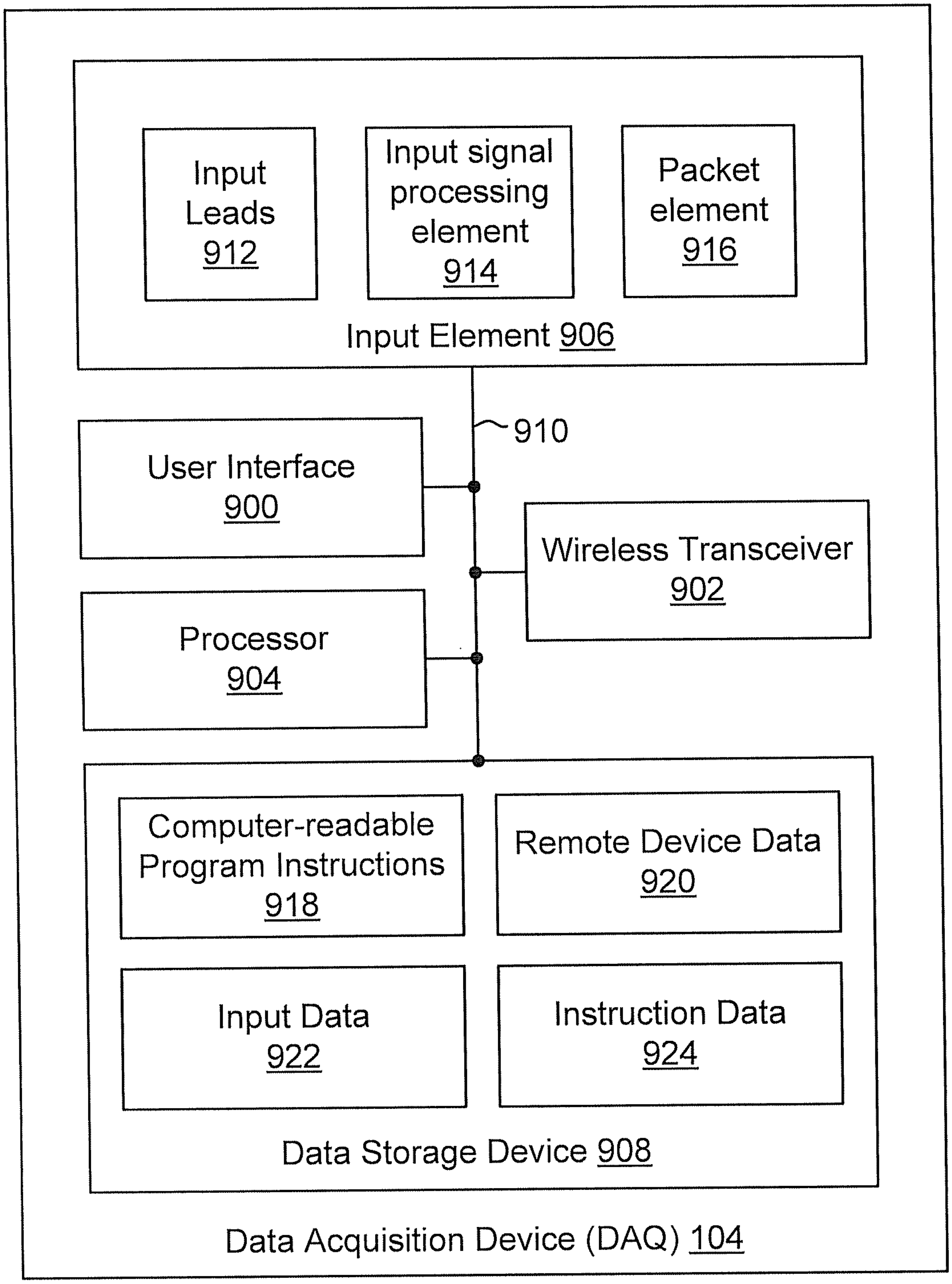
FIG. 9 is a block diagram of an example data acquisition (DAQ) device.

DAQ device 104 may connect to device-under-service 102 via wired link 112. Wired link 112 may comprise input leads 912, as shown in FIG. 9. DAQ device 104 may comprise a digital volt meter (DVM), a digital volt ohm meter (DVOM), an oscilloscope, or some other type of measurement device operational to acquire data from device-under-service 102.

Vehicle scanner 106 may connect to device-under-service 102 via wired link 114. Wired link 114 may be arranged as a cable assembly described in U.S. Patent Application No. 61/374,805, which is incorporated herein by reference, and which was filed on Aug. 18, 2010, and is entitled "Cable assembly for protection against undesired signals," or wired link 114 may be arranged as some other wired link. Vehicle scanner 106 may comprise a device that is operable to request and/or monitor data from one or more electronic control units (ECU) located on and/or within device-under-service 102. The data from the ECU(s) may comprise serial data arranged according to serial data available at an On Board Diagnostic (OBD) II connector within an automobile, such as a Society of Automotive Engineers (SAE) J1850 standard or an International Organization for Standardization (ISO) 9141-2 standard.

Vehicle scanner 106 may be operable as a stand-alone-device when vehicle scanner 106 operates as a data recorder to collect data from device-under-service 102 and other devices of system 100 are not connected to device-under-service 102 or communicating with vehicle scanner 106. Such data obtained when vehicle scanner operates as a data recorder can subsequently be displayed via another device of system 100, such as display device 108.

Device-under-service 102 may comprise a vehicle, such as an automobile, a motorcycle, a semi-tractor, a light-duty truck, a medium-duty truck, a heavy-duty truck, farm machinery, or some other vehicle. System 100 is operable to carry out a variety of functions, including functions for servicing device-under-service 102. The example embodiments may include or be utilized with any appropriate voltage or current source, such as a battery, an alternator, a fuel cell, and the like, providing any appropriate current and/or voltage, such as about 12 volts, about 42 volts, and the like. The example embodiments may be used with any desired system or engine. Those systems or engines may comprise items utilizing fossil fuels, such as gasoline, natural gas, propane, and the like, electricity, such as that generated by battery, magneto, fuel cell, solar cell and the like, wind and hybrids or combinations thereof. Those systems or engines may be incorporated into other systems, such as an automobile, a truck, a boat or ship, a motorcycle, a generator, an airplane and the like.

Vehicle scanner 106 and display device 108 may connect to a network 116 via wired links 118 and 120, respectively. Network 116 may include and/or connect to the Internet, and network 116 may include and/or connect to one or more network nodes, such as an access node 122 and a network node 124. Access node 122 may provide any of DAQ device 104, vehicle scanner 106, and display device 108 with wireless connectivity to network 116. Network node 124 may comprise a desktop personal computer (PC), a workstation that executes a Unix-based or Linux-based operating system, or some other node that interfaces and/or connects to network 116. In accordance with an example in which device-under-service 102 comprises an automobile, network node 124 may comprise a desktop PC or workstation operating at an automobile repair facility. In that regard, network node 124 may operate as a server that provides data (e.g., automobile repair data and/or instruction data) to display device 108.

Additional details regarding the elements shown in FIG. 1 are recited in U.S. Patent Application No. 61/374,825, which is incorporated herein by reference, and which was filed on Aug. 18, 2010, and is entitled "System and method for displaying input data on a remote display device," and in U.S. Patent Application No. 61/374,845, which is incorporated herein by reference, and which was filed on Aug. 18, 2010 and is entitled "System and method for simultaneous display of waveforms generated from input signals received at a data acquisition device."

Figure 2:
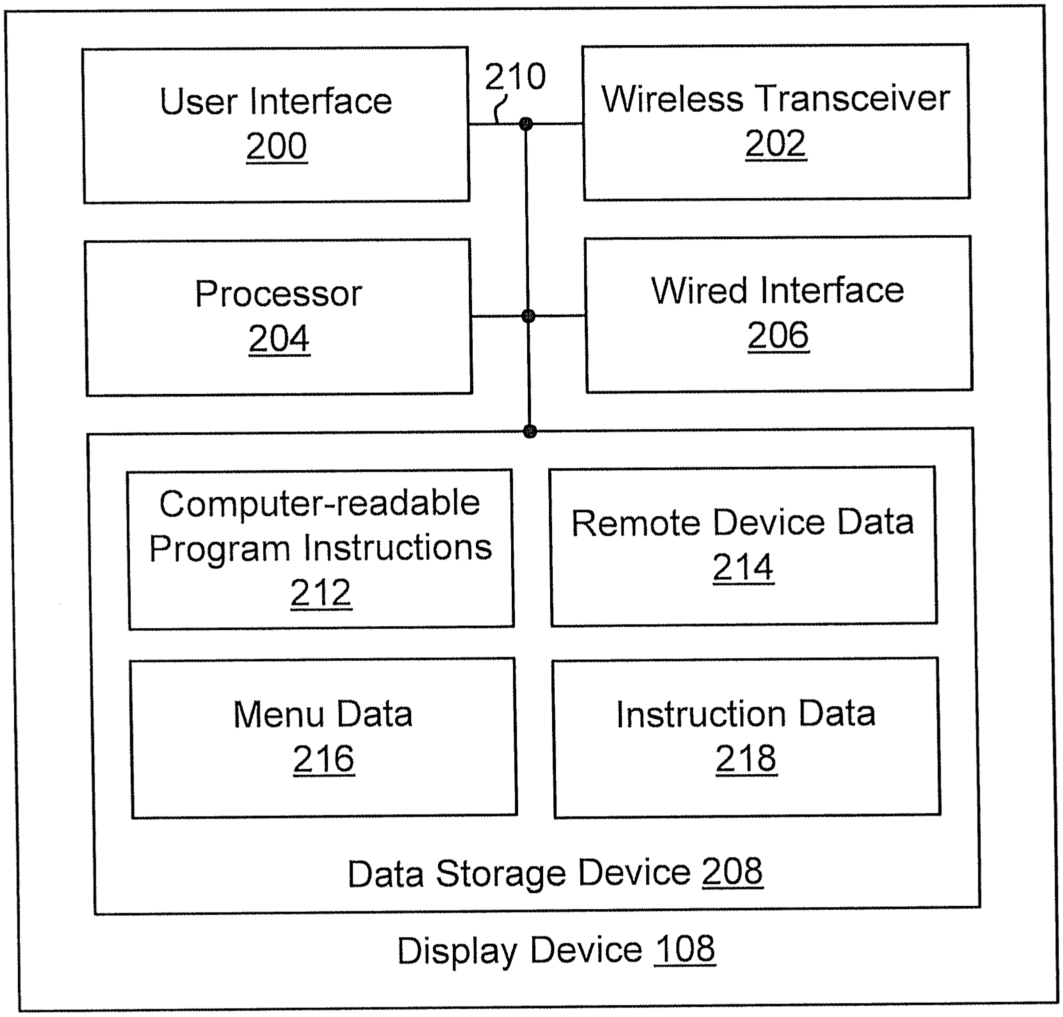
FIG. 2 is a block diagram of an example display device.

Next, FIG. 2 is a block diagram of display device 108, and FIG. 3 to FIG. 8 illustrate details of an example embodiment of display device 108. As illustrated in FIG. 2, display device 108 includes a user interface 200, a wireless transceiver 202, a processor 204, a wired interface 206, and a data storage device 208, all of which may be linked together via a system bus, network, or other connection mechanism 210.

Figure 3:
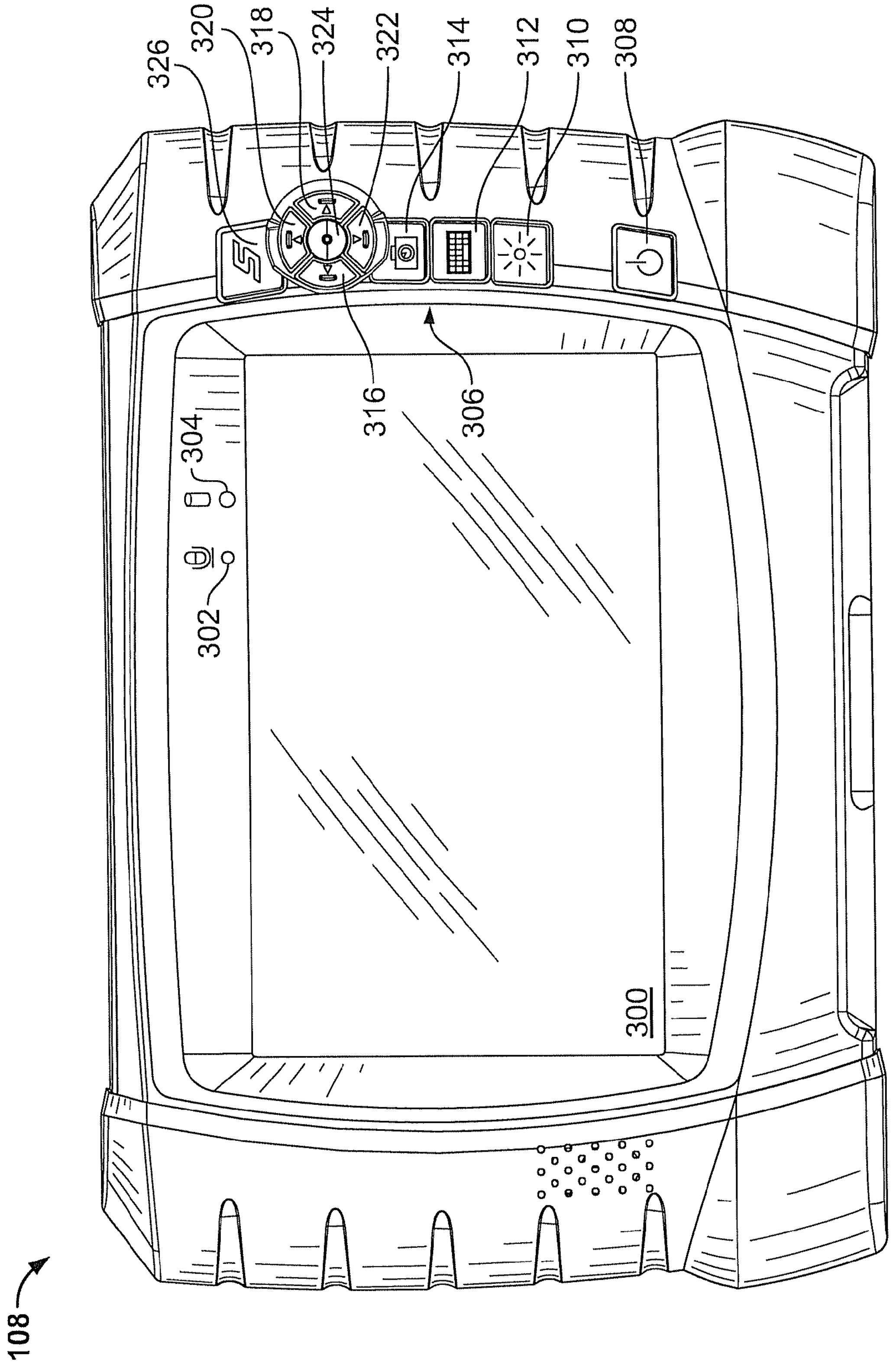
FIG. 3 to FIG. 8 illustrate various views of an example embodiment of the display device of FIG. 2.
Figure 4:
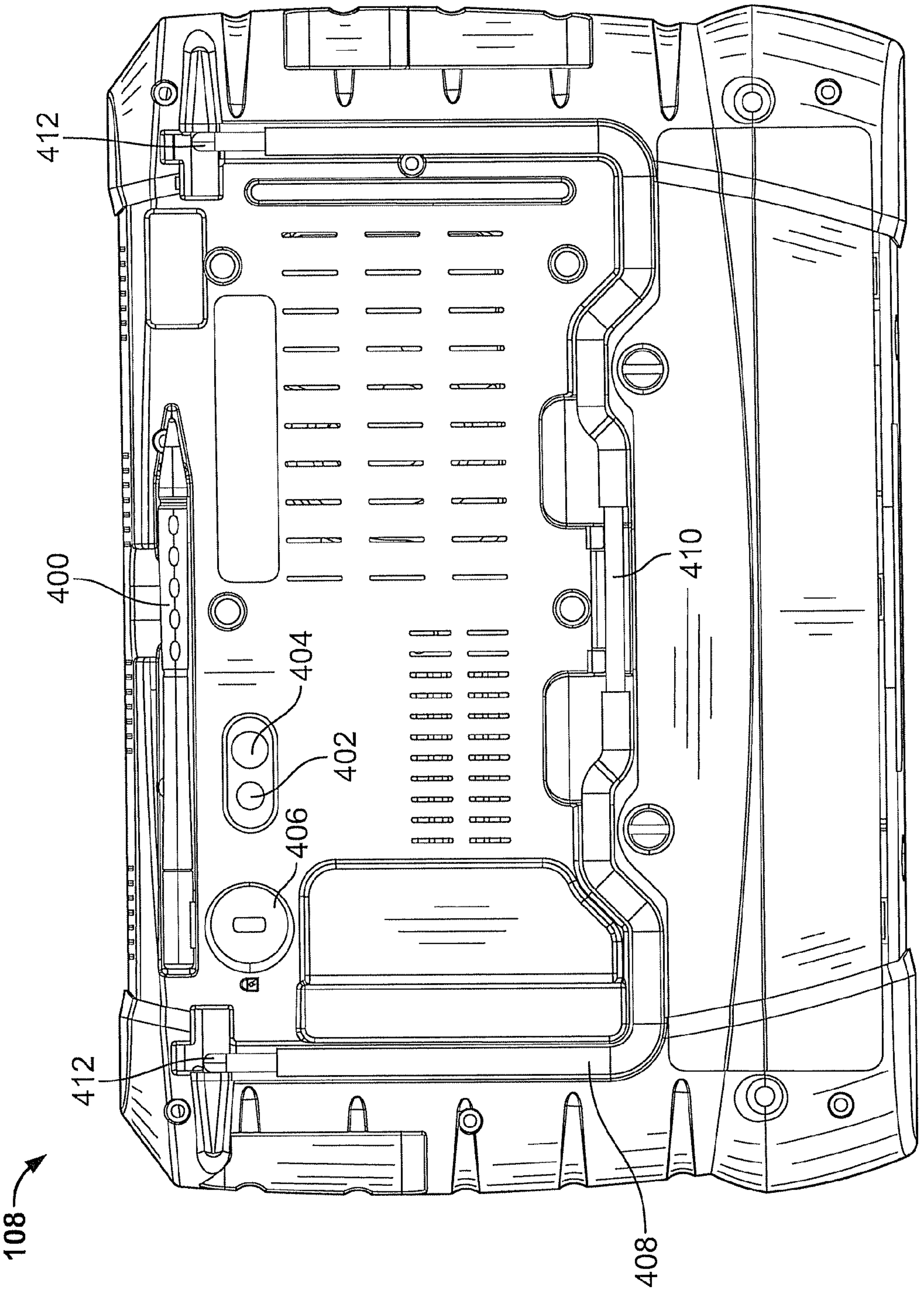

User interface 200 is operable to present data to a user and to enter user inputs (e.g., user selections). User interface 200 may include a display, such as display 300 illustrated in FIG. 3. Display 300 is operable to visually present data, such as data transmitted to wireless transceiver 202 from a remote device (e.g., DAQ device 104 or vehicle scanner 106), data that is transmitted to wired interface 206, data stored at data storage device 208 (e.g., menu data 216), or some other type of data. Display 300 may simultaneously display data that is transmitted to display device 108 from DAQ device 104 and data that is transmitted to display device 108 from vehicle scanner 106. User interface 200 may include a selection element that is operable to enter a user selection. Examples of the selection element are illustrated in FIG. 3 and FIG. 4.

Wireless transceiver 202 comprises a wireless transceiver that is operable to carry out communications via wireless network 110. Wireless transceiver 202 may carry out communications with one or more remote devices, such as one or more of DAQ device 104, vehicle scanner 106, and some other device (other than display device 108) that is operating to communicate via wireless network 110. As an example, wireless transceiver 202 may comprise a transceiver that is operable to carry out communications via a Bluetooth network. For purposes of this description, a transceiver that is operable to carry out communications via a Bluetooth network is referred to as a Bluetooth transceiver. As another example, wireless transceiver 202 may comprise a transceiver that is operable to carry out communications via a Wi-Fi network. For purposes of this description, a transceiver that is operable to carry out communications via a Wi-Fi network is referred to as a Wi-Fi transceiver.

In accordance with an embodiment in which DAQ device 104, vehicle scanner 106, and display device 108 each include a single wireless transceiver (e.g., a Bluetooth transceiver), one of the devices, such as display device 108, can operate as a master (e.g., a controller), and the other devices, such as DAQ device 104 and vehicle scanner 106, can operate as slaves to the master. DAQ device 104, vehicle scanner 106, and display device 108 may transmit communications via wireless network 110 using a time-division duplex arrangement and synchronized to a clock signal of the master.

Under a given implementation of a Bluetooth network, up to seven devices may actively exchange data with a master of the Bluetooth network. When one of the seven devices transitions from being an active device to a parked device, another parked device can transition from being a parked device to an active device that can exchange data with the master. If display device 108 is operating as the master of the Bluetooth network, then up to seven remote devices may actively exchange data with display device 108. As an example, the remote devices exchanging data with display device 108 may include DAQ device 104 and vehicle scanner 106. As another example, the remote devices exchanging data with display device 108 may include DAQ device 104, vehicle scanner 106, and another data acquisition device (arranged similar to DAQ device 104). Other examples of remote devices that can operate as one of seven devices actively exchanging data with display device 108 when display device 108 is operating as the master are also possible.

Wireless transceiver 202 is not limited to a single wireless transceiver. For example, wireless transceiver 202 may comprise a Bluetooth transceiver and a Wi-Fi transceiver. In accordance with such an example, the Bluetooth transceiver may communicate with DAQ device 104 and/or vehicle scanner 106 via a Bluetooth network of wireless network 110, and the Wi-Fi transceiver may communicate with DAQ device 104 and/or vehicle scanner 106 via a Wi-Fi network of wireless network 110.

In accordance with an embodiment in which display device 108 includes two wireless transceivers (e.g., a Bluetooth transceiver and a Wi-Fi transceiver) and DAQ device 104 and vehicle scanner 106 each include two wireless transceivers (e.g., a Bluetooth transceiver and a Wi-Fi transceiver), DAQ device 104 and vehicle scanner 106 may simultaneously transmit data to display device 108 for display via display 300. In that regard, DAQ device 104 may transmit data to display device 108 via the Bluetooth network of wireless network 110 and vehicle scanner 106 may transmit data to display device 108 via the Wi-Fi network of wireless network 110. Alternatively, DAQ device 104 and vehicle scanner 106 may take turns transmitting data to display device 108 via the Bluetooth network, the Wi-Fi network, or both the Bluetooth network and the Wi-Fi network.

In accordance with an embodiment in which wireless transceiver 202 includes three or more wireless transceivers, two or more of the wireless transceivers may communicate according to a common air interface protocol or different air interface protocols.

Each wireless transceiver of the example embodiments may operate in a transceiver-on state. In the transceiver-on state, the transceiver is powered on. While operating in the transceiver-on state, the transceiver can transmit and receive data via an air interface. For some transceivers, while operating in the transceiver-on state, the transceiver can transmit and receive data via the air interface simultaneously. For other transceivers, at any given time while operating in the transceiver-on state, the transceiver can either transmit data or receive data via the air interface. Each wireless transceiver of the example embodiments may operate in a transceiver-off state. While operating in the transceiver-off state, the transceiver does not transmit or receive data via an air interface. While operating in the transceiver-off state, the transceiver can be powered off.

Figure 5:
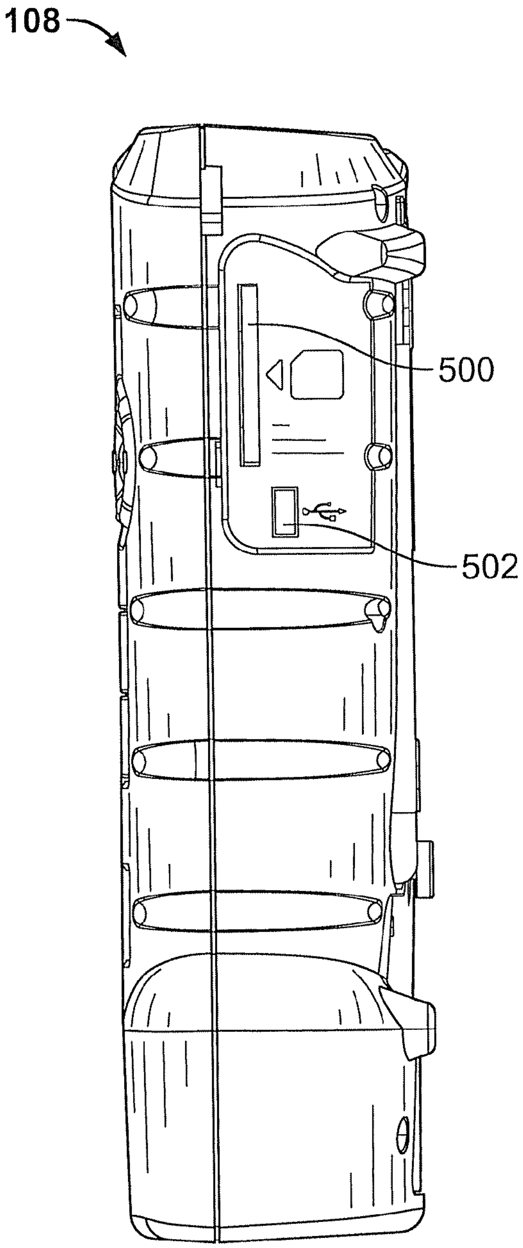
Figure 6:
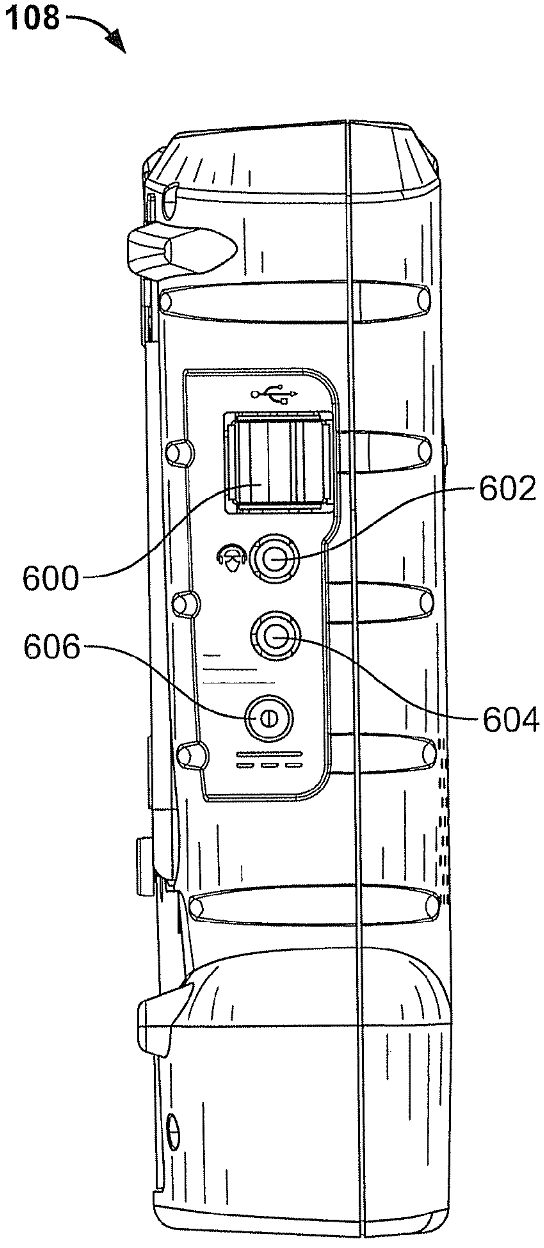

Wired interface 206 may include one or more ports. Examples of those ports are illustrated in FIG. 5 and FIG. 6. Each port of wired interface 206 provides an interface to display device 108 and to one or more circuits. In one respect, the one or more circuits may comprise electrical circuits, such as the electrical circuits of a Universal Serial Bus (USB) cable or the electrical circuits of an Ethernet cable (e.g., a CAT 5 cable). In another respect, the one or more circuits may comprise optical fibers that are operable to carry optical signals. Other examples of the one or more circuits are also possible.

Processor 204 may comprise one or more general purpose processors (e.g., INTEL microprocessors) and/or one or more special purpose processors (e.g., digital signal processors). Processor 204 may execute computer-readable program instructions (CRPI) 212 that are contained in computer-readable data storage device 208.

Data storage device 208 may comprise a computer-readable storage medium readable by processor 204. The computer-readable storage medium may comprise volatile and/or non-volatile storage components, such as optical, magnetic, organic or other memory or disc storage, which can be integrated in whole or in part with processor 204. Data storage device 208 may contain various data including, but not limited to, CRPI 212, remote device data 214, menu data 216, and instruction data 218.

Remote device data 214 may include data associated with a device that is arranged to communicate with display device 108 via wireless network 110. For example, remote device data 214 may include data associated with DAQ device 104, such as a radio identifier and password associated with DAQ device 104. The data associated with DAQ device 104 may be received at display device 108, for storing as remote device data 214, during a pairing process carried out between display device 108 and DAQ device 104. The pairing process between DAQ device 104 and display device 108 may include DAQ device 104 providing display device 108 with the data (e.g., a passkey) associated with DAQ device 104 and display device 108 providing DAQ device 104 with data (e.g., a passkey) associated with display device 108. After carrying out the paring process with DAQ device 104, display device 108 may use the remote device data 214 when establishing communication network 110 with DAQ device 104.

Remote device data 214 is not limited to data associated with one remote device. In that regard, remote device data 214 may include respective data associated with each of a plurality of devices operable to communicate via wireless network 110, such as data associated with DAQ device 104 and data associated with vehicle scanner 106. The data associated with vehicle scanner 106 may include a radio identifier and password associated with vehicle scanner 106. The data associated with vehicle scanner 106 may be received at display device 108, for storing as remote device data 214, during a pairing process carried out between display device 108 and vehicle scanner 106. The pairing process between vehicle scanner 106 and display device 108 may include vehicle scanner 106 providing display device 108 with the data associated with vehicle scanner 106 and display device 108 providing vehicle scanner 106 with data associated with display device 108. After carrying out the paring process with vehicle scanner 106, display device 108 may use the remote device data 214 when establishing wireless network 110 with vehicle scanner 106.

Instruction data 218 may comprise various data. As an example, instruction data 218 may comprise data that illustrates how to connect DAQ device 104 and/or vehicle scanner 106 to device-under-service 102. As another example, instruction data 218 may comprise diagnostic information for diagnosing device-under-service 102. For instance, in accordance with an example embodiment in which device-under-service 102 comprises an automobile, the diagnostic information may comprise diagnostic flow charts for diagnosing an electrical system on the automobile. The diagnostic flow charts can provide different paths to follow based on measurement data display device 108 obtains from DAQ device 104 and/or vehicle scanner 106. The diagnostic flow charts can guide a technician in diagnosing device-under-service 102 so as to determine the cause of a component or system failure within device-under-service 102.

Figure 29:
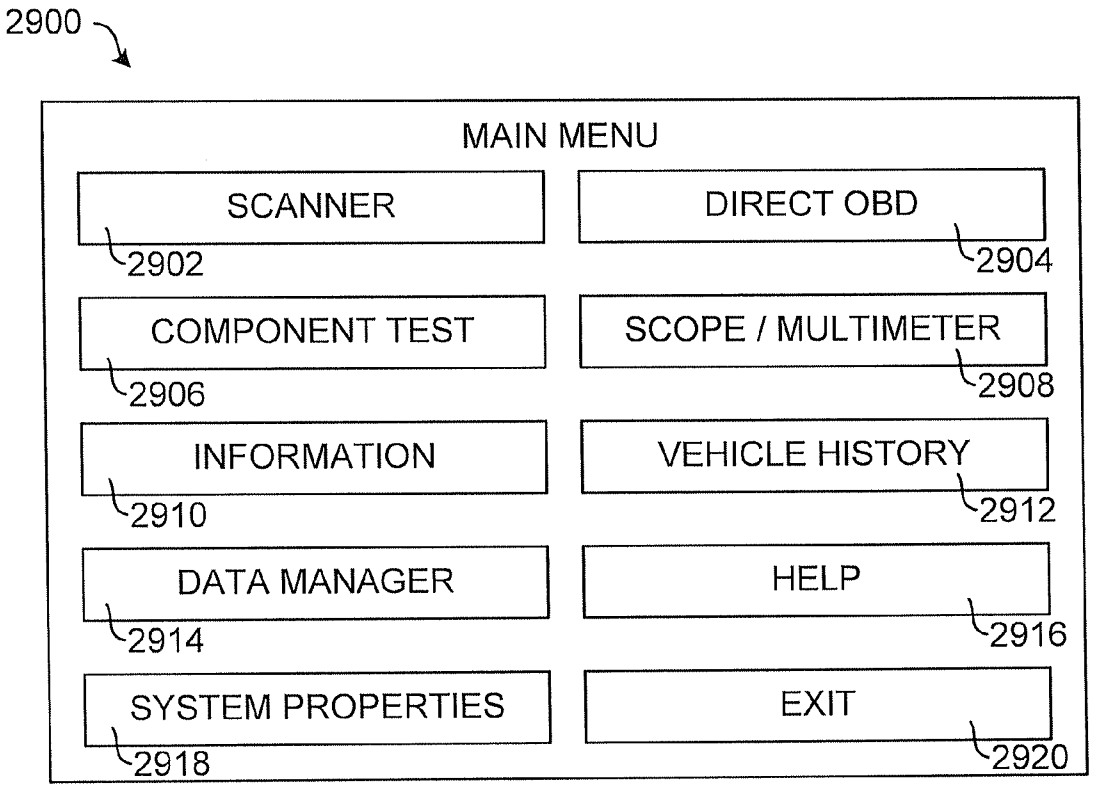
FIG. 29 to FIG. 31 illustrate example menu data displayable on an example device.
Figure 30:
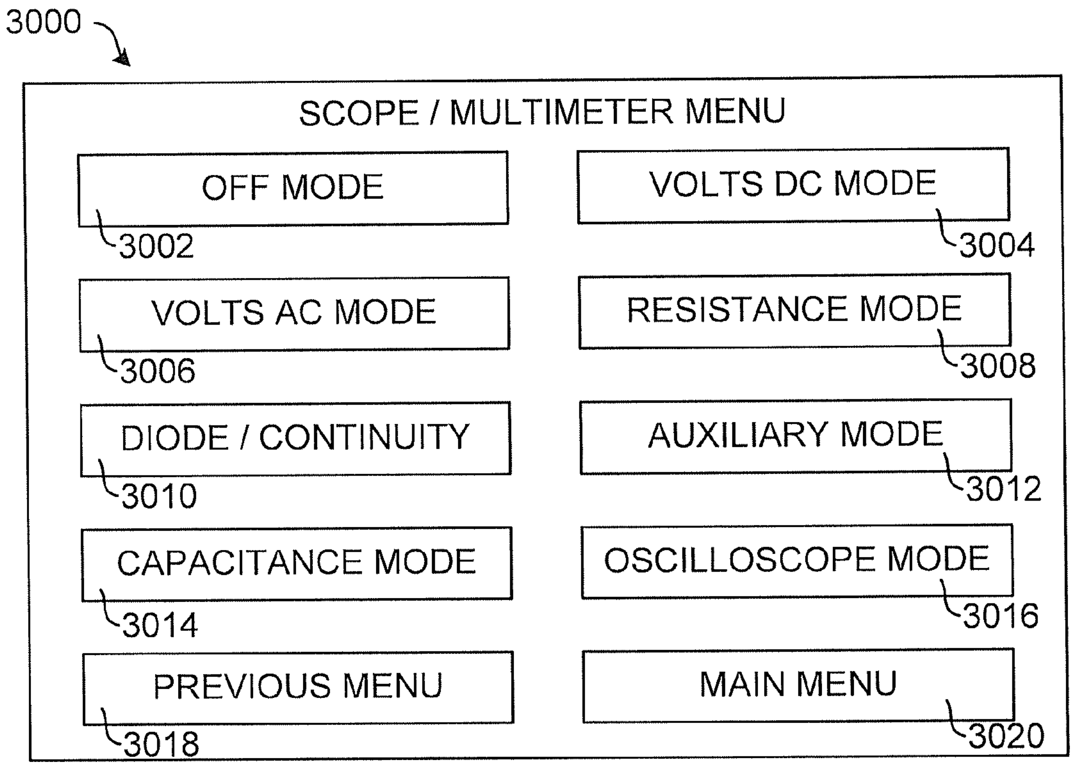
Figure 31:
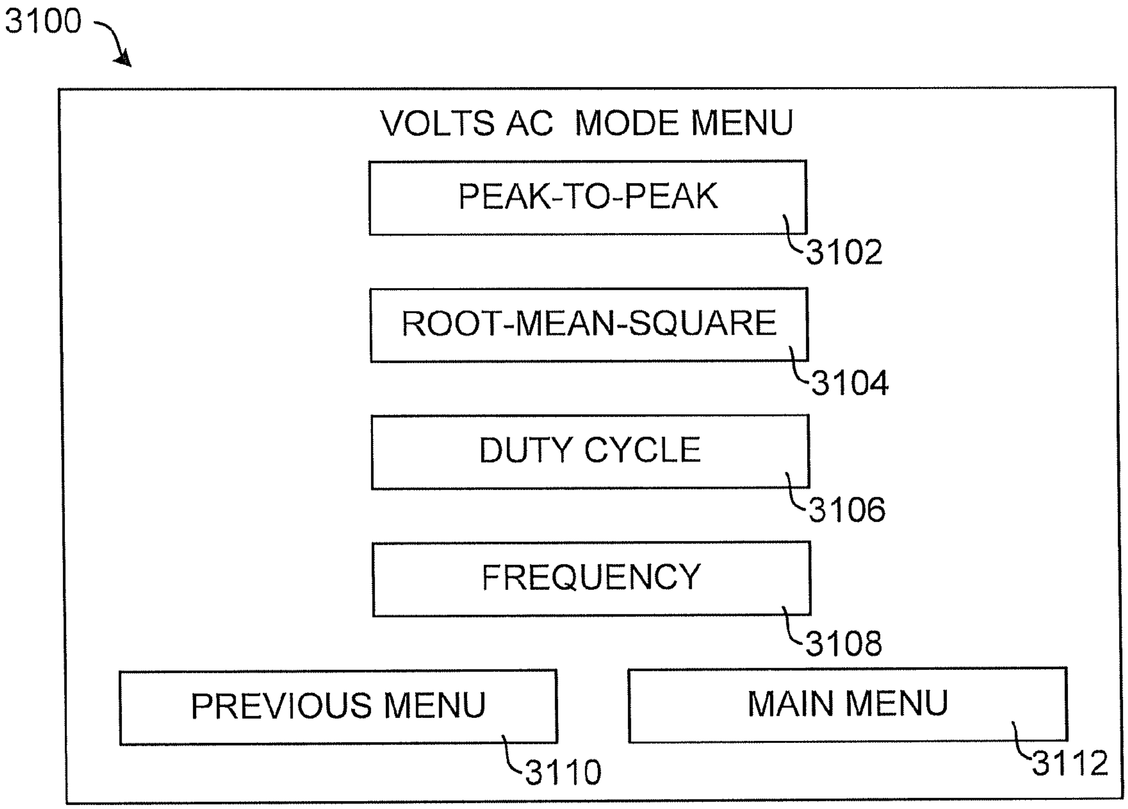

Menu data 216 comprises data that can be visually presented via display 300. FIG. 29 through FIG. 31 illustrate examples of menu data 216 displayable on display 300. Each of those figures illustrates a respective menu (i.e., main menu 2900, scope/multimeter menu 3000, and Volts AC mode menu 3100). Each respective menu may comprise one or more menu items that is/are selectable by a user. Selection of a menu item can cause display 300 to display instruction data 218. Additionally or alternatively, selection of a menu item can cause wireless transceiver 202 to transmit instruction data 218 to a remote device (e.g., DAQ device 104 or vehicle scanner 106) as payload of a message, such as data-share message 3500 illustrated in FIG. 35 or to transmit a mode-selection command to the remote device, such as mode-selection command 3400 illustrated in FIG. 34.

As an example, starting at FIG. 29, a user may select menu item 2908 by touching display 300 where menu item 2908 is being displayed. In response to selecting menu item 2908, scope/multimeter menu 3000 (shown in FIG. 30) may be visually presented on display 300. A user may select menu item 3006 where menu item 3006 is being displayed. In response to selecting menu item 3006, Volts AC mode menu 3100 (shown in FIG. 31) may be visually presented on display 300.

CRPI 212 may comprise program instructions that are executable as an operating system that provides for direct control and management of hardware components (e.g., processor 204 and data storage device 208) of display device 108. The operating system can manage execution of other program instructions within CRPI 212. As an example, the operating system may comprise the Windows XP Embedded (XPe) operating system available from Microsoft Corporation, Redmond, Wash., United States, or some other operating system.

CRPI 212 may comprise program instructions that are executable by processor 204 to cause display 300 to display menu data 216 or instruction data 218. Displaying menu data 216 may include displaying a list of data-acquisition modes of DAQ device 104 or a list of data-acquisition modes of vehicle scanner 106.

CRPI 212 may comprise program instructions that are executable by processor 204 to identify a desired mode of a remote device (e.g., DAQ device 104 or vehicle scanner 106) selected from a list of data-acquisition modes displayed on display 300. The list of data-acquisition modes may be stored within menu data 216. User interface 200 may be used to select the desired mode from the displayed list of data-acquisition modes while the remote device is operating in a mode different than the desired mode.

CRPI 212 may comprise program instructions that are executable by processor 204 to generate a mode-selection command (e.g., mode selection command 3400) and to cause wireless transceiver 202 to transmit the mode-selection command via wireless network 110. Those program instructions may be executed in response to processor 204 identifying a desired mode selected from the displayed list of data-acquisition modes.

Next, FIG. 3 illustrates a front view of an example embodiment of display device 108. FIG. 3 further illustrates that display device 108 includes display 300, a microphone 302 for receiving audible data (e.g., voice data generated by a user of display device 108 or sounds generated by a motor vehicle), a status indicator 304 (e.g., a light emitting diode (LED)), and user controls 306. The voice data may include voice commands for making a mode-selection from a menu displayed on display 300. A microphone symbol is located above microphone 302 and a data storage device symbol is located above status indicator 304.

Display 300 may comprise a liquid crystal display (LCD), a plasma display, or some other type of display. Display 300 is operable to visually present (e.g., display) data to a user. Display 300 may visually present data using numbers, letters, punctuation marks, pictures, graphs, waveforms, or some other visually presentable form of data. The data visually presentable and/or presented at display 300 may include locally-acquired data (LAD), such as menu data 216 and a cursor that can be moved between menu items of menu data 216. The data visually presentable and/or presented at display 300 may include remotely-acquired data (RAD), such as data acquired via wireless transceiver 202 or wired interface 206.

Display 300 may comprise a touch screen that can detect the presence and location of a touch within its display area. The various menu items of a displayed menu may be selected via the touch screen.

User controls 306 are operable to enter a user-selection. User controls 306 may be arranged in various ways. In that regard, user controls 306 may be arranged to include a keypad, rotary switches, push buttons, or some other means to enter a user-selection. In the example embodiment illustrated in FIG. 3, user controls 306 include a power button 308, a brightness button 310, a keyboard button 312, a camera button 314, a cursor left button 316, a cursor right button 318, a cursor up button 320, a cursor down button 322, a menu item selection button 324, and a quick access button 326. Table 1 lists example user-selections that can be entered by pushing or pushing and releasing a user control of user controls 306. Other examples of user controls 306 and other examples of the user-selections are also possible.

TABLE 1

| User Control | Example User-selections |
|---|---|
| Power button 308 | Turn display device 108 power on or off. |
| Brightness button 310 | Increase or decrease a brightness of display 300. Display a brightness menu at display 300. |
| Keyboard button 312 | Display keyboard at display 300. Remove keyboard being displayed at display 300. |
| Camera button 314 | Activate camera shutter to capture an image |
| Cursor left button 316 | Move a cursor, displayed at display 300, to the left |
| Cursor right button 318 | Move a cursor, displayed at display 300, to the right |
| Cursor up button 320 | Move a cursor, displayed at display 300, upward |
| Cursor down button 322 | Move a cursor, displayed at display 300, downward |
| Menu item selection button 324 | Select a menu item from displayed menu data 216. |
| Quick access button 326 | Select a function that pertains to a current operating mode of display device 108. |

Next, FIG. 4 illustrates a back view of an example embodiment of display device 108. FIG. 4 further illustrates that display device 108 includes (i) a stylus 400 that is operable to enter a user selection by touching display 300, (ii) a camera shutter 402, (iii) a camera flashing device 404, (iv) a lock slot 406, and (v) a device stand 408. Stylus 400 may be removed from a back side of display device 108 when a user desires to use stylus 400 to touch the touch screen of display 300, and stylus 400 may be reinserted into the back side of display device 108 when stylus 400 is not being used. Lock slot 406 may comprise a slot arranged to receive a Kensington (anti-theft) lock available from Kensington Computer Products Group, Redwood Shores, Calif., United States.

Display device 108 may include a camera that is operable to capture images. The camera may include camera shutter 402 and camera flashing device 404. Camera button 314 may be used to activate (e.g., open and then close) camera shutter 402. Camera flashing device 404 is operable to provide illumination at the time an image is being captured by the camera.

Device stand 408 is operable to position display 300 at a desired viewing position (e.g., a desired viewing angle). Device stand 408 may include a lower end 410, and upper ends 412 that are rotatable about fixed points of display device 108. As upper ends 412 rotate about the fixed points, lower end 410 is moved closer to or farther away from display device 108.

Next, FIG. 5 illustrates a right-side view of an example embodiment of display device 108. FIG. 5 further illustrates that display device 108 includes a card slot 500 and a port 502. Card slot 500 is operable to retain a data storage card, and card slot 500 allows for installation and removal of the data storage card. The data storage card may, for example, comprise a Compact Flash card, an SD memory card, a mini SD memory card, an xD picture card, or some other type of data storage card. The data storage card may be a portion of data storage device 208 or may be data storage in addition to data storage device 208. Port 502 may comprise a USB port of wired interface 206. Port 502 may be operable to connect to a USB cable.

Next, FIG. 6 illustrates a left-side view of an example embodiment of display device 108. FIG. 6 further illustrates that display device 108 includes ports 600, 602, 604, and 606. Those ports may be a part of wired interface 206. Port 600 may comprise one or more USB ports. Each USB port of port 600 may connect to a first end of a respective USB cable. A second end of a USB cable connected to port 600 may connect to USB port 2400 (shown in FIG. 24) or to a USB port at another device, such as a device connected to network 116. Port 602 may comprise an audio output port that is connectable to one or more loud speakers, a set of ear buds, a set of head phones, or some other device that is operable to convert electrical signals generated by display device 108 to sound waves that can be heard by a user. Port 604 may comprise an audio input port that is connectable to a microphone that converts sound waves received at the microphone to electrical signals. Port 606 may comprise a power port that is connectable to a power source that provides electrical power for operation of at least a portion of display device 108 and/or to charge a rechargeable battery within display device 108.

Figure 7:
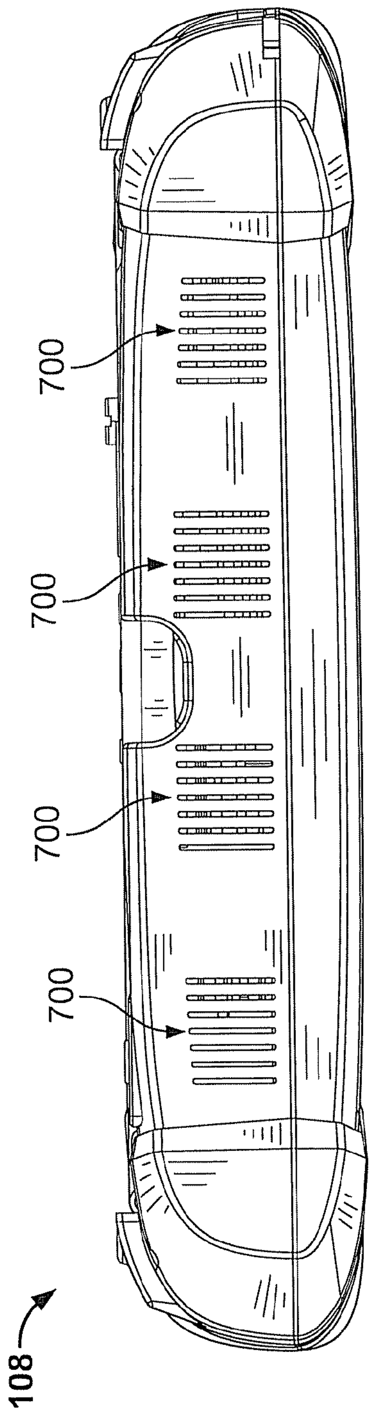

Next, FIG. 7 illustrates a top view of an example embodiment of display device 108. FIG. 7 further illustrates that display device 108 may include venting slots 700. Venting slots 700 may be used for ventilation purposes so that an operating temperature of display device 108 remains below a threshold operating temperature.

Figure 8:
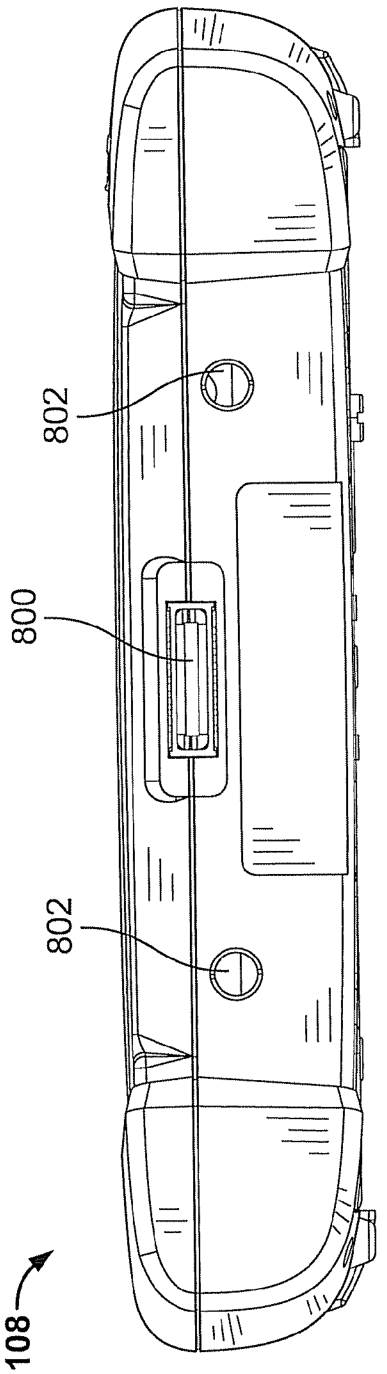

Next, FIG. 8 illustrates a bottom view of an example embodiment of display device 108. FIG. 8 further illustrates that display device 108 includes connector 800 and guides 802. Display device 108 may be attached to and removed from a docking station (not shown) that includes a mating connector and guide pins. During attachment of display device 108 to the docking station, the guide pins may enter into guides 802 so as to allow connector 800 to connect to the mating connector of the docking station. The docking station may be connected to a secondary display having a larger viewing area then display 300. Display device 108 can provide data received via wireless transceiver 202 and other data to the docking station for subsequent viewing of that data on the secondary display. The docking station may be connected to network 116 and the docking station may operate as an interface that connects display device 108 to network 116. The docking station may provide power to display device 108 (e.g., to charge a battery within display device 108) when display device 108 is attached to the docking station.

Next, FIG. 9 illustrates a block diagram of DAQ device 104, and FIG. 10 to FIG. 15 illustrate details of an example embodiment of DAQ device 104. As illustrated in FIG. 9, DAQ device 104 includes a user interface 900, a wireless transceiver 902, a processor 904, an input element 906, and a data storage device 908, all of which may be linked together via a system bus, network, or other connection mechanism 910.

Figure 10:
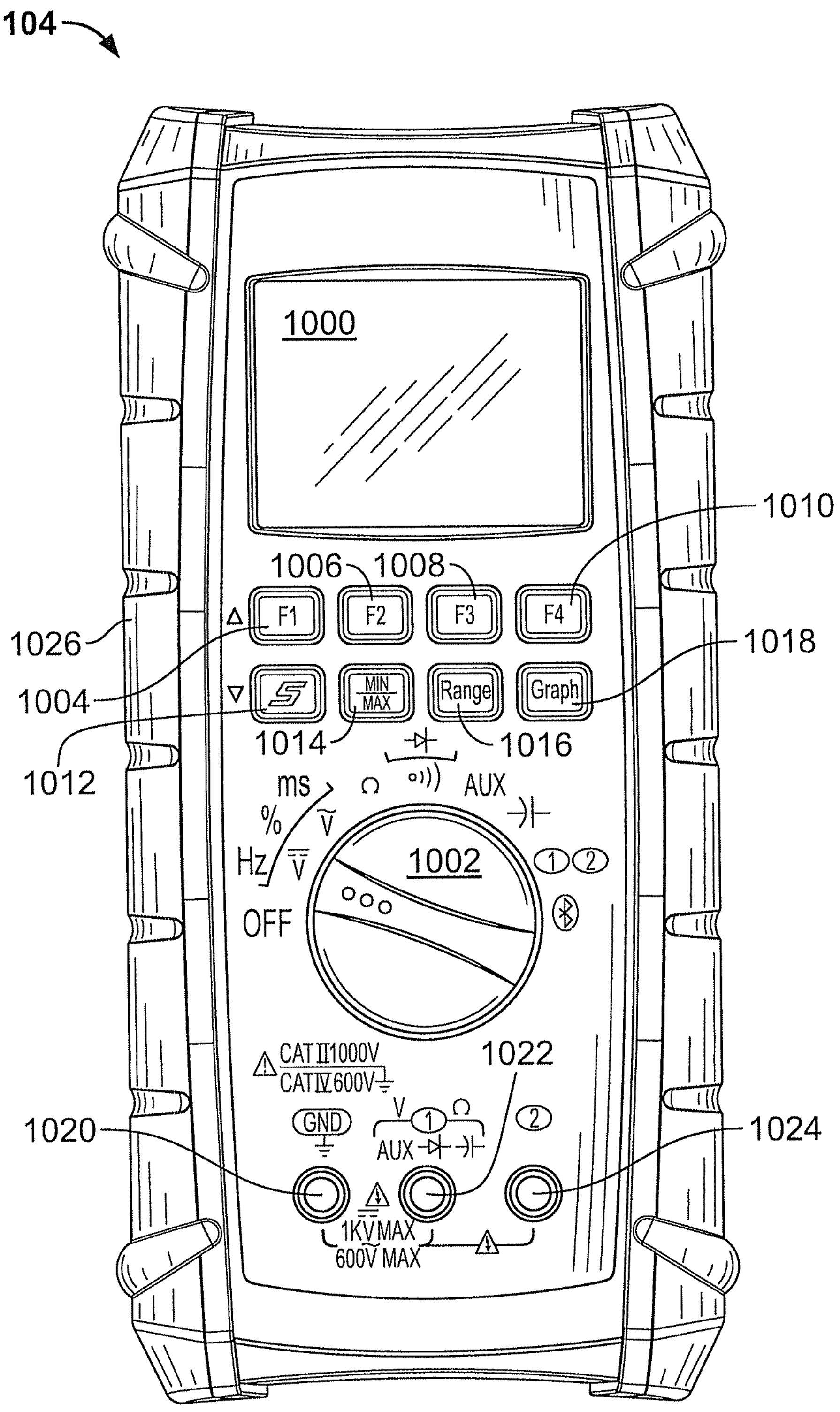
FIG. 10 to FIG. 15 illustrate various views of an example embodiment of the DAQ device of FIG. 9.

User interface 900 is operable to present data to a user and to enter user inputs (e.g., user selections such as mode selections, sub-mode selections, a remote-control mode selection, and a local-control mode selection). User interface 900 may include a display 1000 (shown in FIG. 10). Display 1000 is operable to visually present data, such as data obtained and/or generated by input element 906, data obtained via wireless transceiver 902, and/or data contained in data storage device 908. User interface 900 may include a selector device for selecting one or more modes and/or sub-modes of DAQ device 104 and for selecting between a local-control mode and a remote-control mode of DAQ device 104. Example selector devices 1002, 1004, 1006, 1008, 1010, 1012, 1014, 1016, and 1018 are illustrated in FIG. 10.

Wireless transceiver 902 may comprise a single wireless transceiver that is operable to carry out communications via wireless network 110. Wireless transceiver 902 may carry out communications with vehicle scanner 106, display device 108, and/or some other device that is operating to communicate via wireless network 110. As an example, wireless transceiver 902 may comprise a Bluetooth transceiver, a Wi-Fi transceiver, or some other type of wireless transceiver.

Alternatively, wireless transceiver 902 may comprise multiple wireless transceivers. For example, wireless transceiver 902 may comprise two wireless transceivers that communicate according to a common air interface protocol or different air interface protocols. Those air interface protocols may be selected from a Bluetooth air interface protocol, a Wi-Fi air interface protocol, and some other air interface protocol. In accordance with an embodiment in which wireless transceiver includes two transceivers, a Bluetooth transceiver may communicate with vehicle scanner 106 and/or display device 108 via a Bluetooth network of wireless network 110, and a Wi-Fi transceiver may communicate with vehicle scanner 106 and/or display device 108 via a Wi-Fi network of wireless network 110.

As another example, wireless transceiver 902 may include three or more wireless transceivers. In accordance with an embodiment in which wireless transceiver 902 includes three or more wireless transceivers, two or more of the wireless transceivers may communicate according to a common air interface protocol or different air interface protocols.

Processor 904 may comprise one or more general purpose processors (e.g., INTEL microprocessors) and/or one or more special purpose processors (e.g., digital signal processors). Processor 904 may execute computer-readable program instructions (CRPI) 918 that are contained in computer-readable data storage device 908.

Input element 906 may include input leads 912, an input signal processing element 914 that is operable to convert input signals obtained via input leads 912 into input data (e.g., generate input data), and packet element 916. Input leads 912 may include one or more input leads, each of which can receive input signals from an input signal acquisition point. The input signal acquisition point may comprise any of a variety of locations at which an input signal can be acquired. In accordance with an example in which device-under-service 102 comprises an automobile, the input signal acquisition point may comprise a location on the automobile at which a voltage signal, current signal, air pressure signal, air temperature signal, oil pressure signal, oil temperature signal, or some other input signal can be acquired.

Each input lead 912 may include a first end and a second end. The first end of each input lead 912 may be inserted into or otherwise attached to DAQ device 104. The first end of each input lead may comprise a banana plug. The second end of each input lead 912 may be arranged in any of a variety of configurations. As an example, a configuration of the second end may comprise a configuration that includes (i) an alligator clip, such as an MTA85 alligator clip sold by Snap-on Incorporated, Kenosha, Wis., United States, (ii) a spring hook, such as an MTA80 spring hook sold by Snap-on Incorporated, (iii) a test probe, such as an MTA20 test probe sold by Snap-on Incorporated, or (iv) a backprobe, such as an MTTL7005 backprobe sold by Snap-on Incorporated. Other example configurations of the second end of an input lead 912 are also possible.

Figure 36:
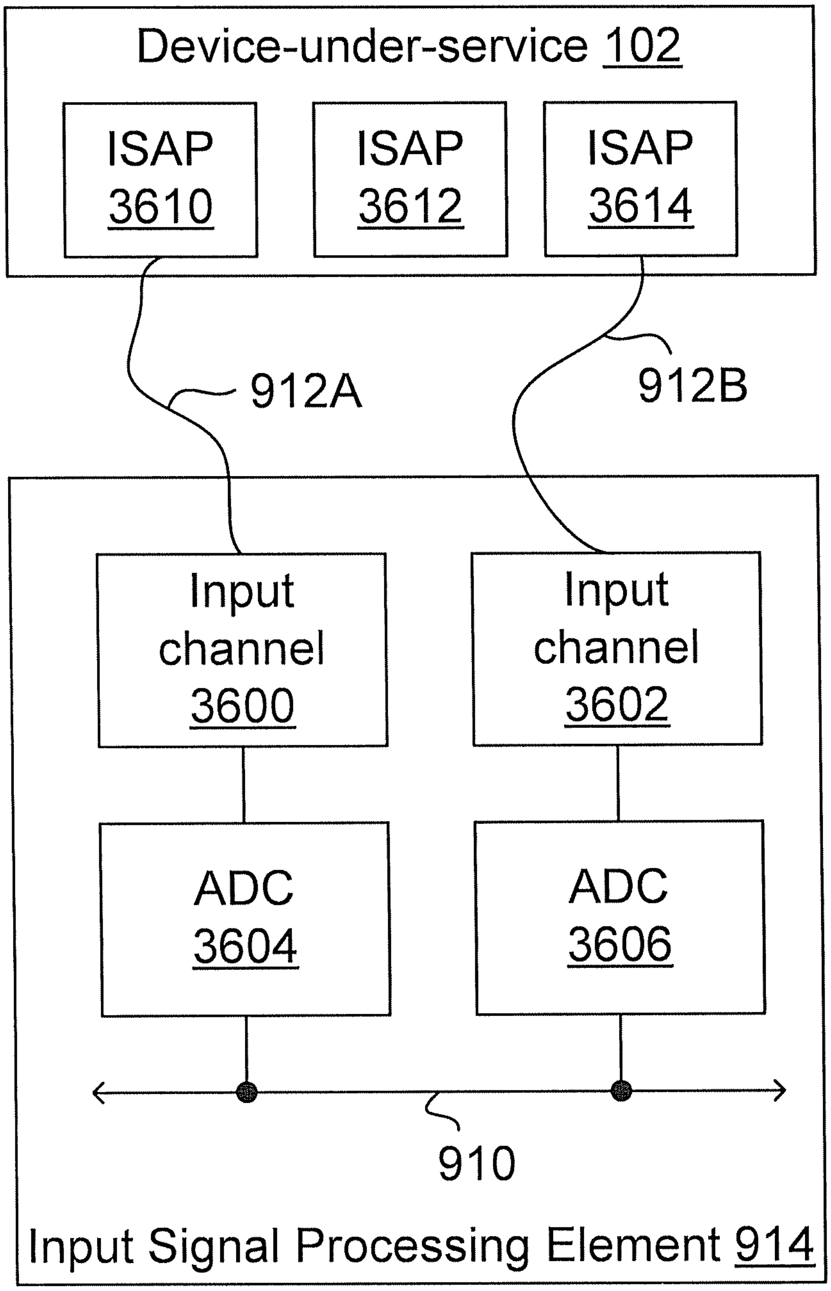
FIG. 36 is a block diagram illustrating details of the system shown in FIG. 1.

Input element 906 may include an input signal processing element 914 that is operable to convert an input signal received via one or more input leads 912 into input data that is displayable at display 1000. Each of those input signals may, for example, comprise analog electrical signals. FIG. 36 is a block diagram illustrating details of input signal processing element 914, examples of input leads 912, and details of device-under-service 102. As shown in FIG. 36, input signal processing element 914 includes input channels 3600 and 3602, analog-to-digital converter (ADC) 3604, and ADC 3606. Input channel 3600 may be associated with port 1022 (shown in FIG. 10) and input channel 3602 may be associated with port 1024 (shown in FIG. 10). The input channels may be operational when selector device 1002 is in a position such that DAQ device 104 operates in an oscilloscope mode. In an alternative embodiment, input signal processing element 914 may include only one input channel or more than two input channels. Digital outputs of ADC 3604 and 3606 may be transferred to another element of DAQ device 104 (e.g., user interface 900, processor 904, data storage 908, or packet element 916) via connection mechanism 910.

Device-under-service 102 may comprise a plurality of input signal acquisition points (ISAP). As shown in FIG. 36, device-under-service 102 comprises ISAP 3610, 3612, and 3614. Each ISAP may comprise a point at which an input signal can be acquired, such as a point comprising a terminal within an electrical connector, a point within a wiring harness carrying electrical signals, a battery lead, or some other point within device-under-service 102. Input leads 912 may include input lead 912A and input lead 912B. Input leads 912A and 912B can be connected to and removed from any of the various ISAP within device-under-service 102.

Returning to FIG. 9, packet-element 916 is operable to packetize the input data (e.g., place the input data into data packets) so as to generate data packets containing the input data. Packet-element 916 may provide the data packets to wireless transceiver 902 via connection mechanism 910 for subsequent transmission of the data packets via an air interface. In an alternative embodiment, processor 904 or some other portion of DAQ device 104 can comprise packet-element 916 or carry out the functions of packet-element 916. The data packets containing the input data may be carried as the payload of a data message 3500 (shown in FIG. 35).

Data storage device 908 may comprise a computer-readable storage medium readable by processor 904. The computer-readable storage medium may comprise volatile and/or non-volatile storage components, such as optical, magnetic, organic or other memory or disc storage, which can be integrated in whole or in part with processor 904. Data storage device 908 may contain various computer-readable data, such as CRPI 918, remote device data 920, input data 922, and instruction data 924.

Remote device data 920 may include data associated with a device that is arranged to communicate with DAQ device 104 via wireless network 110. For example, remote device data 920 may include data associated with display device 108, such as a radio identifier and password associated with display device 108. The data associated with display device 108 may be received at DAQ device 104, for storing as remote device data 920, during a pairing process carried out between display device 108 and DAQ device 104. The pairing process between DAQ device 104 and display device 108 may include DAQ device 104 providing display device 108 with the data (e.g., a passkey) associated with DAQ device 104 and display device 108 providing DAQ device 104 with data (e.g., a passkey) associated with display device 108. After carrying out that paring process with display device 108, DAQ device 104 may use the remote device data 920 when establishing communication network 110 with display device 108.

Remote device data 920 is not limited to data associated with one remote device. In that regard, remote device data 920 may include respective data associated with each of a plurality of devices operable to communicate via wireless network 110, such as data associated with display device 108, and data associated with vehicle scanner 106. The data associated with vehicle scanner 106 may include a radio identifier and password associated with vehicle scanner 106. The data associated with vehicle scanner 106 may be received at DAQ device 104, for storing as remote device data 920, during a pairing process carried out between DAQ device 104 and vehicle scanner 106. The pairing process between DAQ device 104 and vehicle scanner 106 may include vehicle scanner 106 providing DAQ device 104 with the data associated with vehicle scanner 106 and DAQ device 104 providing vehicle scanner 106 with data associated with DAQ device 104. After carrying out the paring process with vehicle scanner 106, DAQ device 104 may use the remote device data 920 when establishing wireless network 110 to communicate with vehicle scanner 106.

Input data 922 may comprise data generated by input signal processing element 914. A portion of data storage device 908 that contains input data 922 may function as a buffer. Once the buffer is filled with data, the first data stored in the buffer may be the first data overwritten such that the buffer follows a first-in-first-out (FIFO) process. Use of a selector device on DAQ device 104 may cause DAQ device 104 to enter a mode in which at least a portion of input data 922 is not overwritten by new input data. During this mode, the portion of the input data 922 not being overwritten can be displayed via display 1000 at the same time the new input data is being displayed via display 1000. Use of a selector device on DAQ device 104 may cause DAQ device 104 to exit the mode in which at least a portion of input data 922 is not overwritten by new input data.

Instruction data 924 may comprise data that identifies how to connect a portion of the DAQ device 104 to device-under-service 102, how to operate device-under-service 102 (e.g., which position selector device 1002 should be turned to or which selector device of selector devices 1004-1008 should be pushed), inspections to carry out on device-under-service 102, or some other instruction data. Instruction data 924 may comprise various data including numbers, letters, punctuation marks, pictures, graphs, waveforms, or some other visually presentable form of data.

CRPI 918 may include program instructions (referred to herein as PI-918-A) that are executable to cause DAQ device 104 to transition from a local-control mode to a remote-control mode. Processor 904 may execute PI-918-A in response to selector device 1002 changing from a position associated with a DAQ mode that is selected via selector device 1002 to a position associated with the remote-control mode. Alternatively, processor may execute PI-918-A in response to engaging a selector device (e.g., selector device 1004) or by a changing a selector device from a local-control mode position to a remote-control mode position. Execution of PI-918-A may cause a transceiver or transceivers of wireless transceiver 902 to transition from a transceiver-off state to a transceiver-on state.

CRPI 918 may include program instructions (referred to herein as PI-918-B) that are executable to change an operating state of wireless transceiver 902 from a remote-control mode to a local-control mode. Processor 904 may execute PI-918-B in response to selector device 1002 changing from position associated with the remote-control mode to a position associated with a DAQ mode that is selected via selector device 1002. Alternatively, processor may execute PI-918-B in response to engaging a selector device (e.g., selector device 1004) or by changing a selector device from a remote-control mode position to a local-control mode position. Execution of PI-918-B may cause a transceiver or transceivers of wireless transceiver 902 to transition from a transceiver-on state to a transceiver-off state.

CRPI 918 may include program instructions (referred to herein as PI-918-C) that are executable to determine a desired mode for DAQ device 104 from mode-selection command 3400. If DAQ device 104 is operating in the mode identified in mode-selection command 3400, execution of PI-918-C allows DAQ device 104 to continue operating in the desired mode. On the other hand, if DAQ device 104 is operating in a mode different than the mode identified in mode-selection command 3400 (i.e., a non-desired mode), execution of PI-918-C causes DAQ device 104 to transition from operating in the non-desired mode to the desired mode.

CRPI 918 may include program instructions (referred to herein as PI-918-D) that are executable to cause display 1000 to display instruction data 924. In one respect, execution of PI-918-D may cause display 1000 to display instruction data 924 so as to guide a user in connecting input leads 912 to device-under-service 102. In another respect, execution of PI-918-D may cause display 1000 to display instruction data (such as instruction data 218) that is received as payload in data-share message 3500.

CRPI 918 may include program instructions (referred to herein as PI-918-E) that are executable to cause input data generated by input element 906 to be transmitted to wireless network 110 for transmission, in turn, to display device 108. The input data may be packetized by packet element 916 prior to being transmitted. Wireless transceiver 902 transmits the input data to wireless network 110, and may do so using messages arranged like data-share message 3500 or some other message.

Next, FIG. 10 illustrates a front view of an example embodiment of DAQ device 104, and in particular, elements of user interface 900 and input element 906. The elements of user interface 900 may include display 1000 and selector devices 1002, 1004, 1006, 1008, 1010, 1012, 1014, 1016, and 1018. For purposes of this description, "selector devices 1004-1018" refers to selector devices 1004, 1006, 1008, 1010, 1012, 1014, 1016, and 1018. FIG. 10 also illustrates (i) ports 1020, 1022, and 1024, which are part of input element 906, and (ii) a grip 1026 that provides DAQ device 104 with shock protection in the event that DAQ device 104 is dropped or struck.

Display 1000 may comprise a liquid crystal display (LCD), a plasma display, or some other type of display. Display 1000 is operable to visually present (e.g., display) data to a user. Display 1000 may visually present data using numbers, letters, punctuation marks, pictures, graphs, waveforms, or some other visually presentable form of data. The data visually presentable and/or presented at display 1000 may include locally-acquired data (LAD), such as data acquired via input element 906 (e.g., via input leads 912) and/or data contained in data storage device 908. The data visually presentable and/or presented at display 1000 may include remotely-acquired data (RAD), such as data acquired via wireless transceiver 902.

Selector device 1002 comprises a switch having multiple positions. As illustrated in FIG. 10, selector device 1002 comprises a rotary switch having nine positions, but selector device 1002 is not so limited. Each position of selector device 1002 is associated with an off mode or one or more data acquisition modes, and each position of selector device 1002 is associated with one or more symbols to identify the mode (s) associated with that position. Furthermore, each position of selector device 1002 may be associated with a local-control mode (e.g., a mode in which the off mode or data acquisition mode is selected by selector device 1002) or a remote-control mode (e.g., a mode in which a data acquisition mode is selected by display device 108).

Table 2 provides an example list of modes associated with each position of selector device 1002, and an example list of whether each position is associated with a local-control mode or a remote-control mode.

TABLE 2

| Position of selector device 1002 | Mode Control Type | Mode |
|---|---|---|
| Position 1 | Local-Control Mode | Off mode |
| Position 2 | Local-Control Mode | Volts DC mode |
| Position 3 | Local-Control Mode | Volts AC mode |
| Position 4 | Local-Control Mode | Resistance mode |
| Position 5 | Local-Control Mode | Diode/Continuity mode |
| Position 6 | Local-Control Mode | Auxiliary mode |
| Position 7 | Local-Control Mode | Capacitance mode |
| Position 8 | Local-Control Mode | Oscilloscope mode |
| Position 9 | Remote-Control Mode | DAQ mode selected via display device 108 |

Position 1 is associated with the symbol "OFF." The position numbers increase in a clockwise direction. The three circles on selector device 1002 are closest to a currently-selected position. In FIG. 10, position 2 is the currently-selected position.

Selector device 1002 may be turned to each of the nine positions. Turning selector device 1002 from a first position (not necessarily position 1) to a second position (not necessarily position 2) can cause DAQ device 104 to transition from a first DAQ mode that is associated with the first position to a second DAQ mode that is associated with the second position. Transitioning from the first DAQ mode to the second DAQ mode may be carried out, at least in part, by processor 904 executing program instructions of CRPI 918.

While selector device 1002 is positioned at a position corresponding to a remote-control mode (e.g., position 9), wireless transceiver 902 may receive a mode-selection command transmitted from display device 108. The mode-selection command may be received in response to wireless transceiver 902 transmitting to display device 108 a request for a mode-selection command. The mode-selection command received at wireless transceiver 902 may be arranged as mode-selection command 3400 illustrated in FIG. 34. Mode-selection command 3400 may include a mode field 3406 that identifies a DAQ mode selected via display device 108. The DAQ mode selected via display device 108 may comprise a mode that is also selectable via DAQ device 104. Mode field 3406 may identify a sub-mode selected via display device 108. The sub-mode selected via display device 108 may comprise a sub-mode that is also selectable via one of selector devices 1004-1018 when selector device 1002 is in a local-control mode position. Table 3 identifies example modes and sub-modes that can be identified in mode field 3406.

TABLE 3

| Position of selector device 1002 | Mode | Sub-mode |
|---|---|---|
| 9 | Volts DC mode | Range: 0-2 Volts, 0-20 Volts, 0-200 Volts |
| 9 | Volts AC mode | Range: 0-2 Volts, 0-20 Volts, 0-200 Volts |
| 9 | Resistance mode | Range: 0-40 ohms, 0-400 ohms, 0-4K ohms, 0-40K ohms, 0-400K ohms |
| 9 | Diode/Continuity mode | N.A. |
| 9 | Auxiliary mode | Temperature mode, vacuum mode, air pressure mode, oil pressure mode, or current mode |
| 9 | Capacitance mode | Range: 0-4 μFarad (F), 0-40 μF, 0-400 μF |
| 9 | Oscilloscope mode | Trigger: Positive Edge, Negative Edge Channel: 1, 2, 1 and 2 |

The sub-modes associated with each mode identify additional settings for DAQ device 104. DAQ device 104 can use sub-mode information contained within mode-selection command 3400 to configure the selected mode identified in the mode-selection command 3400. For instance, if mode-selection command 3400 identifies the mode as Volts DC mode and a range of 0-20 Volts and if DAQ device 104 is not currently configured to operate in that mode and sub-mode, DAQ device 104 reconfigures itself to operate in the Volts DC mode with a range of 0-20 Volts. A subsequent mode-selection command could be sent with the same mode as a previous mode, but with different sub-mode information (e.g., 0-2 Volts or 0-200 Volts). Upon receiving that subsequent mode-selection command, DAQ device 104 reconfigures itself to operate in the same mode but with the different sub-mode.

Selector devices 1004-1018 may each comprise a respective push button, but selector devices 1004-1018 are not so limited. Each selector device of selector devices 1004-1018 may be pushed or pushed and released to enter a user input that triggers a function, associated with that selector device, to be initiated and/or carried out. Hereinafter in this description, pushing a selector device refers to pushing a selector device or pushing and releasing a selector device. Selector device 1018 may be pushed to cause display 1000 to visually present input data as a histogram.

One or more of selector devices 1004-1018 may be associated with multiple modes multiple sub-modes, and or functions. For example, selector devices 1004, 1006, 1008, and 1110 may be associated with a respective first sub-mode while selector device 1002 is positioned at position 2 and may be associated with a respective second sub-mode while selector device 1002 is positioned at a position other than position 1 or position 2.

The function associated with each selector device of selector devices 1004-1018 may be dependent upon the position of selector device 1002. As an example, when selector device 1002 is in position 8 and DAQ device 104 is operating in the oscilloscope mode, selector device 1004 may be pushed to enter a user input that causes an input signal at an input channel to be tagged as a historical waveform to be displayed for that input channel, and selector device 1006 may pushed to enter a user input that causes an input signal at another input channel to be tagged as a historical waveform to be displayed for that other input channel. When selector device 1002 is in positions other than position 8, pushing selector device 1004 and 1006 may trigger other functions to be carried out.

One or more of selector devices 1004-1018 may be associated with a remote-control mode. For instance, selector device 1004 may associated with a remote-control mode. In that regard, pushing selector device 1004 may cause DAQ device 104 to transition from a local-control mode to a remote-control mode in the same way as if selector device 1002 is moved to position 9. Pushing that same selector device or another selector device, while DAQ device 104 operates in the remote-control mode, may cause DAQ device 104 to transition from the remote-control mode to a local-control mode in the same way as if selector device 1002 is moved from position 9 to another position.

Ports 1020, 1022, and 1024 are operable to receive a respective input lead of input leads 912. Each input lead can include first and second ends. The first end of an input lead may comprise a banana plug. Ports 1020, 1022, and 1024 may include a respective female banana plug receptacle for receiving the banana plug of an input lead. The second end of each input lead may include an alligator clip, a quick-attach probe, or some other device for contacting an input signal acquisition point.

Figure 11:
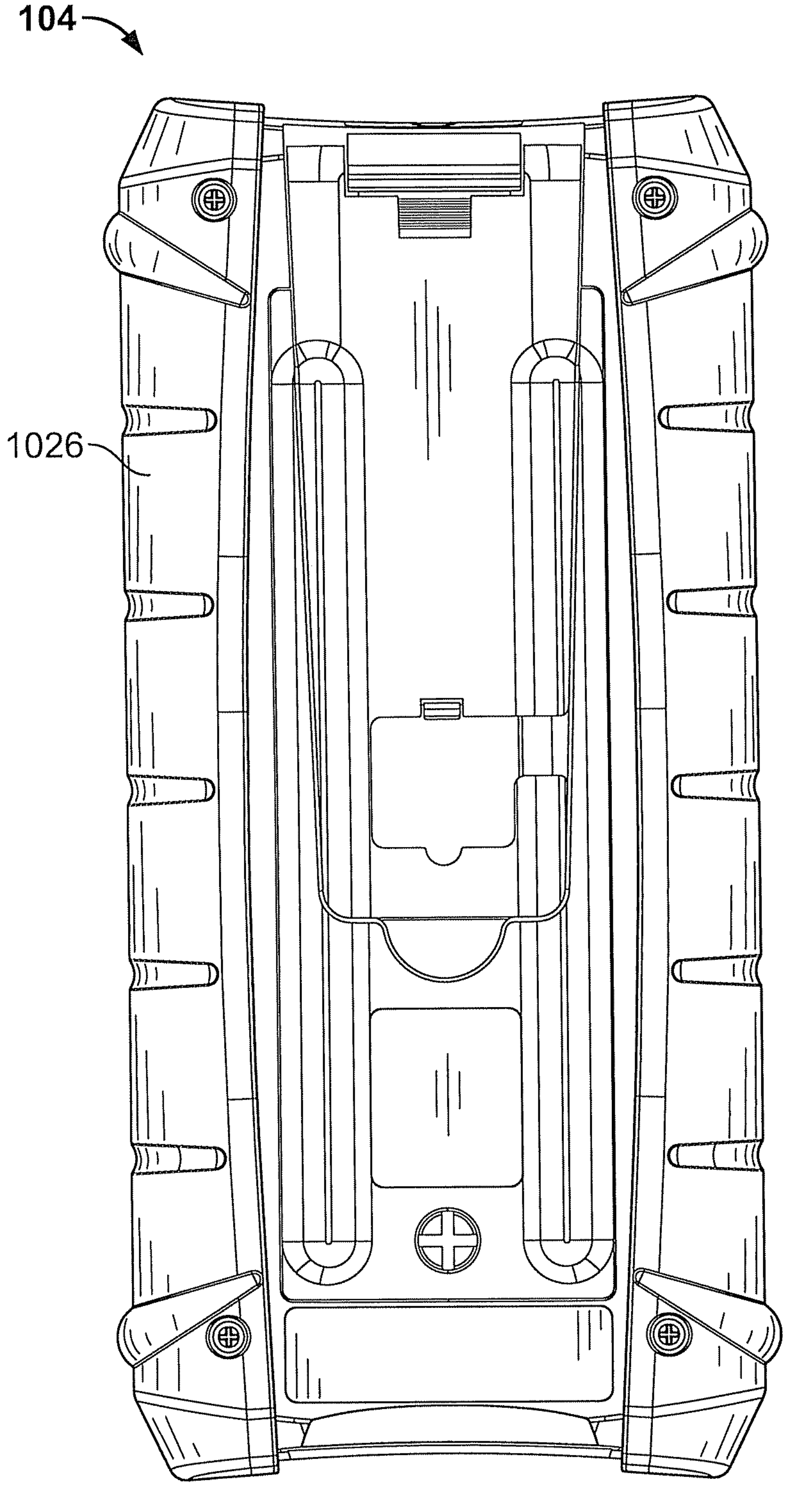
Figure 12:
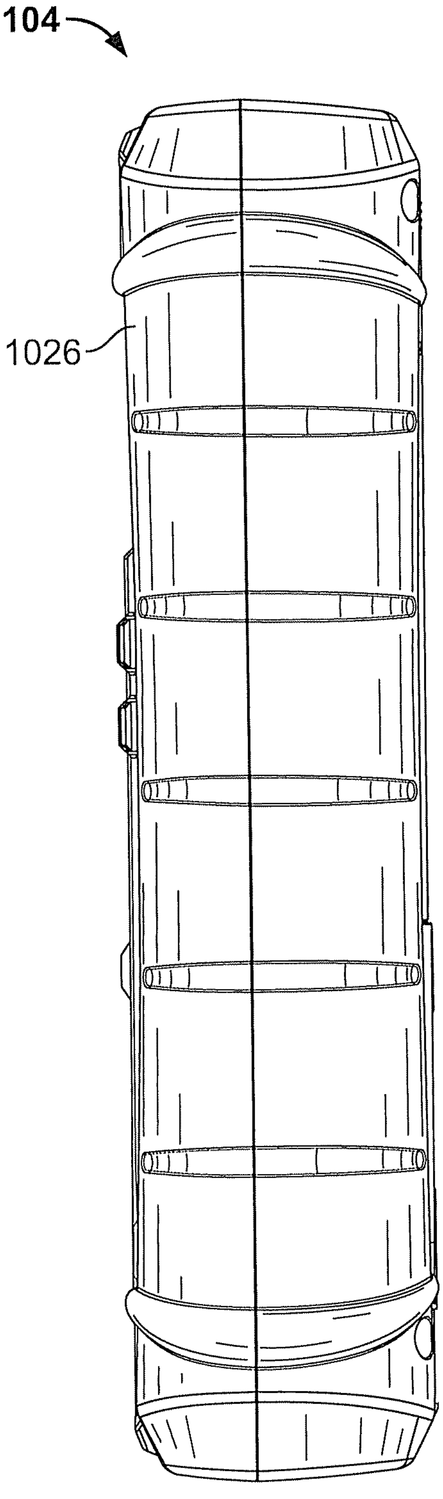
Figure 13:
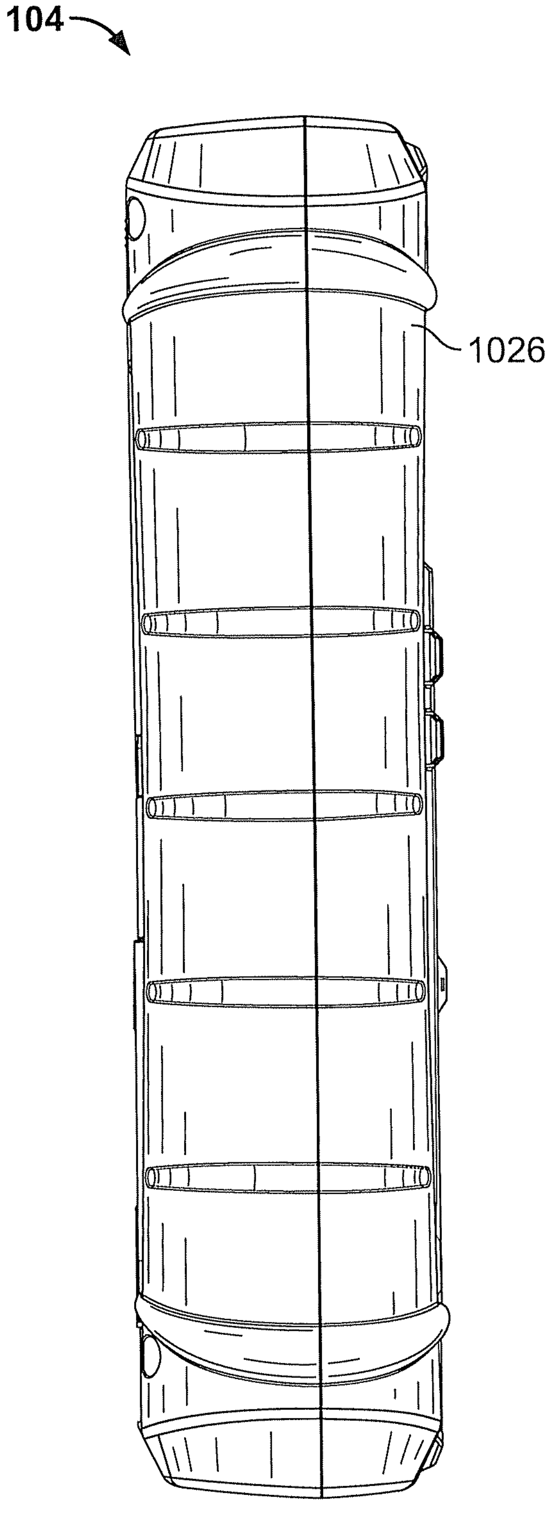
Figure 14:
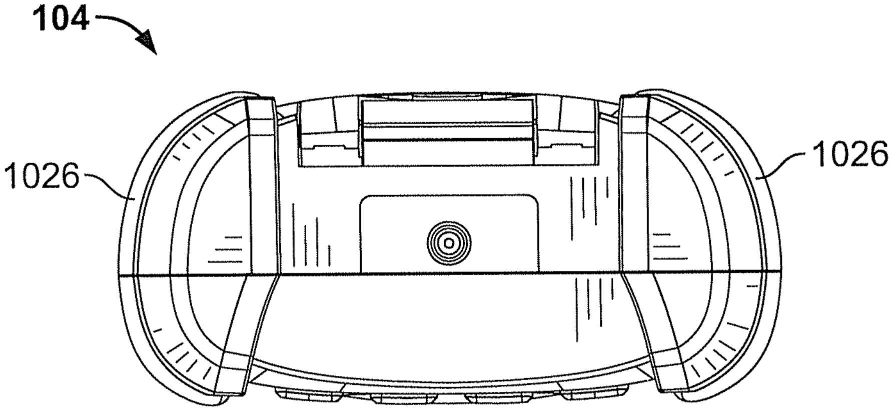
Figure 15:
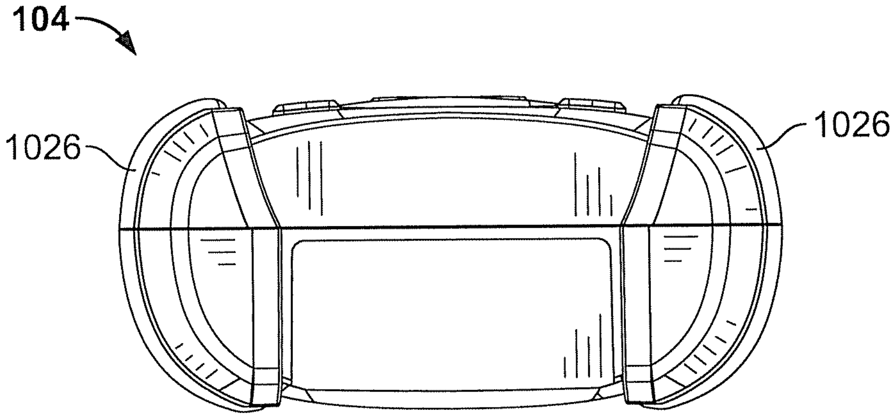

Next, FIG. 11 illustrates a back view of an example embodiment of DAQ device 104. FIG. 12 illustrates a right-side view of an example embodiment of DAQ device 104. FIG. 13 illustrates a left-side view of an example embodiment of DAQ device 104. FIG. 14 illustrates a top view of an example embodiment of DAQ device 104. FIG. 15 illustrates a bottom view of an example embodiment of DAQ device 104. FIG. 11 to FIG. 15 each illustrate respective portions of grip 1026. Grip 1026 may be made from rubber. As an example, grip 1026 may be arranged as a single piece of rubber.

Figure 16:
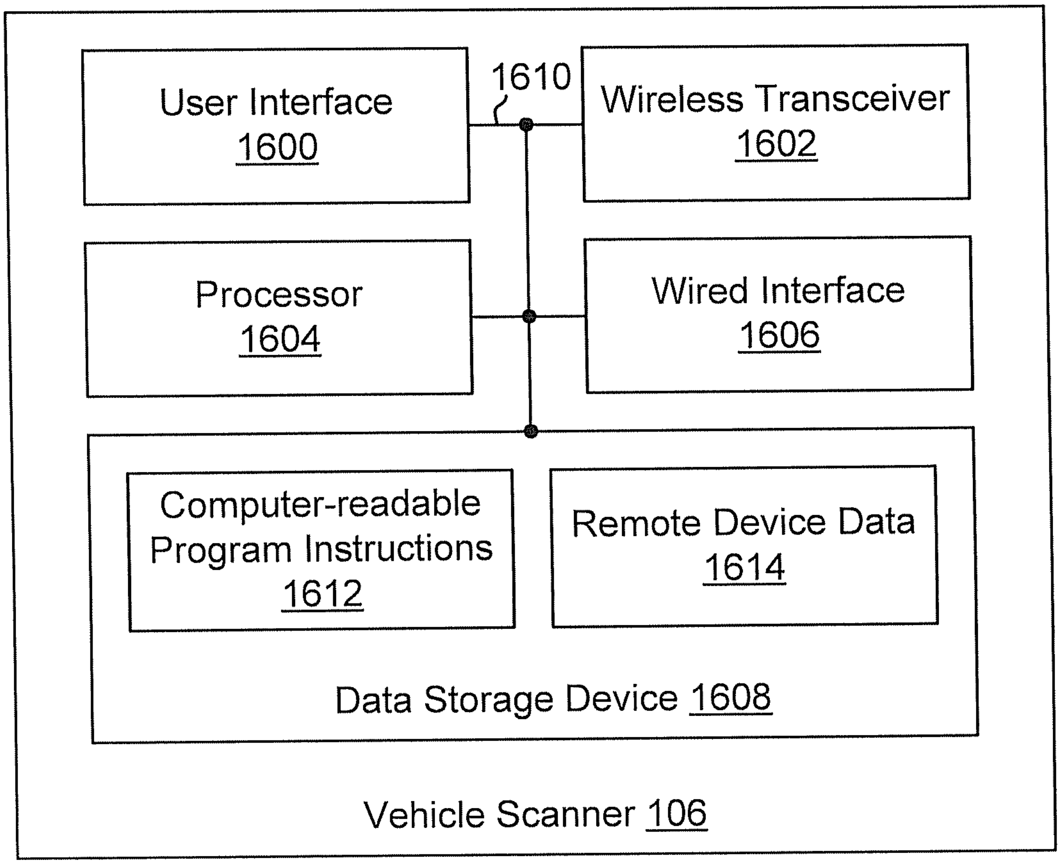
FIG. 16 is a block diagram of an example vehicle scanner.
Figure 17:
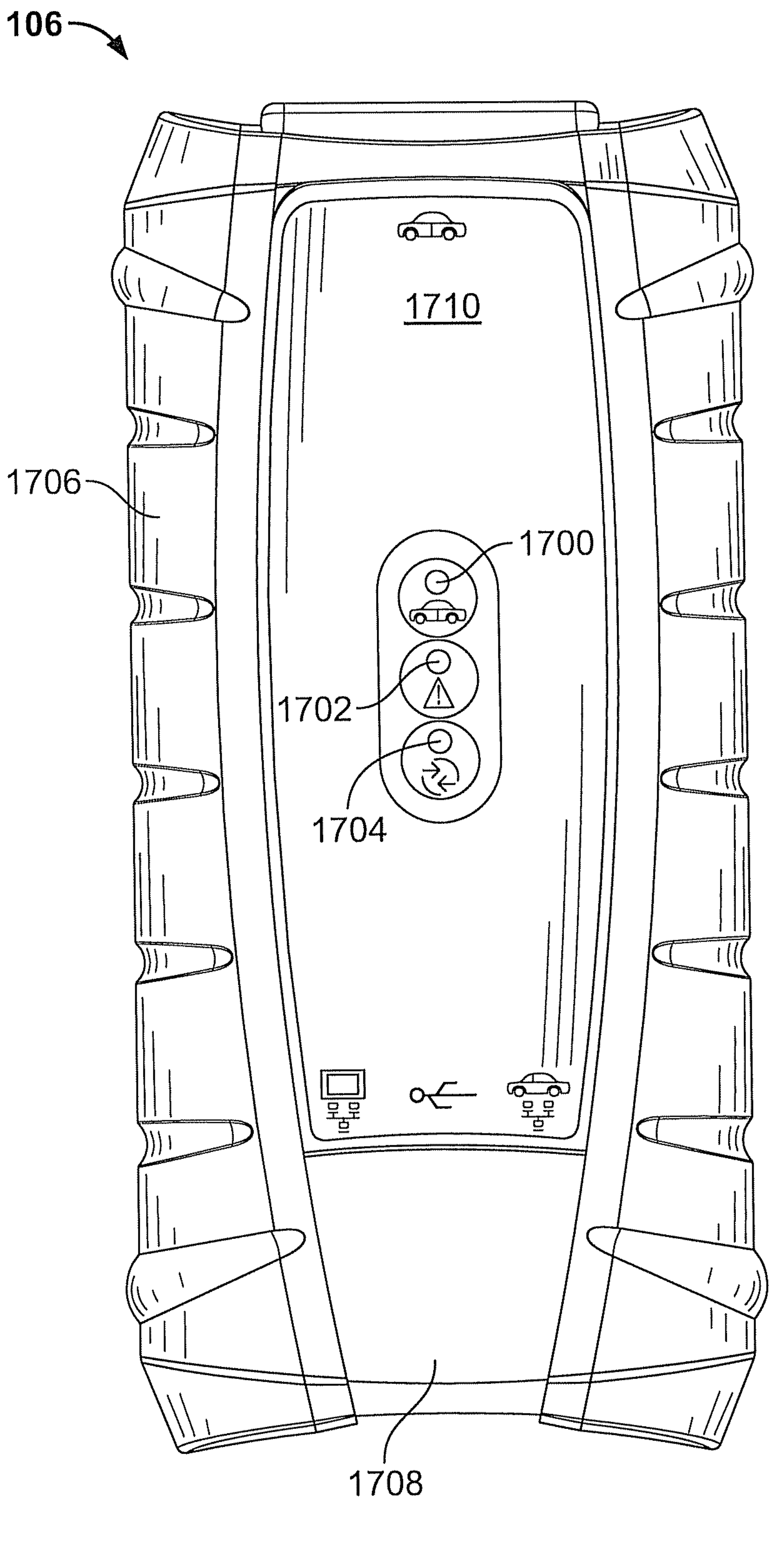
FIG. 17 to FIG. 28 illustrate various views and details of an example embodiment of the vehicle scanner of FIG. 16.

Next, FIG. 16 is a block diagram of vehicle scanner 106, and FIG. 17 to FIG. 28 illustrate details of an example embodiment of vehicle scanner 106. As illustrated in FIG. 16, vehicle scanner 106 includes a user interface 1600, a wireless transceiver 1602, a processor 1604, a wired interface 1606, and a data storage device 1608, all of which may be linked together via a system bus, network, or other connection mechanism 1610. User interface 1600 is operable to present data to a user of vehicle scanner 106. Elements of user interface 1600 are illustrated in FIG. 17.

Wireless transceiver 1602 comprises a wireless transceiver that is operable to carry out communications via wireless network 110. Wireless transceiver 1602 may comprise a Bluetooth transceiver, a Wi-Fi transceiver, or some other type of wireless transceiver. Wireless transceiver 1602 may carry out communications with DAQ device 104, display device 108, or some other device that is operating to communicate via wireless network 110.

Wireless transceiver 1602 is not limited to a single wireless transceiver. For example, wireless transceiver 1602 may comprise a Bluetooth transceiver and a Wi-Fi transceiver. In accordance with such an example, the Bluetooth transceiver may communicate with display device 108 and/or DAQ device 104 via a Bluetooth network of wireless network 110, and the Wi-Fi transceiver may communicate with display device 108 and/or DAQ device 104 via a Wi-Fi network of wireless network 110.

In accordance with an embodiment in which DAQ device 104, vehicle scanner 106, and display device 108 each include a single wireless transceiver (e.g., a Bluetooth transceiver), one of the devices, such as display device 108, can operate as a master, and the other devices, such as DAQ device 104 and vehicle scanner 106, can operate as slaves to the master.

In accordance with an embodiment in which DAQ device 104 includes a single transceiver (e.g., a Bluetooth transceiver) and vehicle scanner 106 and display device 108 each include two transceivers (e.g., a Bluetooth transceiver and a Wi-Fi transceiver), DAQ device 104 and vehicle scanner 106 may simultaneously transmit data to display device 108 for display via display 300. In that regard, DAQ device 104 may transmit data to display device 108 via the Bluetooth network of wireless network 110 and vehicle scanner 106 may transmit data to display device 108 via the Wi-Fi network of wireless network 110.

In accordance with an embodiment in which wireless transceiver 1602 includes three or more wireless transceivers, two or more of the wireless transceivers may communicate according to a common air interface protocol or different air interface protocols.

Wired interface 1606 may comprise one or more ports. As an example, wired interface 1606 may include a port 2100 (illustrated in FIG. 21), ports 2400, 2402, and 2404 (illustrated in FIG. 24), and port 2600 (illustrated in FIG. 26). Port 2600 may comprise a port that is connectable to a port of a circuit board 2700 (illustrated in FIG. 27).

Port 2100 may communicatively connect to wired link 114. In that regard, wired link may comprise a vehicle interface cable having two cable ends. A first cable end of the vehicle interface cable may include a connector that is connectable to and removable from port 2100. A second cable end of the vehicle interface cable may include a connector that is connectable to and removable from a connector in a vehicle. The connector in the vehicle may be arranged according to a particular connector standard, such as Society of Automotive Engineers (SAE) specification J-1962 or some other connector standard. Port 2100 may include connector pins for connecting to electrical power and ground conductors and to bi-directional communication buses that conduct serial data (e.g., serial data arranged according to an On Board Diagnostic II standard) generated by electronic control units within device-under-service 102. The serial data may comprise serial data arranged according to a proprietary standard developed by a manufacturer of device-under-service 102.

Port 2400 may comprise a USB port. The USB port may communicatively connect to a first end of a USB cable. A second end of the USB cable may connect to port 502 or to some other USB port. Various data can be transmitted via a USB cable connected to port 502. As an example, data to be stored as remote device data 1614 and data to be stored as remote device data 214 may be transmitted via the USB cable that connects ports 502 and 2400. A USB cable that connects to ports 502 and/or 2400 can be disconnected from those ports.

Ports 2402 and 2404 may comprise respective Ethernet ports. Each Ethernet port may communicatively connect to a first end of a respective Ethernet cable. A second end of each Ethernet cable may connect to a respective Ethernet port connected to a device connected to wired network 116 or some other device. As an example, the second end of an Ethernet cable may communicatively connect to an Ethernet port of device-under-service 102. As another example, the second end of an Ethernet cable may communicatively connect to the docking station to which display device 108 can be attached. As yet another example, a second end of an Ethernet cable may communicatively connect to an Ethernet port at network node 124.

Processor 1604 may comprise one or more general purpose processors (e.g., INTEL microprocessors) and/or one or more special purpose processors (e.g., digital signal processors). Processor 1604 may execute computer-readable program instructions 1612 that are contained in computer-readable data storage device 1608.

Data storage device 1608 may comprise a computer-readable storage medium readable by processor 1604. The computer-readable storage medium may comprise volatile and/or non-volatile storage components, such as optical, magnetic, organic or other memory or disc storage, which can be integrated in whole or in part with processor 1604. Data storage device 1608 may include computer-readable program instructions (CRPI) 1612, remote device data 1614, input data received from device-under-service 102 (e.g., serial data from an ECU within device-under-service 102), and other data.

Remote device data 1614 may include data associated with a device that is arranged to communicate with vehicle scanner 106 via wireless network 110. For example, remote device data 1614 may include data associated with display device 108, such as a radio identifier and password associated with display device 108. The data associated with display device 108 may be received at vehicle scanner 106, for storing as remote device data 1614, during a pairing process carried out between vehicle scanner 106 and display device 108. That pairing process may include vehicle scanner 106 providing display device 108 with the data (e.g., a passkey) associated with vehicle scanner 106 and display device 108 providing vehicle scanner 106 with data (e.g., a passkey) associated with display device 108. After carrying out the paring process with display device 108, vehicle scanner 106 may use the remote device data 1614 when establishing communication network 110 with display device 108.

Remote device data 1614 is not limited to data associated with one remote device. In that regard, remote device data 1614 may include respective data associated with each of a plurality of devices operable to communicate via wireless network 110, such as data associated with DAQ device 104, and data associated with display device 108. The data associated with DAQ device 104 may include a radio identifier and password associated with DAQ device 104. The data associated with DAQ device 104 may be received at vehicle scanner 106, for storing as remote device data 1614, during a pairing process carried out between DAQ device 104 and vehicle scanner 106. That pairing process may include DAQ device 104 providing vehicle scanner 106 with the data associated with DAQ device 104 and vehicle scanner 106 providing DAQ device 104 with data associated with vehicle scanner 106. After carrying out the paring process with DAQ device 104, vehicle scanner 106 may use remote device data 1614 when establishing wireless network 110 to communicate with DAQ device 104.

CRPI 1612 may comprise various program instructions. As an example, CRPI 1612 may include program instructions executable by processor 904 to determine a desired mode for vehicle scanner 106 to transition to and/or to operate in. The desired mode for vehicle scanner 106 may be identified via mode-selection command 3400 received at wireless transceiver 1602. Table 4 lists example system field information that can be included and/or represented by a system field 3408 of mode-selection command 3400, and mode field information that can be included and/or represented by a mode field 3406 of mode-selection command 3400.

TABLE 4

| System Field Information | | | Mode Field Information | |
|---|---|---|---|---|
| Model Year | Manufacturer | Model | Sub-system | Parameter |
| 2010 | Chevrolet | Camaro | Transmission | Oil Temperature |
| 2010 | Chevrolet | Camaro | Engine | MAP sensor |
| 2009 | Chevrolet | Malibu | SIR | DTC |
| 2008 | Ford | Mustang | Engine | DTC |

Each row in Table 4 represents an example desired mode for retrieving data from device-under-service 102 via vehicle scanner 106. The model year, manufacturer, and model are associated with device-under-service 102. The sub-system identifies a sub-system on device-under-service 102. The parameter identifies particular data to be requested from the identified sub-system of device-under-service 102. MAP refers to Manifold Air Pressure. SIR refers to Supplemental Inflatable Restraints. DTC refers to Diagnostic Trouble Code.

As another example, CRPI 1612 may include program instructions (referred to herein as PI-1612-A) that are executable to packetize data. As an example, processor 1604 may execute PI-1612-A to packetize input data, received from device-under-service 102 via wired interface 1606, into data share message 3500. That data share message, comprising packets of the input data, may subsequently be transmitted to another device via wireless transceiver 1602 or wired interface 1606.

Next, FIG. 17 illustrates a front view of an example embodiment of vehicle scanner 106. FIG. 17 further illustrates that vehicle scanner 106 includes visual indicators 1700, 1702, and 1704, a grip 1706, a port access cover 1708, and a cover 1710. Port access cover 1708 may provide protection for one or more ports of wired interface 1606. Cover 1710 may provide protection for (i) electrical circuitry connected to user interface 1600, (ii) wireless transceiver 1602, (iii) processor 1604, (iv) wired interface 1606, and (v) data storage device 1608.

Visual indicators 1700, 1702, and 1704, which may be part of user interface 1600, may include a respective light emitting diode (LED) or some other visual indictor that is operable to convey information to a user. Program instructions 1612 may be executable by processor 1604 to cause visual indicators 1702, 1704, and 1706 to (i) turn on steady (i.e., not off and not flashing), (ii) flash (e.g., turn on for 500 ms then turn off for 500 ms, and repeat), and (iii) turn off steady (i.e., not on and not flashing).

Visual indicator 1700 may turn on to indicate that vehicle scanner 106 is receiving electrical power from device-under-service 102 and/or that vehicle scanner 106 is connected to device-under-service 102. As an example, visual indicator 1700 can be turned on to indicate that wired interface 1606 is connected to an electrical power source (e.g., a battery) within device-under-service 102. As another example, visual indicator 1700 can flash to indicate that wired interface is communicating with device-under-server 102 (e.g., communicating with an electronic control unit (ECU) within device-under-service 102 via a serial data communication bus). Visual indicator 1700 may turn off steady if vehicle scanner 106 is not connected to device-under-service, if vehicle scanner 106 is not connected to the electrical power source within device-under-service 102, or for some other reason.

Visual indicator 1702 may turn on and off to so as to flash (e.g., turn on for 1 second and then turn off for 1 second). In particular, visual indicator 1702 may flash in specific sequences so as to identify any of a variety of diagnostic codes. The diagnostic codes, for example, could pertain to (i) device-under-service 102, (ii) vehicle scanner 106, or (iii) a device that is operable to communicate with vehicle scanner 106 via wireless transceiver 1602. As an example, visual indicator 1702 may flash 3 times, wait, and then flash 2 more times, so as to visually present a diagnostic code of 32.

Visual indicator 1704 may turn on to indicate that vehicle scanner 106 is carrying out communications with device-under-service 102. In accordance with an example embodiment in which device-under-service 102 comprises a vehicle, and vehicle scanner 106 is connected to the vehicle, visual indicator 1704 may turn on to indicate that vehicle scanner 106 is carrying out communications with at least one electronic control unit within the vehicle, and visual indicator 1704 may turn off to indicate that vehicle scanner 106 is not carrying out communications with at least one electronic control unit within the vehicle. Other examples of presenting data via visual indicators 1700, 1702, 1704 are also possible.

Grip 1706 can be arranged to cover portions of port access cover 1708 and portions of cover 1710. Grip 1706 may be removed away from port access cover 1708 so as to allow port access cover 1708 to be moved to an open position. Grip 1706 may be made from rubber. As an example, grip 1706 may be arranged as a single piece of rubber. When attached to vehicle scanner 106, grip 1706 may provide shock protection to vehicle scanner 106 in the event that vehicle scanner 106 is dropped or struck.

Figure 18:
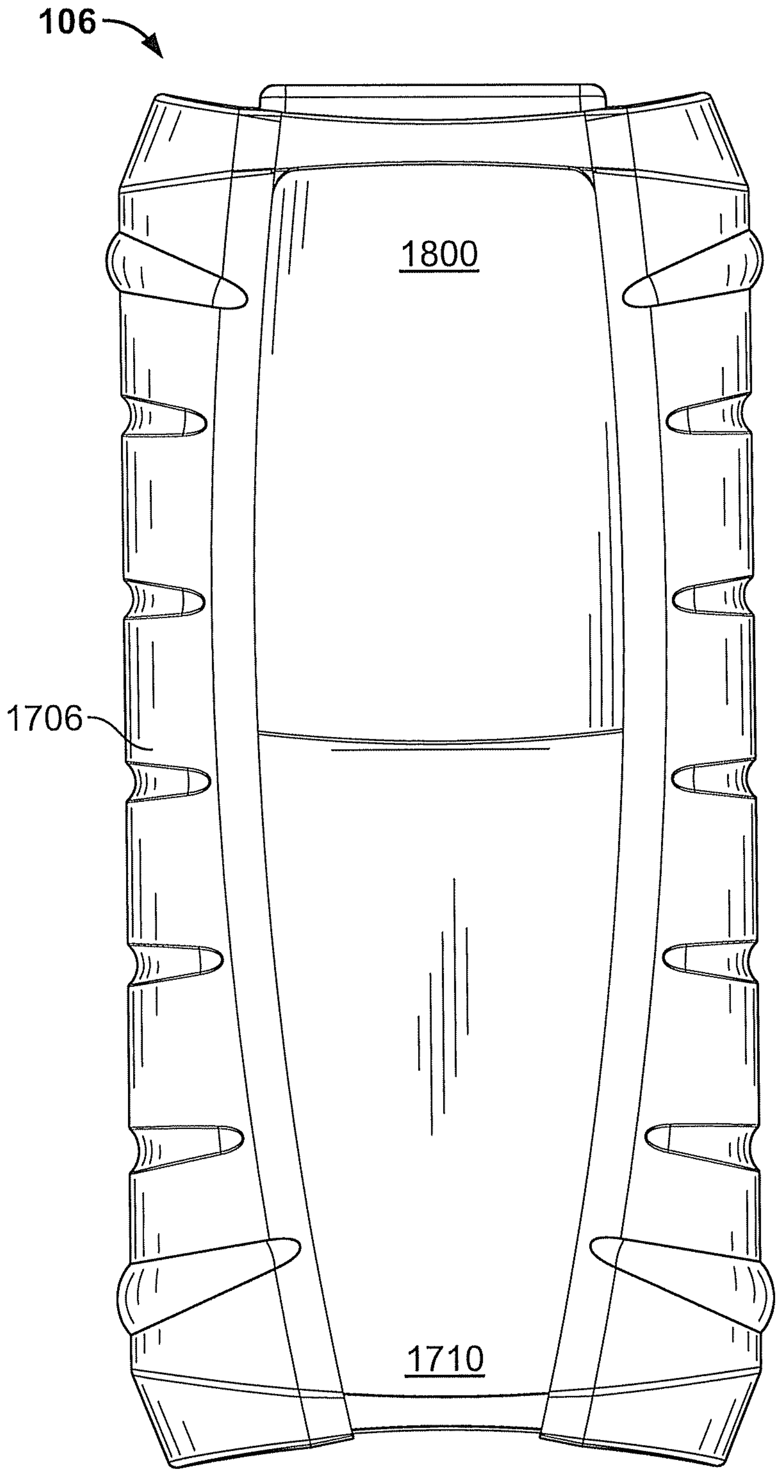

Next, FIG. 18 illustrates a back view of an example embodiment of vehicle scanner 106. FIG. 18 further illustrates grip 1706 and that vehicle scanner 106 includes an expansion cover 1800. Features related to expansion cover 1800 are illustrated in FIG. 25 to FIG. 28.

Figure 19:
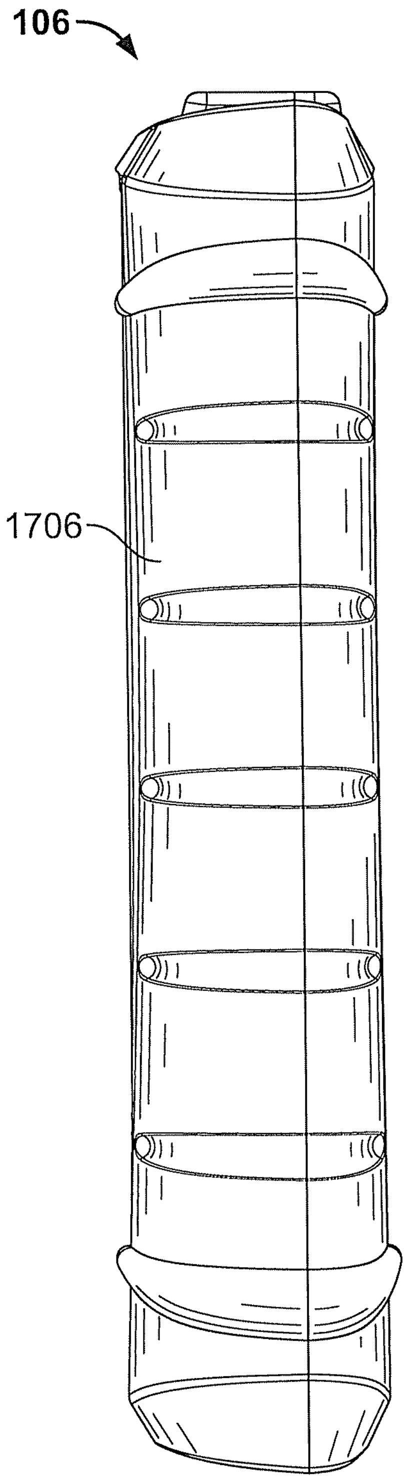
Figure 20:
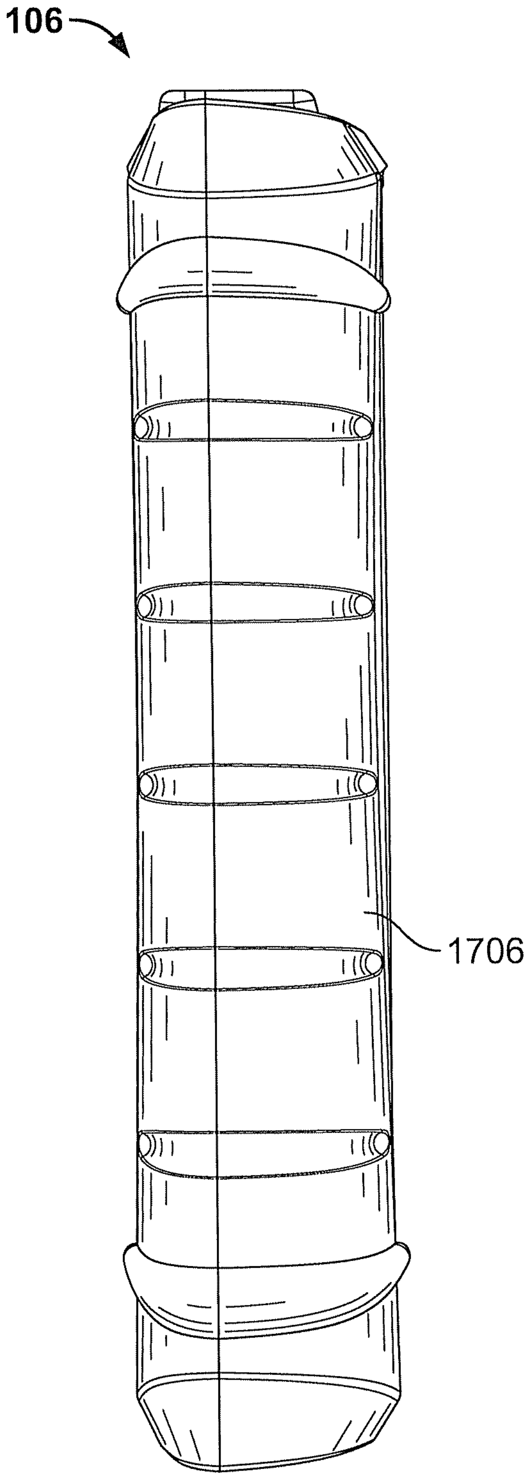

Next, FIG. 19 illustrates a left-side view of an example embodiment of vehicle scanner 106 and FIG. 20 illustrates a right-side view of an example embodiment of vehicle scanner 106. FIG. 19 and FIG. 20 each illustrate respective portions of grip 1706.

Figure 21:
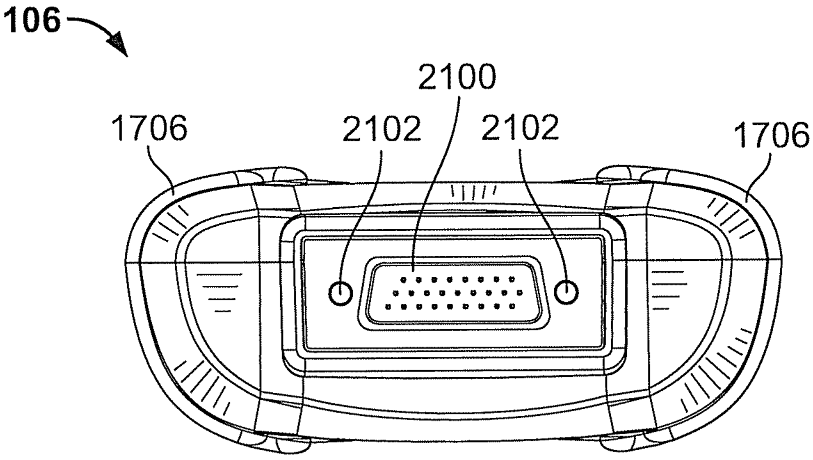

Next, FIG. 21 illustrates a top view of an example embodiment of vehicle scanner 106. FIG. 21 further illustrates grip 1706 and that vehicle scanner 106 includes a port 2100 and connector mounting holes 2102. As an example, port 2100 may comprise a high-density-26 (HD-26) connector, but port 2100 is not so limited. An HD-26 connector may include 26 male or female connector terminals. Port 2100 is arranged to connect to wired link 114. Wired link 114 may include fasteners that are arranged to fasten wired link 114 to vehicle scanner 106 via connector mounting holes 2102.

Figure 22:
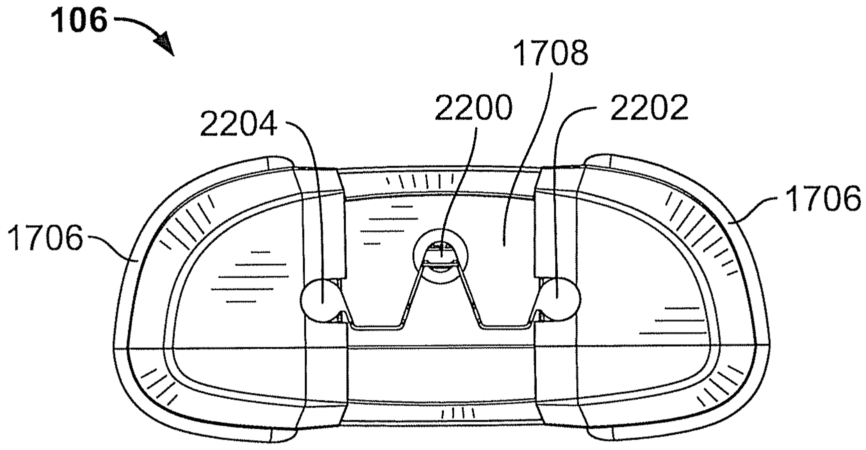

Next, FIG. 22 illustrates a bottom view of an example embodiment of vehicle scanner 106. FIG. 22 further illustrates grip 1706 and port access cover 1708, and that vehicle scanner 106 includes cable openings 2200, 2202, and 2204. Cable openings 2200, 2202, and 2204 allow cables connected to ports accessible via port access cover 1708 to extend away from vehicle scanner 106.

Figure 23:
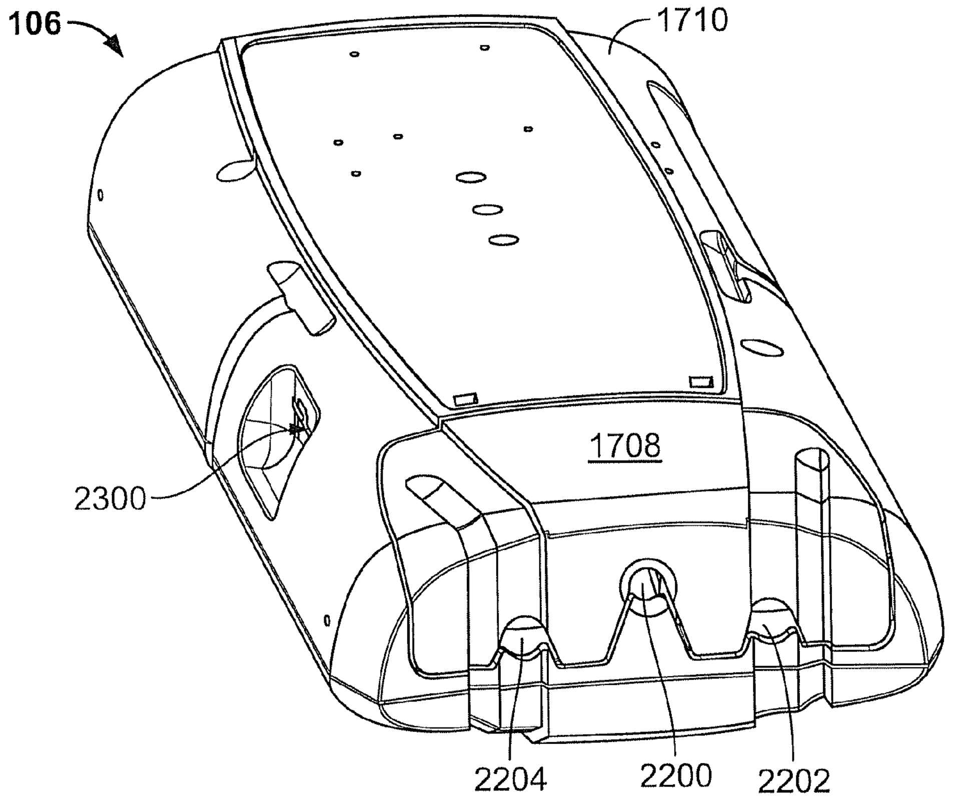

Next, FIG. 23 illustrates an example embodiment of vehicle scanner 106, but without grip 1706. FIG. 23 further illustrates cable openings 2200, 2202, and 2204, and port access cover 1708 in a closed position. While in the closed position, port access cover 1708 can apply a force on an outer surface of each cable within cable openings 2200, 2202, and 2204. The forces to those cables can prevent the cables from accidentally being pulled out from ports covered by port access cover 1708.

Figure 24:
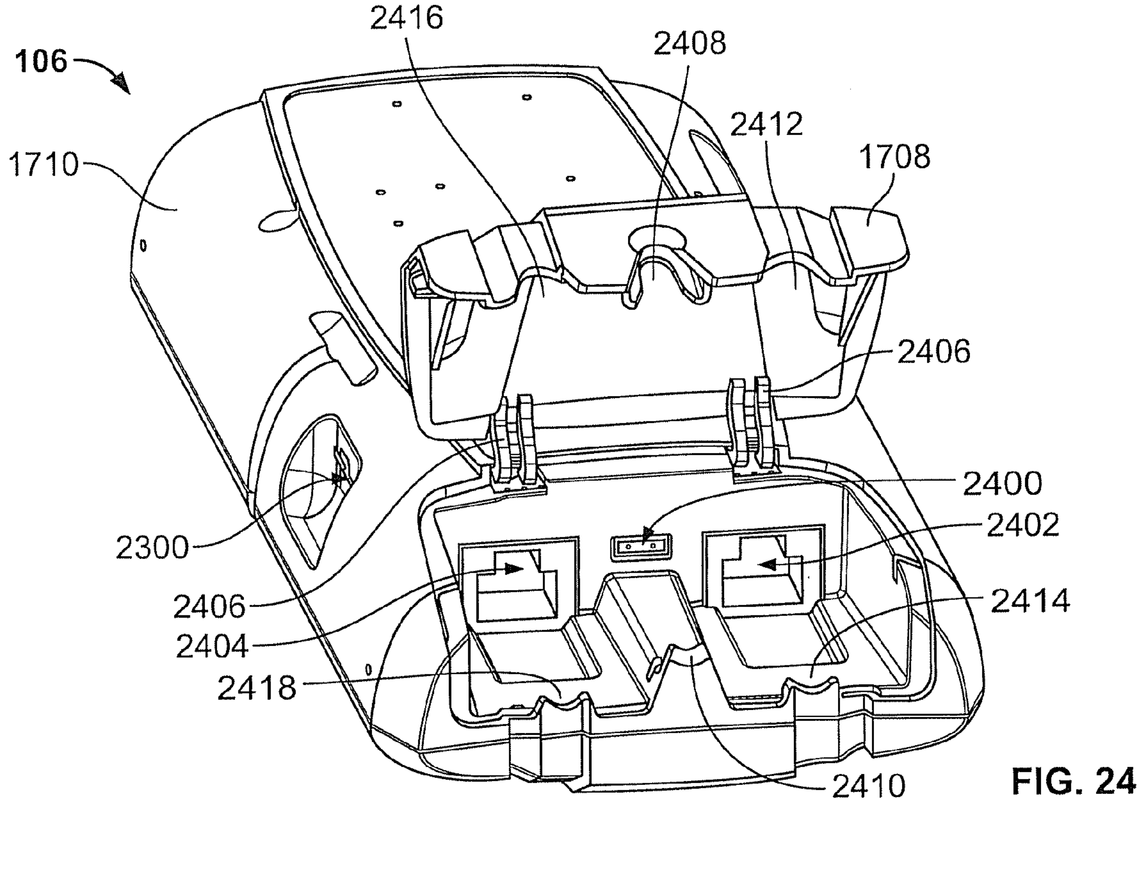

Next, FIG. 24 illustrates an example embodiment of vehicle scanner 106, but without grip 1706. FIG. 24 further illustrates port access cover 1708 in an open position and that vehicle scanner 106 includes ports 2400, 2402, and 2404, hinges 2406, and channels 2408, 2410, 2412, 2414, 2416, and 2418. Channels 2408 and 2410 form cable opening 2200 when port access cover 1708 is in the closed position. Channels 2412 and 2414 form cable opening 2202 when port access cover 1708 is in the closed position. Channels 2416 and 2418 form cable opening 2204 when port access cover 1708 is in the closed position.

Port 2400 may be arranged as a USB port or some other type of wired port, and ports 2402 and 2404 may be arranged as Ethernet ports or some other type of wired ports. In an alternative embodiment, the ports accessible via port access cover 1708 may include a quantity of ports greater than or less than 3 ports. Vehicle scanner 106 may include a respective cable opening for each port accessible via port access cover 1708. Alternatively, one or more cable openings may allow multiple cables to pass through port access cover 1708 so as to extend away from vehicle scanner 106.

Hinges 2406 provide for attachment of port access cover 1708 to vehicle scanner 106. Hinges 2406 are rotatable so as to allow port access cover 1708 to move from the open position to the closed position and from the closed position to the open position. While in the open position, a user can remove cables that are connected to ports 2400, 2402, and 2404.

Figure 25:
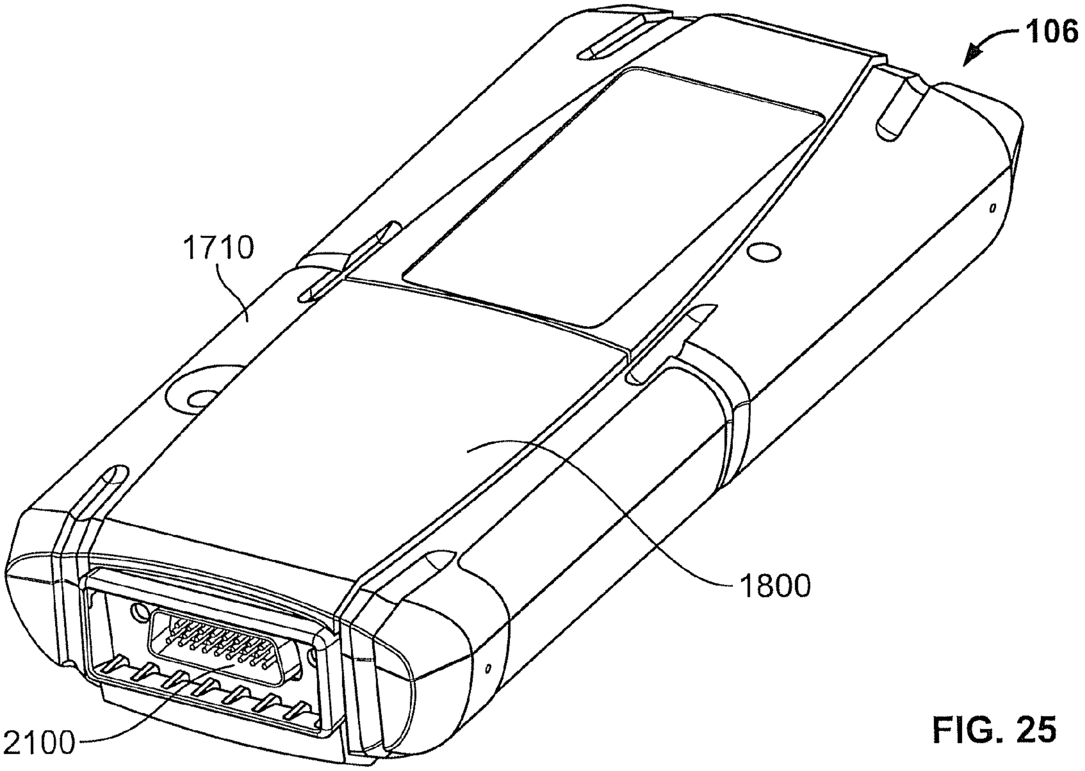

Next, FIG. 25 illustrates an example embodiment of vehicle scanner 106, but without grip 1706. FIG. 25 further illustrates expansion cover 1800 and port 2100. Expansion cover 1800 is removable from vehicle scanner 106 so as to provide access to an expansion port 2600 illustrated in FIG. 26.

Figure 26:
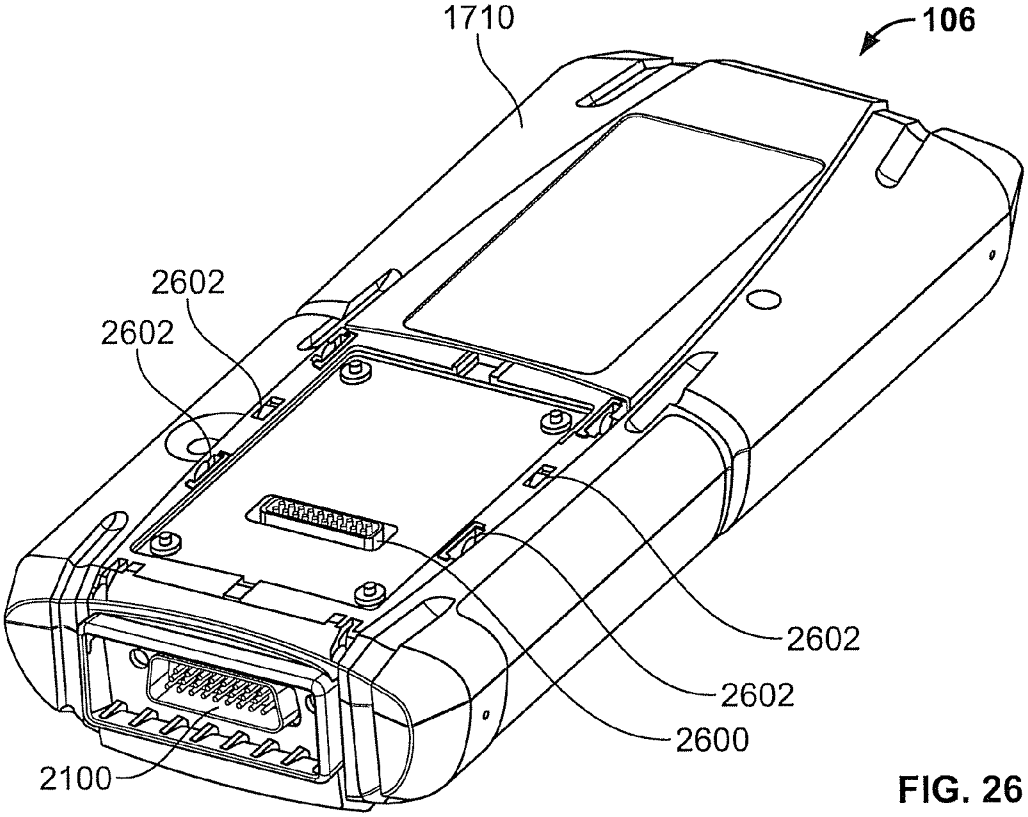

Next, FIG. 26 illustrates an example embodiment of vehicle scanner 106, but without grip 1706 and without expansion cover 1800. FIG. 26 further illustrates that vehicle scanner 106 includes expansion port 2600 and slots 2602. Expansion cover 1800 may include tabs (not shown) that can be inserted into slots 2602 and then slid in a direction away from port 2100 so as to secure expansion cover 1800 to vehicle scanner 106. Conversely, when expansion cover 1800 is secured to vehicle scanner 106, expansion cover 1800 and its tabs may be slid in a direction towards port 2100 so as to move the tabs to a position in which expansion cover 1800 may be removed from vehicle scanner 106.

Figure 27:
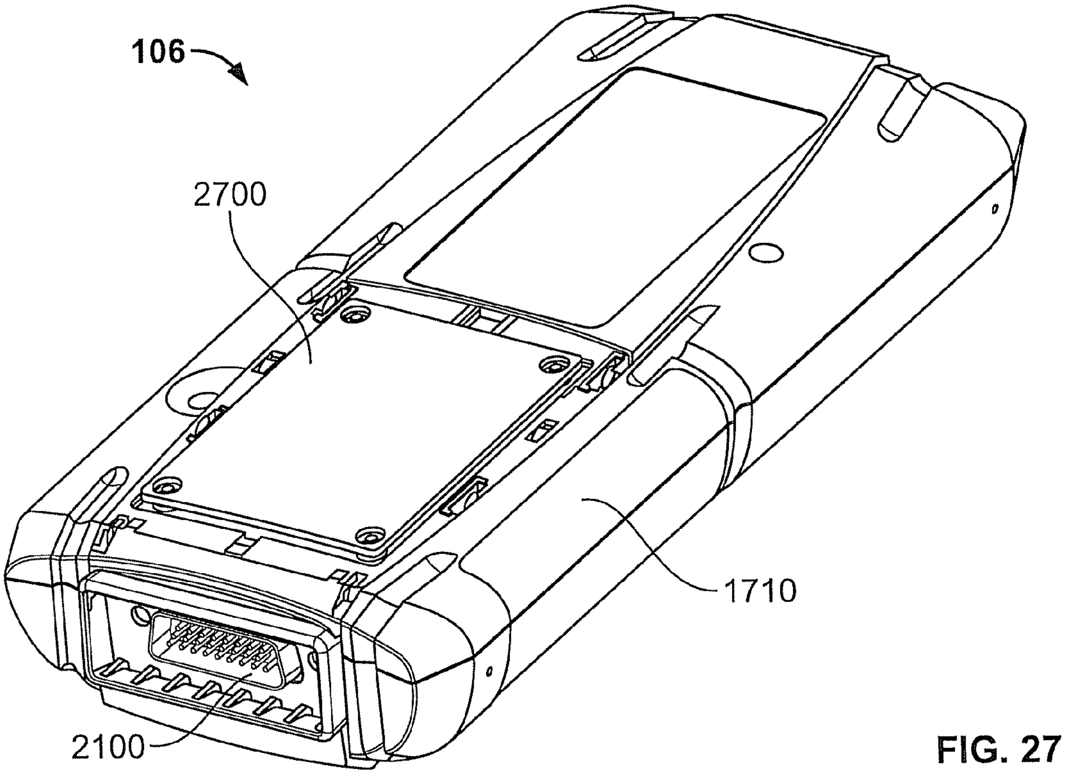

Next, FIG. 27 illustrates an example embodiment of vehicle scanner 106, but without grip 1706. FIG. 27 further illustrates that vehicle scanner 106 may include an expansion circuit board 2700. Expansion circuit board 2700 may include a mating port (not shown) that is connectable to expansion port 2600. Expansion circuit board 2700 may comprise, for example, a printed circuit board (PCB) containing a plurality of discrete circuit elements and/or one or more integrated circuits (ICs). Expansion circuit board 2700 can be communicatively connected to vehicle scanner 106 to provide additional and/or more robust functionality without the need to manufacture an entirely new vehicle scanner 106. The additional functionality may include functions for sending new-protocol messages to device-under-service 102. The new protocol messages may comprise messages arranged according to a communication protocol that is not defined within the computer-readable program instructions 1612 and/or that cannot be transmitted via wired interface 1606 unless expansion circuit board 2700 is connected to expansion port 2600.

Figure 28:
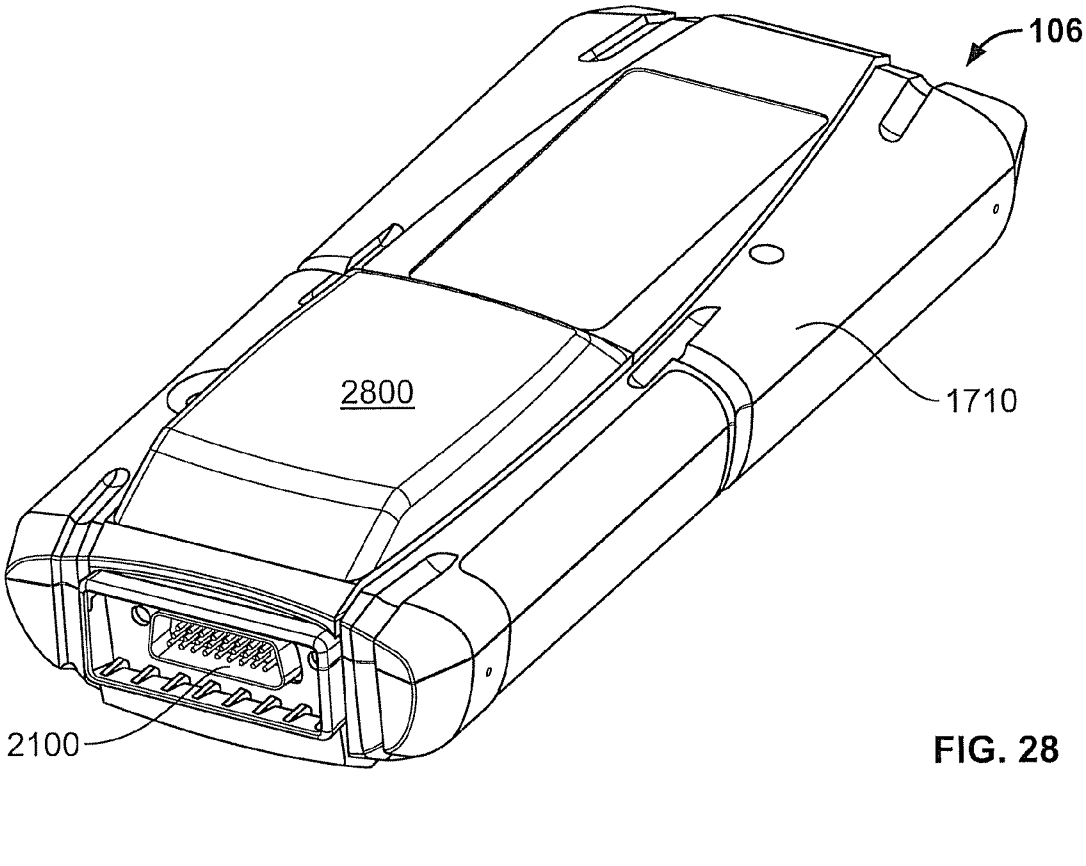

Next, FIG. 28 illustrates an example embodiment of vehicle scanner 106, but without grip 1706. FIG. 28 further illustrates that vehicle scanner 106 may include an expansion cover 2800. With respect to expansion cover 2800, expansion cover 2800 may be referred to as a large expansion cover, whereas expansion cover 1800 may be referred to as a low-profile expansion cover. The large expansion cover may be attached to vehicle scanner 106 regardless of whether circuit board 2700 is attached to vehicle scanner 106. On the other hand, the low-profile expansion cover may be attached to vehicle scanner 106 if expansion board 2700 is not attached to vehicle scanner 106, but may not be attached to vehicle scanner 106 when expansion board 2700 is attached to vehicle scanner 106.

Expansion cover 2800 may include tabs (not shown) that can be inserted into slots 2602 and then slid in a direction away from port 2100 and towards cover 1710 so as to secure expansion cover 2800 to vehicle scanner 106. Conversely, when expansion cover 2800 is secured to vehicle scanner 106, expansion cover 2800 and its tabs may be slid in a direction towards port 2100 and away from cover 1710 so as to move the tabs to a position in which expansion cover 2800 may be removed from vehicle scanner 106.

III. Example Communications

A variety of communications may be carried out via wireless network 110. Examples of those communications are illustrated in FIG. 34 and FIG. 35.

Figure 34:
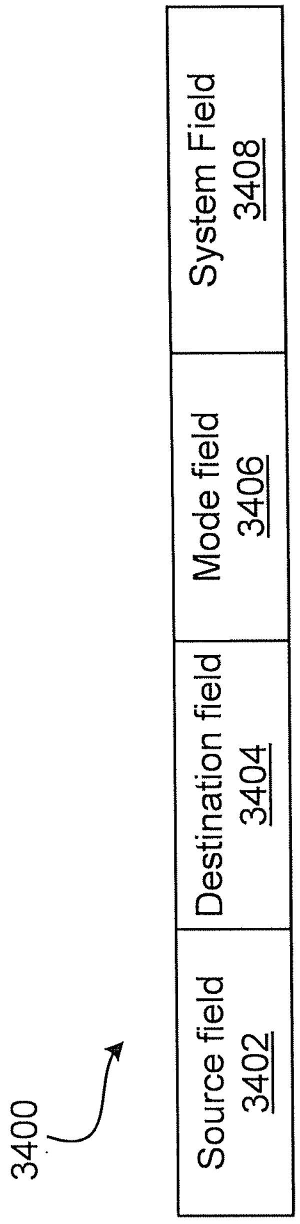
FIG. 34 and FIG. 35 illustrate example communications sent by one or more devices shown in FIG. 1.
Figure 35:
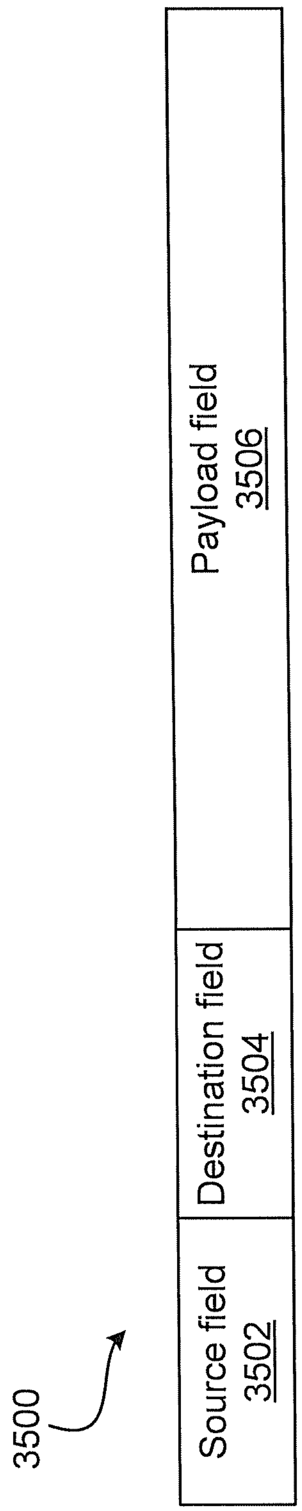

FIG. 34 illustrates an example mode-selection command 3400. Mode-selection command 3400 may comprise one or more data fields. As illustrated in FIG. 34, the data fields include a source field 3402, a destination field 3404, a mode field 3406, and a system field 3408. Source field 3402 may include an identifier of a device that generates and/or transmits mode-selection command 3400 (e.g., display device 108). Destination field 3404 may include an identifier of a destination device that is the destination for mode-selection command 3400 (e.g., DAQ device 104 or vehicle scanner 106) or identifiers of a plurality of destination devices that are the destinations for mode-selection command 3400 (e.g., DAQ device 104 and vehicle scanner 106).

Mode field 3406 may include an identifier of a desired operating mode for the device or devices identified by destination field 3404. If the destination device is DAQ device 104, the desired mode identified by mode field 3406 may comprise a DAQ mode associated with one of positions 1 though 8 of selector device 1002. If the destination device is vehicle scanner 106, the desired mode identified by mode field 3406 may comprise mode field information such as the example mode field information listed in Table 4.

System field 3410 may include an identifier of device-under-service 102 and/or a system contained at and/or within device-under-service 102. In accordance with an example embodiment in which device-under-service 102 comprises an automobile, such as a model year 2010 Chevrolet Camaro built by General Motors Corporation, Detroit, Mich., United States, the identifier of system field 3410 may comprise an identifier identifying device-under-service 102 as a 2010 Chevrolet Camaro and/or a system contained at and/or within a 2010 Chevrolet Camaro, such as an anti-lock brake system, a powertrain system, an HVAC system, a supplemental inflatable restraint (SIR) system, or some other system. Table 4 lists example system field information that may be contained in and/or represented by system field 3410.

If a device does not require information transportable via mode field 3406 or system field 3408, that field may be omitted from a mode-selection command to be transmitted to that device.

FIG. 35 illustrates an example data-share message 3500 for sharing data obtained by and/or stored at DAQ device 104, vehicle scanner 106, or display device 108 with another one or more of those devices. Data-share message 3500 may comprise a source field 3502, a destination field 3504, and a payload field 3506. Source field 3502 may include an identifier of a device that generates and/or that transmits data-share message 3500 (e.g., DAQ device 104, vehicle scanner 106, or display device 108). Destination field 3504 may include an identifier of a device that is the destination for data-share message 3500 (e.g., DAQ device 104, vehicle scanner 106, or display device 108) or identifiers of a plurality of devices that are the destinations for data-share message 3500 (e.g., two of DAQ device 104, vehicle scanner 106, and display device 108). Payload field 3506 may comprise the data obtained by and/or stored at the device that generates data-share message 3500. As an example, payload field 3506 may include instruction data 218, input data 922, or instruction data 924. As another example, payload field 3506 may include data received at wired interface 1606 from device-under-service 102.

IV. Example Operation

Figure 32:
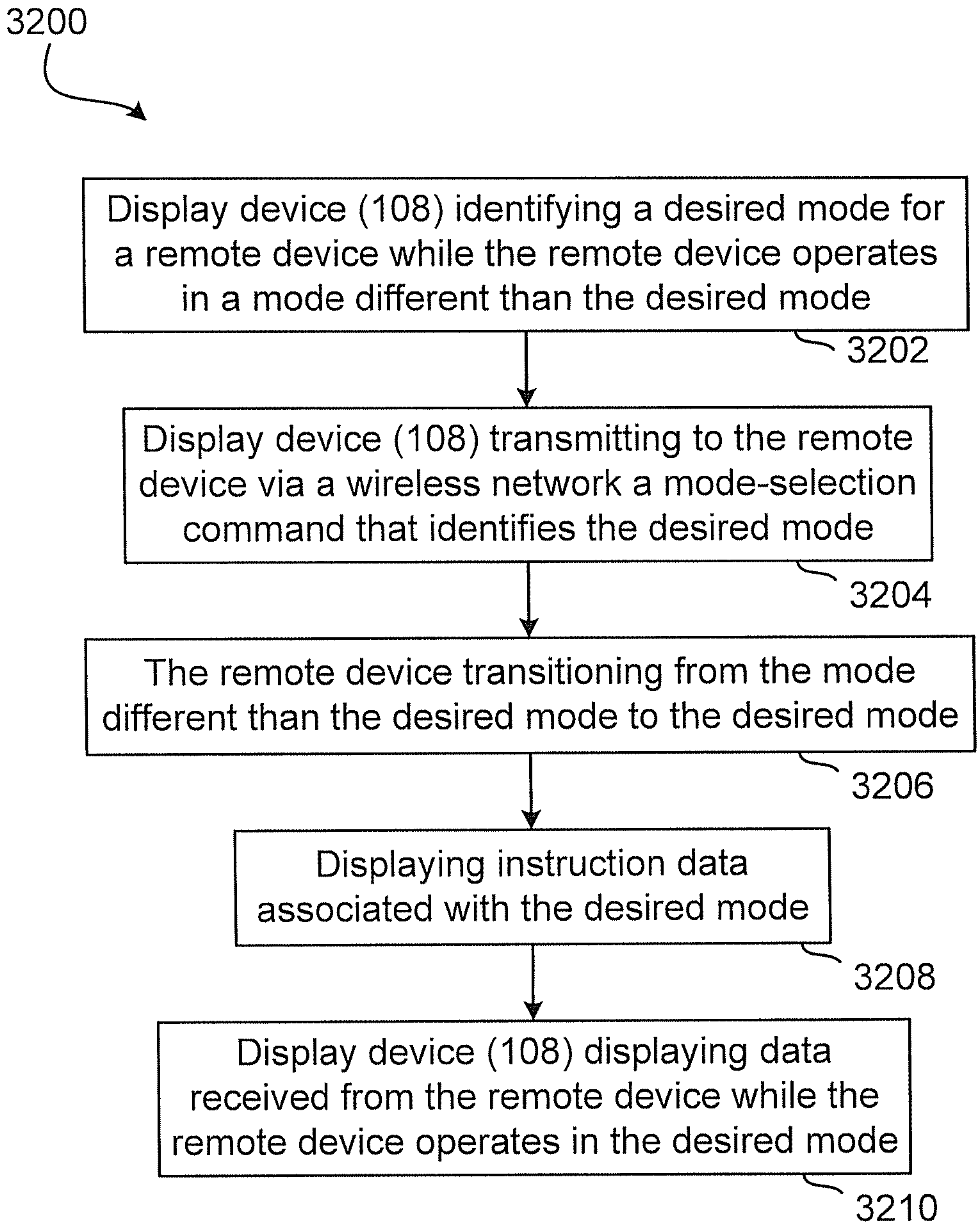
FIG. 32 is a flow chart depicting a set of functions that may be carried out in accordance with an example embodiment.

FIG. 32 depicts a flow chart that illustrates a set of functions 3200 that may be carried out in accordance with an example embodiment. Some of the functions pertain to changing an operating mode of a remote device. The remote device can operate in a desired mode and in a mode different than the desired mode. If the remote device is operating in a mode different than the desired mode, the remote device can transition from the mode different than the desired mode to the desired mode. Upon making that transition, the remote device operates in the desired mode.

Block 3202 includes display device 108 identifying a desired mode for a remote device. As an example, display device 108 may identify a desired mode for DAQ device 104 or a desired mode for vehicle scanner 106. Display 300 may display menu data 216 that lists one or more modes for the remote device. A user can select one of the listed modes as the desired mode. Display device 108 can identify the desired mode in response to a user selecting a listed mode from display 300. In response to identifying the desired mode, processor 904 can generate a mode-selection command 3400 that identifies the desired mode.

If the remote device of block 3202 is DAQ device 104, the desired mode may comprise a mode listed in the mode column of Table 2 or some other operating mode (e.g., data acquisition mode) of DAQ device 104. An example list of menu items representing operating modes for DAQ device 104 is illustrated in FIG. 30. Those menu items include off mode menu item 3002, a Volts DC mode menu item 3004, a Volts AC mode menu item 3006, a Resistance mode menu item 3008, a Diode/Continuity mode menu item 3010, an Auxiliary mode menu item 3012, a Capacitance mode menu item 3014, and an Oscilloscope mode menu item 3016. Identifying the desired mode may include identifying a sub-mode. An example list of menu items representing sub-modes for DAQ device 104, when the desired mode is Volts AC mode, is illustrated in FIG. 31. Those menu items include a Peak-to-Peak sub-mode menu item 3102, a Root-Mean-Square sub-mode menu item 3104, a Duty cycle mode menu item 3106, and a Frequency mode menu item 3108.

If the DAQ device of block 3202 is vehicle scanner 106, the desired mode may comprise a mode identified by mode-selection command 3400, such as a mode identified by Table 4 or some other mode which vehicle scanner 106 may operate.

Next, block 3204 includes display device 108 transmitting to the remote device via a wireless network a mode-selection command that identifies the desired mode. As an example, wireless transceiver 202 of display device 108 may transmit mode-selection command 3400 to DAQ device 104 or vehicle scanner 106 via wireless network 110.

Next, block 3206 includes the remote device transitioning from the mode different than the desired mode to the desired mode. The remote device may carry out that transition in response to the remote device receiving mode-selection command 3400. If the remote device of block 3206 is DAQ device 104, then DAQ device 104 may execute program instructions contained in CRPI 918 to carry out the transition of block 3206. If the remote device of block 3206 is vehicle scanner 106, then vehicle scanner 106 may execute program instructions contained in CRPI 1612 to carry out the transition of block 3206.

The remote device is operable to obtain data while operating in the desired mode. If the remote device of block 3206 is DAQ device 104, the data obtained while operating in the desired mode can be obtained and processed via input elements 906 and then provided to wireless transceiver 902 for transmission of that data to display device 108 via wireless network 110. If the remote device of block 3206 is vehicle scanner 106, the data obtained while operating in the desired mode can be obtained via wired interface 1606 and then provided to wireless transceiver 1602 for transmission of that data to display device 108 via wireless network 110.

Next, block 3208 includes displaying instruction data associated with the desired mode. The instruction data may comprise data that identifies how to connect a portion of the remote device to device-under-service 102, how to operate device-under-service 102, visual inspections to carry out on device-under-service 102, or some other instruction data. The instruction data may comprise various data including numbers, letters, punctuation marks, pictures, graphs, waveforms, or some other visually presentable form of data.

In accordance with an example in which the desired mode of block 3208 is a desired mode of DAQ device 104, the instruction data may comprise data that illustrates how to connect input leads 912 to obtain an input signal from a particular input signal acquisition point of device-under-service 102. As another example, the instruction data may comprise data that illustrates how to connect input leads 912 to one or more of ports 1020, 1022 and 1024.

For an embodiment in which device-under-service 102 is an automobile, the instruction data that identifies how to operate device-under-service 102 may comprise data with instructions to operate the automobile at a particular speed or to operate the engine at a particular revolutions per minute (RPM).

Displaying the instruction data may comprise display 300 displaying the instruction data. If the instruction data to be displayed via display 300 is contained in data storage device 208, processor 204 may execute program instruction in CRPI 212 that causes the instruction data to be sent from data storage device 208 to display 300 via connection mechanism 210. If the instruction data to be displayed via display 300 is not contained in data storage device 208, display device 108 may, for example, receive the instruction data via network node 124 or from some other device.

Additionally or alternatively, displaying the instruction data may comprise display 1000 displaying the instruction data. If the instruction data to be displayed via display 1000 in contained in data storage device 908, processor 904 may execute program instruction in CRPI 918 that causes the instruction data to be sent from data storage device 908 to display 1000 via connection mechanism 910. If the instruction data to be displayed via display 1000 is not contained in data storage device 908, DAQ device 104 may receive the instruction data from display device 108 via wireless network 110. In that regard, display device 108 may transmit the instruction data as payload 3506 of message 3500.

Next, block 3210 includes display device 108 displaying data received from the remote device while the remote device operates in the desired mode. As an example, display 300 of display device 108 can display data received via input element 906 while DAQ device 104 operates in the desired mode (e.g., an oscilloscope mode). As another example, display 300 of display device 108 can display data received via wired interface 1606 while vehicle scanner 106 operates in the desired mode (e.g., a data retrieval mode listed in Table 4).

Figure 33:
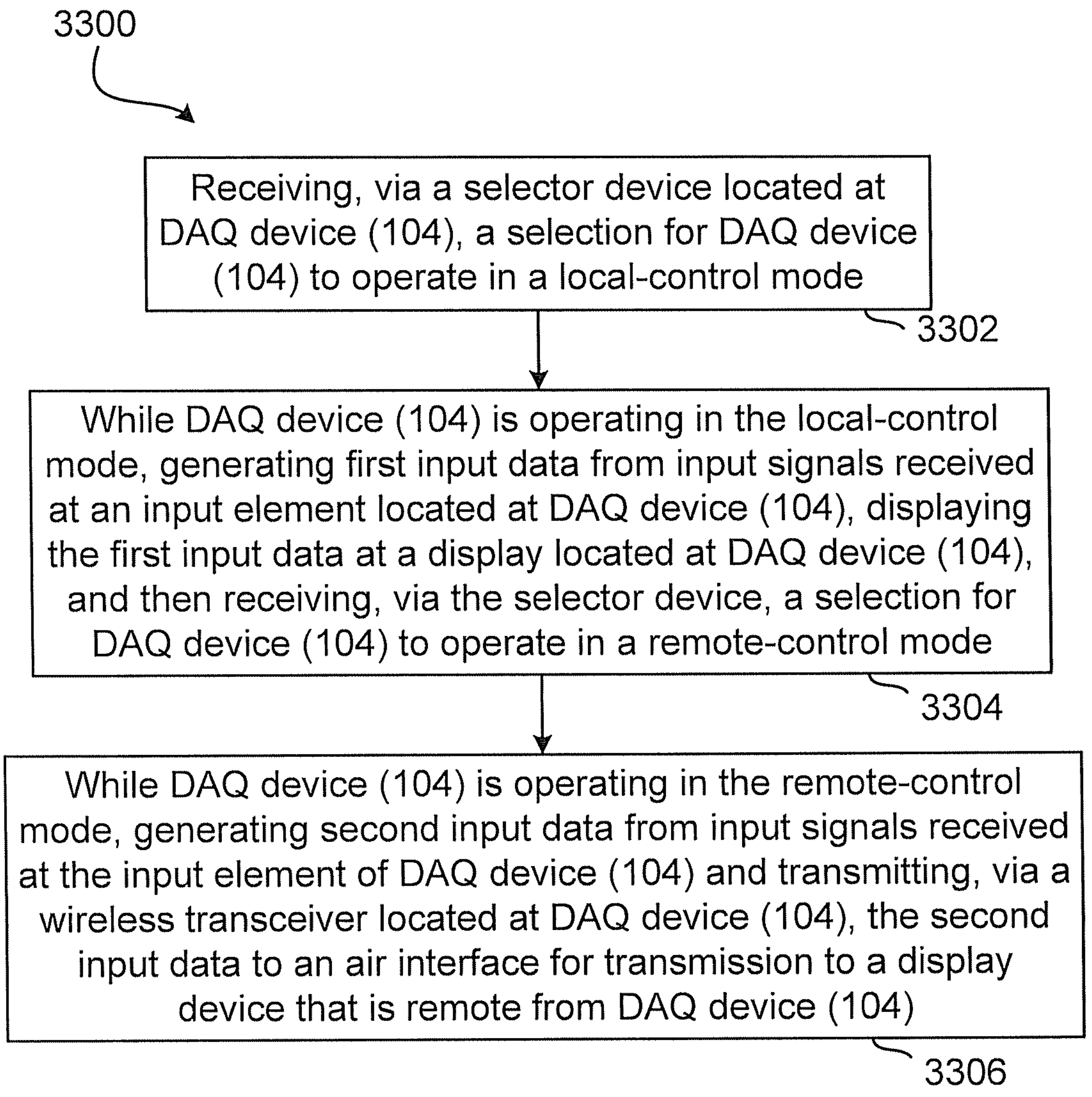
FIG. 33 is another flow chart depicting a set of functions that may be carried out in accordance with an example embodiment.

Turning to FIG. 33, that figure depicts a flow chart that illustrates a set of functions 3300 that may be carried out in accordance with an example embodiment. Block 3302 includes receiving, via a selector device located at DAQ device 104, a selection for DAQ device 104 to operate in a local-control mode. At the time the selection is received, DAQ device 104 may be operating in a remote-control mode or an off mode. After transitioning to the local-control mode and while operating in the local-control mode, DAQ device 104 may further operate in a data-acquisition mode, such as a mode listed in Table 2 or some other data-acquisition mode.

Next, block 3304 includes while DAQ device 104 is operating in the local-control mode, generating first input data from input signals received at an input element located at DAQ device 104, displaying the first input data at a display located at DAQ device 104, and then receiving, via the selector device, a selection for DAQ device 104 to operate in a remote-control mode.

The input element 906 may receive the input signals via input leads 912. The input signals received at the input element 906 are input signals for the data-acquisition mode in which DAQ device 104 is presently operating. For example, if DAQ device 104 is operating in the volts DC mode, the input signals are input signals for the volts DC mode (e.g., the input signals are direct current voltages). The first input data may include input data from one or more input channels at input element 906.

Displaying the first data at display 300 may comprise displaying the first data as numbers, letters, punctuation marks, pictures, graphs, waveforms, or some other visually presentable form of data. Alternatively, displaying the first data may comprise displaying a combination of numbers, letters, punctuation marks, pictures, graphs, waveforms, or some other visually presentable form of data.

Receiving the selection for DAQ device 104 to operate in the remote-control mode may occur in response to turning selector device 1002 to a position associated with a remote-control mode. In response to receiving the selection, wireless transceiver 902 may transition from a transceiver-off state to a transceiver-on state, and DAQ device 104 establishing a wireless network with display device 108 via wireless network 110. Upon transitioning from the local-control mode to the remote-control mode, selector devices 1004-1018 may be inoperative while DAQ device 104 continues to operate in the remote-control mode.

Next, block 3306 includes while DAQ device 104 is operating in the remote-control mode, generating second input data from input signals received at the input element of DAQ device 104 and transmitting, via a wireless transceiver located at DAQ device 104, the second input data to an air interface for transmission to a display device that is remote from the DAQ device 104. After receiving the second data, display device 108 may display the second data at display 300. Displaying the second data at display 300 may comprise displaying the second data as numbers, letters, punctuation marks, pictures, graphs, waveforms, or some other visually presentable form of data or combination of data. Alternatively, displaying the second data may comprise displaying a combination of numbers, letters, punctuation marks, pictures, graphs, waveforms, or some other visually presentable form of data.

While operating in the remote-control mode and in a first data-acquisition mode, the wireless transceiver 902 may receive a mode-selection command 3400 via an air interface of wireless network 110. The mode selection command 3400 may identify a second data acquisition mode. In response to receiving that mode selection command 3400 and while DAQ device 104 is operating in the remote-control mode, DAQ device 104 can transition from operating in the first data acquisition mode to the second data acquisition mode. The second data may be received while DAQ device 104 is operating in the first data acquisition mode, the second data acquisition mode, or both the first and second data acquisition modes.

V. Alternative Selector Devices and Use of Selector Devices

As illustrated in Table 2, each position of selector device 1002 may be associated with a mode control type and a particular data acquisition mode or modes. In an alternative arrangement, the absolute position of selector device 1002 is not relevant to determining a mode control type and a particular data acquisition mode. In accordance with this alternative arrangement, selector device 1002 can be turned more than 360 degrees in both a clockwise or counterclockwise direction, and have positions spaced out throughout a 360 degree rotation. Furthermore, with this alternative arrangement, the various positions of the selector device are not associated with the symbols as shown in FIG. 10.

Using this alternative selector device arrangement may include storing a mode matrix and mode pointer in data storage device 908. Table 4 illustrates example data that can be contained in the mode matrix. In that regard, the mode matrix may list multiple modes including data acquisition modes and an off mode, and multiple data addresses. Each of the addresses refers to an address (e.g., a particular data byte) within data storage device 908. Each mode within the mode matrix may be associated with a respective data address.

TABLE 5

| Mode | Data Address |
|---|---|
| Off mode | 600A |
| Volts DC mode | 600B |
| Volts AC mode | 600C |
| Resistance mode | 600D |
| Diode/Continuity mode | 600E |
| Auxiliary mode | 600F |
| Capacitance mode | 6010 |
| Oscilloscope mode | 6011 |
| Remote Selection mode | 6012 |

The mode pointer may be contained at another data address within data storage device 908 (e.g., data address 65F0). The mode pointer may point to the current operating mode for DAQ device 104. In that regard, the mode pointer may identify the data address of the current mode for DAQ device. For example, when DAQ device 104 is operating in the resistance mode, the mode pointer may identify data address 600D.

Table 6 illustrates an alternative way to use information within a selector device and mode-selection command 3400 to select a mode and mode control type and to cause the mode pointer to change. Row 1 represents a default starting point as being the off mode. The mode pointer is initially 600A. For the rows following row 1, the mode pointer changes as a result of (i) selector device movement (e.g., a clockwise or counter clockwise movement using a rotary switch such as selector device 1002, an up arrow movement using a push button such as selector device 1004, or a down arrow movement using a push button such as selector device 1012), or (ii) receipt of a mode-selection command 3400. Upon entering the remote selection mode (e.g., at rows 8, 14, and 18), DAQ device 104 may, for example, continue to operate in the most-recent mode prior to entering the remote selection mode or operate in some default mode in which DAQ device 104 waits for a mode-selection command prior to transitioning to a new mode.

TABLE 6

| Row | Selector Device Movement | Mode-selection Command | Mode | Mode Control Type | Mode Pointer |
|---|---|---|---|---|---|
| 1 | N.A. | N.A. | Off | Local | 600A |
| 2 | Clockwise (Up) | N.A. | Volts DC | Local | 600B |
| 3 | Clockwise (Up) | N.A. | Volts AC | Local | 600C |
| 4 | Clockwise (Up) | N.A. | Resistance | Local | 600D |
| 5 | Counter-clockwise (Down) | N.A. | Volts AC | Local | 600C |
| 6 | Counter-clockwise (Down) | N.A. | Volts DC | Local | 600B |
| 7 | Counter-clockwise (Down) | N.A. | Off | Local | 600A |
| 8 | Counter-clockwise (Down) | N.A. | Remote selection | Remote | 6012 |
| 9 | N.A. | 1010 | Capacitance | Remote | 6010 |
| 10 | N.A. | 100B | Volts DC | Remote | 600B |
| 11 | N.A. | 100F | Auxiliary | Remote | 600F |
| 12 | Clockwise | N.A. | Capacitance | Local | 6010 |
| 13 | Clockwise | N.A. | Oscilloscope | Local | 6011 |
| 14 | Clockwise | N.A. | Remote selection | Local | 6012 |
| 15 | Clockwise | N.A. | Off | Local | 600A |
| 16 | Clockwise | N.A. | Volts DC | Local | 600B |
| 17 | Counter-clockwise (Down) | N.A. | Off | Local | 600A |
| 18 | Counter-clockwise (Down) | N.A. | Remote selection | Remote | 6012 |
| 19 | N.A. | 100E | Diode/ Continuity | Remote | 600E |

In accordance with the example illustrated in Table 6, display 1000 may visually present an indicator or indicia (e.g., text or icons) to identify the mode in which DAQ device 104 is operating. In that regard, upon receiving a mode-selection command 3400, DAQ device 104 can change the mode pointer to a new mode, transition from a current data-acquisition mode to the new mode, and visually present on display 1000 that DAQ device 104 is operating in the new mode. DAQ device 104 may use alternative ways to identify which mode DAQ device 104 is currently operating.

VI. Conclusion

Example embodiments have been described above. Those skilled in the art will understand that changes and modifications may be made to the described embodiments without departing from the true scope and spirit of the present invention, which is defined by the claims.

We claim:

1. A data acquisition (DAQ) device comprising:

an input element configured to generate first input data from first input signals and to generate second input data from second input signals;

a wireless transceiver;

a user interface display;

a processor, a computer-readable medium storing program instructions, and a selector device including a control-mode selector and a DAQ-mode selector, wherein a first engagement of or changing a position of the control-mode selector causes the processor to execute stored program instructions to change an operating state of the DAQ device from a remote-control mode to a local-control mode, wherein the input element is configured to acquire the first input signals using a DAQ mode selected by use of the DAQ mode selector while the DAQ device operates in the local-control mode, wherein the program instructions are executable by the processor to cause the user interface display to visually present the first input data while the DAQ device operates in the local-control mode, wherein a second engagement of or changing a position of the control-mode selector causes the processor to execute stored program instructions to change an operating state of the DAQ device from the local-control mode to the remote-control mode, wherein the wireless transceiver is configured to receive a mode selection command that indicates a DAQ mode the input element will use while the DAQ device operates in the remote control mode, wherein, while the DAQ device operates in the remote control mode, the input element is configured to acquire the second input signals using the DAQ mode indicated by the mode selection command; and wherein the program instructions are executable by the processor to cause, the wireless transceiver to transmit, while the DAQ device operates in the remote-control mode, the second input data to an air interface for transmission of the second input data to the display device remote from the DAQ device.

2. The DAQ device of claim 1, wherein the program instructions include first computer-readable program instructions executable to cause the DAQ device to transition from the local-control mode to the remote-control mode and second computer-readable program instructions executable to cause the DAQ device to transition from the remote-control mode to the local-control mode, wherein the processor executes the first program instructions, in response to the selector device being used to select that the DAQ device operates in the remote-control mode, while the DAQ device operates in the local-control mode, and wherein the processor executes the second program instructions, in response to the selector device being used to select that the DAQ device operates in the local-control mode, while the DAQ device operates in the remote-control mode.

3. The DAQ device of claim 2, wherein the transition from the remote-control mode to the local-control mode includes a transition of the wireless transceiver from a transceiver-on-state to a transceiver-off-state, wherein, while the DAQ device operates in the local-control mode, the wireless transceiver operates in the transceiver-off-state, wherein the transition from the local-control mode to the remote-control mode includes a transition of the wireless transceiver from the transceiver-off-state to the transceiver-on-state, and wherein, while the DAQ device operates in the remote-control mode, the wireless transceiver operates in the transceiver-on-state.

4. The DAQ device of claim 1, wherein the position of the control-mode selector that causes the processor to execute stored program instructions to change the operating state of the DAQ device from the remote-control mode to the local-control mode causes a selection of the DAQ mode for the local control mode.

5. The DAQ device of claim 4, wherein the first data-acquisition mode comprise a data acquisition mode selected from the group consisting of (i) a mode to measure direct current volts, (ii) a mode to measure alternating current volts, (iii) a mode to measure resistance of an electrical circuit or component, (iv) a mode to test a diode, (v) a mode to test continuity of an electrical circuit or component, (vi) a mode to measure capacitance of an electrical circuit or component, (vii) an oscilloscope mode, and (viii) an auxiliary mode.

6. The DAQ device of claim 4, wherein the DAQ mode indicated by the mode selection command comprises a data-acquisition mode selected from the group consisting of (i) a mode to measure direct current volts, (ii) a mode to measure alternating current volts, (iii) a mode to measure resistance of an electrical circuit or component, (iv) a mode to test a diode, (v) a mode to test continuity of an electrical circuit or component, (vi) a mode to measure capacitance of an electrical circuit or component, (vii) an oscilloscope mode, and (viii) an auxiliary mode.

7. The DAQ device of claim 6, wherein the mode selection command identifies sub-mode information for configuring the DAQ mode indicated by the mode selection command.

8. The DAQ device of claim 1, wherein, when the DAQ device operates in the remote-control mode, the user interface display visually presents text and/or a graphical image to notify a user that the DAQ device is operating in the remote-control mode.

9. The DAQ device of claim 1, wherein the input element includes one or more input leads, wherein the wireless transceiver is configured to receive, via an air interface, information regarding connection of at least one input lead to a respective input signal acquisition point within a device-under-service, and wherein the user interface display is configured to visually present the information regarding connection of at least one input lead to a respective input signal acquisition point within a device-under-service.

10. The DAQ device of claim 1, wherein the user interface display is configured to visually present the first input data as (i) a histogram, (ii) a numeric value, (iii) an oscilloscope waveform, or (iv) a numeric value and an oscilloscope waveform.

11. The DAQ device of claim 1, wherein the selector device comprises a rotary switch having multiple switch positions, wherein the position of the control-mode selector that causes the processor to execute stored program instructions to change the operating state of the DAQ device from the remote-control mode to the local-control mode is a first position of the multiple switch positions, wherein selection of the first position of the multiple switch positions results in selection of the DAQ mode selected by use of the DAQ mode selector while the DAQ device operates in the local-control mode, wherein the position of the control-mode selector that causes the processor to execute stored program instructions to change the operating state of the DAQ device from the local-control mode to the remote-control mode is a second position of the multiple switch positions, and wherein, when the DAQ device operates in the remote-control mode, the wireless transceiver is configured to receive a mode-selection command that identifies, from among the plurality of data-acquisition modes, a data-acquisition mode in which the DAQ device should begin operating.

12. The DAQ device of claim 1, further comprising:

a packet element to place the second input data into data packets when the DAQ device operates in the remote-control mode, wherein transmission of the second input data to the air interface comprises transmission of the data packets to the air interface.

13. The DAQ device of claim 1, wherein, when the DAQ device pairs with the display device, the wireless transceiver receives from the display device a passkey associated with the display device, wherein the computer-readable medium stores the passkey associated with the display device, and wherein, prior to transmission of the second input data to the air interface, the processor executes program instructions, stored by the computer-readable medium, to use the stored passkey to confirm that the DAQ device is paired with the display device.

14. The DAQ device of claim 1, further comprising:

one or more additional selector devices selected from the group consisting of (i) a range selector device, (ii) a graph selector device, (iii) a min/max selector device, and (iv) a variable function selector device, wherein the one or more additional selector devices are inoperable to enter a user-selection while the DAQ device operates in the remote-control mode, and wherein the one or more additional selector devices are configured to enter a user-selection while the DAQ device operates in the local-control mode.

15. The DAQ device of claim 1, wherein the wireless transceiver is configured to receive the mode-selection command from the air interface while the DAQ device operates in the remote-control mode, and wherein the mode-selection command identifies a data-acquisition mode, and wherein the DAQ device is configured to transition to the identified data-acquisition mode for acquiring data.

16. The DAQ device of claim 1, wherein the user interface display does not display the second input data generated from second the input signals received at the input element.

17. The DAQ device of claim 1, wherein the control-mode selector includes a first push button for the first engagement and the control-mode selector includes a second push button distinct from the first push button for the second engagement.

18. The DAQ device of claim 1, wherein the control-mode selector includes a push button for the first engagement when the DAQ device operates in the remote-control mode and the control-mode selector includes the push button for the second engagement when the DAQ device operates in the local-control mode.

19. A method comprising:

engaging or changing a position of a control-mode selector at a data acquisition (DAQ) device to cause a processor to execute program instructions stored at a computer-readable medium to change an operating state of the DAQ device from a remote control mode to a local-control mode, wherein an input element of the DAQ device is configured to acquire first input signals using a DAQ mode selected by use of a DAQ mode selector at the DAQ device while the DAQ device operates in the local-control mode;

generating, by the input element while the DAQ device is operating in the local-control mode, first input data from input signals received at the input element, displaying, by a user interface display located at the DAQ device, the first input data;

engaging or changing a position of the control-mode selector at the DAQ device to cause the processor to execute program instructions stored at the computer-readable medium to change an operating state of the DAQ device from the local-control mode to the remote-control mode;

receiving, by a wireless transceiver of the DAQ device, a mode selection command from the display device remote from the DAQ device, wherein the input element acquires data using a DAQ mode indicated by the received mode selection command while the DAQ device operates in the remote-control mode; and generating, by the input element while the DAQ device is operating in the remote-control mode, second input data from input signals received at the input element of the DAQ device and transmitting, by the wireless transceiver, the second input data to an air interface for transmission of the second input data to the display device remote from the DAQ device, wherein, while the DAQ device is operating in the remote-control mode, the user interface display does not display any input data generated from input signals received at the input element.

20. The method of claim 19, further comprising:

storing, by the computer-readable medium, first computer-readable program instructions executable to cause the DAQ device to transition from the local-control mode to the remote-control mode and second computer-readable program instructions executable to cause the DAQ device to transition from the remote-control mode to the local-control mode;

executing, by the processor, the first program instructions to transition from the local-control mode to the remote-control mode in response to engaging or changing the position of the control-mode selector at the DAQ device to cause the processor to change the operating state of the DAQ device from the local-control mode to the remote-control mode; and executing, by the processor, the second program instructions to transition from the remote-control mode to the local-control mode in response to engaging or changing the position of the control-mode selector at the DAQ device to cause the processor to execute program instructions stored at the computer-readable medium to change an operating state of the DAQ device from the local-control mode to the remote-control mode.

21. The method of claim 20, wherein the transition from the local-control mode to the remote-control mode includes the wireless transceiver transitioning from a transceiver-off-state to a transceiver-on-state, and wherein the transition from the remote-control mode to the local-control mode includes the wireless transceiver transitioning from a transceiver-on-state to a transceiver-off-state.

22. The method of claim 21, wherein the DAQ device comprises one or more additional selector devices, wherein the transition from the local-control mode to the remote-control mode further includes the DAQ device establishing a wireless network with the display device, wherein the display device and DAQ device pair with each other prior to establishing the wireless network, and wherein the one or more additional selector devices are inoperative while the DAQ device operates in the remote-control mode.

23. The method of claim 19, further comprising:

while the DAQ device is operating in the remote-control mode and in a first data-acquisition mode, the wireless transceiver receiving a mode-selection command via the air interface, wherein the mode-selection command identifies a second data-acquisition mode; and responsive to receiving the mode-selection command and while the DAQ device is operating in the remote-control mode, the DAQ device transitioning from the first data-acquisition mode to the second data-acquisition mode.

24. The method of claim 19, further comprising:

receiving, at the wireless transceiver, information regarding connection of an input lead of the input element to an input signal acquisition point of a device-under-service that generates the input signals; and visually presenting, at the display located at the DAQ device, the information regarding connection of an input lead of the input element to an input signal acquisition point of a device-under-service that generates the input signals.

25. The method of claim 19, further comprising:

displaying the second input data by a display located at the display device remote from the DAQ device, wherein displaying the first input data by the user interface display located at the DAQ device comprises displaying the first input data as a first oscilloscope waveform, and wherein displaying the second input data by the display located at the display device remote from the DAQ device comprises displaying the second input data as a second oscilloscope waveform.

* * * * *